US009938579B2

(12) United States Patent
Sarwal

(10) Patent No.: US 9,938,579 B2
(45) Date of Patent: Apr. 10, 2018

(54) BIOMARKER PANEL FOR DIAGNOSIS AND PREDICTION OF GRAFT REJECTION

(75) Inventor: Minnie M. Sarwal, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 824 days.

(21) Appl. No.: 13/144,047

(22) PCT Filed: Jan. 11, 2010

(86) PCT No.: PCT/US2010/020599

§ 371 (c)(1),
(2), (4) Date: Nov. 2, 2011

(87) PCT Pub. No.: WO2010/083121

PCT Pub. Date: Jul. 22, 2010

(65) Prior Publication Data

US 2012/0040358 A1 Feb. 16, 2012

Related U.S. Application Data

(60) Provisional application No. 61/145,059, filed on Jan. 15, 2009.

(51) Int. Cl.
*C12Q 1/68* (2006.01)

(52) U.S. Cl.
CPC ...... *C12Q 1/6883* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS 6,607,879 B1 8/2003 Cocks et al.
7,026,121 B1 * 4/2006 Wohlgemuth ....... C12Q 1/6883 435/6.1
7,879,556 B2 2/2011 Wohlgemuth et al.
2003/0007968 A1 * 1/2003 Larsen ................... A61K 35/28 424/144.1
2003/0017619 A1 1/2003 Rokubo et al.
2003/0022252 A1 * 1/2003 Thomson ............. G01N 33/491 435/7.21
2003/0104371 A1 6/2003 Strom et al.
2004/0163654 A1 8/2004 Williams
2005/0025769 A1 2/2005 Kobayashi et al.
2006/0019256 A1 * 1/2006 Clarke ................. C12N 5/0695 435/6.14
2006/0073496 A1 * 4/2006 O'Toole ............... C12Q 1/6883 435/6.15
2006/0088836 A1 4/2006 Wohlgemuth et al.
2006/0088876 A1 4/2006 Bauer
2006/0246485 A1 * 11/2006 Sarwal ................. C12Q 1/6876 435/6.16
2006/0269949 A1 * 11/2006 Halloran ........................... 435/6
2006/0281122 A1 * 12/2006 Bryant ................. C12Q 1/6886 435/6.16
2007/0031890 A1 * 2/2007 Wohlgemuth et al. ........ 435/7.1
2007/0111210 A1 5/2007 Bigaud et al.
2007/0122806 A1 5/2007 Strom et al.
2007/0134261 A1 * 6/2007 Hancock ................ A61K 38/10 424/185.1
2007/0134728 A1 6/2007 Hu et al.
2007/0212701 A1 9/2007 O'Toole et al.
2007/0232658 A1 10/2007 Wagner et al.
2007/0264272 A1 11/2007 Perreault et al.
2008/0233573 A1 9/2008 Storm et al.
2008/0274906 A1 * 11/2008 Cappola ............... C12Q 1/6881 506/7
2008/0280282 A1 * 11/2008 Bauer, Jr. ............. C12Q 1/6809 435/2
2008/0305493 A1 * 12/2008 Strovel ................ C12Q 1/6886 435/7.1
2009/0022730 A1 1/2009 Raulf et al.
(Continued)

FOREIGN PATENT DOCUMENTS

EP 1731620 12/2006
EP 2080140 A2 * 7/2009
(Continued)

OTHER PUBLICATIONS

Horwitz et al. (Detection of Cardiac Allograft Rejection and Response to Immunosuppressive Therapy With Peripheral Blood Gene Expression, Circulation. 2004;110:3815-3821; originally published online Dec. 6, 2004).*
Martin et al. (Interference of globin genes with biomarker discovery for allograft rejection in peripheral blood samples, Physiol. Genomics 32:190-197, 2008. First published Oct. 30, 2007).*
Affymetrix U133 Array (attached; U133 2.0 available since 2005).*
Affymetrix, GeneChip 3' IVT PLUS Reagent Kit, attached, 2013.*
Patil et al. (Bronchoalveolar lavage cell gene expression in acute lung rejection: development of a diagnostic classifier, Transplantation. Jan. 27, 2008;85(2):224-31).*
Akalin; et al., "Gene expression analysis in human renal allograft biopsy samples using high-density oligoarray technology", Transplantation (2001), 72(5):948-53.
Brouard; et al., "Identification of a peripheral blood transcriptional biomarker panel associated with operational renal allograft tolerance", PNAS (2007), 104(39):15448-15453.
Chan, "Integrating Transcriptomics and Proteomics", Drug Discovery and Development (2006), printed from www.ddmag.com, 6 pages.
(Continued)

*Primary Examiner* — Aaron Priest
(74) *Attorney, Agent, or Firm* — Kyle A. Gurley; Bret E. Field; Bozicevic, Field & Francis LLP

(57) ABSTRACT

Methods are provided for monitoring a subject having a graft for an acute rejection (AR) response, e.g., to predict, to diagnose, and/or to characterize an AR response. In practicing the subject methods, the expression level of at least one gene in a sample from the subject, e.g., a blood or biopsy sample, is evaluated, e.g., at the nucleic acid and/or protein level, to monitor the subject. Also provided are compositions, systems, kits and computer program products that find use in practicing the subject methods.

12 Claims, 35 Drawing Sheets

(56) References Cited

U.S. PATENT DOCUMENTS

2009/0155784 A1* 6/2009 O'Toole .............. C12Q 1/6883 435/6.14
2009/0197286 A1 8/2009 Karin et al.
2009/0220518 A1* 9/2009 Dinarello ............ A61K 38/191 424/141.1
2009/0232825 A1* 9/2009 Gorczynski ...... C07K 14/70503 424/139.1
2009/0269334 A1 10/2009 Bigaud et al.
2009/0304705 A1 12/2009 Grass
2009/0324618 A1* 12/2009 Armstrong ....... G01N 33/57426 424/178.1
2010/0120629 A1 5/2010 Ellis et al.
2010/0234292 A1* 9/2010 Bertucci ............. C12Q 1/6886 514/19.4
2010/0304987 A1* 12/2010 Sanchez Fueyo ... C12Q 1/6881 506/9
2010/0305188 A1* 12/2010 Nakano ............. A61K 31/7088 514/44 A
2011/0064709 A1* 3/2011 Miller ................... A61K 35/15 424/93.71
2011/0171645 A1* 7/2011 McManus ........... C12Q 1/6883 435/6.11
2011/0189680 A1* 8/2011 Keown ............... C12Q 1/6883 435/6.12
2011/0201519 A1* 8/2011 Sarwal et al. .................. 506/9
2013/0157888 A1 6/2013 Nagele

FOREIGN PATENT DOCUMENTS

| | | |
|---|---|---|
| EP | 2295966 | 3/2011 |
| WO | 2004/074815 | 9/2004 |
| WO | 2005/005601 | 1/2005 |
| WO | 2005/070086 | 8/2005 |
| WO | WO 2006082390 A1 * | 8/2006 |
| WO | 2007/104537 | 9/2007 |
| WO | 2007/121922 | 11/2007 |
| WO | 2008/009132 | 1/2008 |
| WO | 2008/084331 | 7/2008 |
| WO | 2009/143624 | 12/2009 |
| WO | 2010038974 | 8/2010 |

OTHER PUBLICATIONS

Chen; et al., "Discordant protein and mRNA expression in lung adenocarcinomas", Molecular and Cellular Proteomics (2002), 1(4):304-13.
Cheung; et al., "Natural Variation in Human Gene Expression Assessed in Lymphoblastoid Cells," Nature Genetics (2003), 33:422-425.
Chu; et al., "Cloning of a new "finger" protein gene (ZNF173) within the class I region of the human MHC", Genomics (1995), 29(1):229-39.
Chua; et al., "Applications of Microarrays to Renal Transplantation: Progress and Possibilities" Frontiers in Bioscience (2003), 8:S913-23.
Database Embl [Online], "Thymidine Kinase, Cytosolic (human), mRNA Sequence", (1998), 2pages, XP002434108, Database accession No. AA778098.
Dugré; et al., "Cytokine and cytotoxic molecule gene expression determined in peripheral blood mononuclear cells in the diagnosis of acute renal rejection.", Transplantation (2000), 70(7):1074-1080.
Enard; et al., "Intra- and interspecific variation in primate gene expression patterns", 296(5566):340-3.
Flechner; et al., "Kidney transplant rejection and tissue injury by gene profiling of biopsies and peripheral blood lymphocytes", American Journal of Transplantation (2004), 4(9):1475-89.
Fujiwaki; et al., "Thymidine Kinase in Epitheliar Ovarian Cancer: Relationship with the Other Pyrimidine Pathway Enzymes", Int. J. Cancer (2002), 99(3):328-335.
Gimino; et al., Gene Expression Profiling of Broncholveolar Lavage Cells in Acute Lung Rejection, American Journal of Respiratory and Critical Care Medicine (2003), 168:1237-1242.
Gronowitz; et al., "Serum Thymidine Kinase in Transplant Patients: Its Relation to Cytomegalovirus Activity, Renal Transplant Rejection and its Use for Monitoring of Antiviral Therapy", Annals of Clinical Research (1986), 18(2):71-75.
Hernandez-Fuentes; et al., "Immunologic monitoring", Immunological Reviews (2003), 196:247-264.
Horwitz; et al., "Detection of Cardiac Allograft Rejection and Response to Immunosuppressive Therapy with Peripheral Blood Gene Expression," Circulation (2004), 110:3815-3821.
Jevnikar; et al., "Late Kidney Allograft Loss: What We Know About It, and What We Can Do About It", Clin J Am Soc Nephrol (2008), 3(S56-S67).
Joosten; et al., "Chronic Renal Allograft Rejection: Pathophysiologic Considerations", Kidney International (2005), 68:1-13.
Li; et al., "Identifying compartment-specific non-HLA targets after renal transplantation by integrating transcriptome and "antibodyome" measures", PNAS (2009), 106(11):4148-4153.
Mansfield; et al., "Arraying the Orchestration of Allograft Pathology", American Journal of Transplantation (2004), 4 (6):853-62.
Marsden, "Predicting Outcomes after Renal Transplantation—New Tools and Old Tools," The New England Journal of Medicine (2003), 349(2):182-184.
Martinez-Llordella; et al., "Using transcriptional profiling to develop a diagnostic test of operational tolerance in liver transplant recipients", The Journal of Clinical Investigations (2008), 118(8):2845-2857.
McMorrow; et al., "New intra-renal graft genes associated with tolerance or rejection", Kidney International, symp. 1 (2002), 61: S85-S93.
Medbury; et al., "The Cytokine and Histological Response in Islet Xenograft Rejection is Dependent Upon Species Combination," Transplantation (1997), 64(9):1307-1314.
Midha; et al., "Chemokine Expression in Nerve Allografts," Neurosurgery (2004), 54(6):1472-149.
O'Riordan; et al., "Bioinformatic Analysis of the Urine Proteome of Acute Allograft Rejection," Journal of American Society of Nephrology (2004), 15:3240-3248.
Sarwal; et al., "Integrative Genomics to Identify Non-HLA Allogenic Kidney-Specific Targets after Kidney Transplantation", Transplantation (2008), 86(25):13, Oral Abstracts, downloaded Apr. 6, 2010.
Sarwal; et al., "Molecular Heterogeneity in Acute Renal Allograft Rejection Identified by DNA Microarray Profiling," New England Journal of Medicine (2003), 349:125-138.
Scherer; et al., "Early Prognosis of the Development of Renal Chronic Allograft Rejection by Gene Expression Profiling of Human Protocol Biopsies", Transplantation (2003), 75(8):1323-30.
Simon; et al., "Serial Peripheral Blood Perforin and Granzyme B Gene Expression Measurements for Prediction of Acute Rejection in Kidney Graft Recipients," American Journal of Transplantation (2003), 3:1121-1127.
Teramoto; et al., "DNA Synthesis in Hepatocytes During Liver Allograft Rejection in Rats", Transplantation (1990), 50(2):199-201.
Thomson; et al., "Monitoring the Patient Off Immunosuppression" Transplantation (2001), 72(8):S13-S22.
Wakui; et al., "Genes Highly Expressed in the Early Phase of Murine Graft-Versus-Host Reaction," Biochemical and Biophysical Communications (2001), 282:200-206.
Whitfield; et al., "Systemic and Cell Type-Specific Gene Expression Patterns in Scleroderma Skin," Proc. Natl. Acad Sci. (2003), 100(21):12319-12324.
Wu, "Analysing Gene Expression Data From DNA Microarrays to Identify Candidate Genes," Journal of Pathology (2001), 195:53-65.
Zhang; et al., "Microarray Analysis of Gene Expression in Peripheral Blood Mononuclear Cells Derived From Long-Surviving Renal Recipients", Transplantation Proceedings (2002), 34:1757-1759.
Communal; et al. "Reciprocal modulation of mitogen-activated protein kinases and mitogen-activated protein kinase phosphatase 1 and 2 in failing human myocardium", J Cardiac Failure (Apr. 2002), 8(2):86-92.

(56) References Cited

OTHER PUBLICATIONS

Alarcon; et al. "Time to renal disease and end-stage renal disease in PROFILE: a multiethnic lupus cohort", PLos Med (Oct. 2006), 3(10):e396.
Gwinner; et al. "Renal transplant rejection markers." World J Urol (Oct. 2007), 25(5):445-455.
Lang; et al. "DUSP meet immunology: dual specificity MAPK phosphatases in control of the inflammatory response", J Immunol (Dec. 2006), 177(11):1497-504.
Ling; et al. "Integrative urinary peptidomics in renal transplantation identifies biomarkers for acute rejection", J Am Soc Nephrol (Apr. 2010), 21(4):646-653.
Rotondi; et al. "High pretransplant serum levels of CXCL9 are associated with increased risk of acute rejection and graft failure in kidney graft recipients", Transpl Int (May 2010), 23(5):465-475.
Sigdel; et al. "Shotgun proteomics identifies proteins specific for acute renal transplant rejection", Proteomics Clin Appl (Jan. 2010), 4(1):32-47.
Voshol; et al. "Evaluation of biomarker discovery approaches to detect protein biomarkers of acute renal allograft rejection", J Proteome Res (Jul.-Aug. 2005), 4(4):1192-1199.
Roedder; et al., "The pits and pearls in translating operational tolerance biomarkers into clinical practice", Current Opinion in Organ Transplantation (Dec. 2012), 17(6):655-662.
Akalin; et al., "Bocking Cell Microtubule Assembly Inhibits the Alloimmune Response In Vitro and Prolongs Renal Allograft Survival by Inhibition of Th1 and Sparing of Th2 Cell Function In Vivo", Journal of the American Society of Nephrology (1995), 5(7):1418-1425.
Braud; et al., "Immunosuppresive Drug-Free Operational Immune Tolerance in Human Kidney Transplant Recipients: Part 1. Blood Gene Expression Statistical Analysis", Journal of Cellular Biochemistry (Apr. 2008), 103(6):1681-1692.
Hauge; et al., "Characterization of the FAM110 gene family", Genomics (May 2007), 90:14-27.
Hillier; et al., "Generation and annotation of the DNA sequences of human chromosomes 2 and 4", Nature (2005), 434:724-731.
Matsuki; et al., "Novel regulation of MHC class II function in B cells", The EMBO Journal (Jan. 2007), 26:846-854.
Saint-Mezard; et al., "Analysis of independent microarray datasets of renal biopsies identifies a robust transcript signature of acute allograft rejection", Transplant International (Mar. 2009), 22(3):293-302.
Butte; et al., "Protein microarrays discover angiotensinogen and PRKRIP1 as novel targets for autoantibodies in chronic renal disease", Mol Cell Proteomics (Mar. 2011), 10(3):M110.000497.
Cox; et al., "Altered modulation of WNT-beta-catenin and PI3K/Akt pathways in IgA nephropathy", Kidney Int (Aug. 2010), 78(4):396-407.
Dinarello; et al., "Anti-inflammatory Agents: Present and Future", Cell (Mar. 2010), 140(6):935-950.
Ismail; et al., "Important fluorinated drugs in experimental and clinical use", Journal of Fluorine Chemistry (Dec. 2002), 118(1):27-33.
Kalil; et al., "Meta-analysis: the efficacy of strategies to prevent organ disease by cytomegalovirus in solid organ transplant recipients", Ann Intern Med (Dec. 2005), 143(12):870-880.
Kaposztas; et al., "Impact of rituximab therapy for treatment of acute humoral rejection", Clin Transplant (Jan.-Feb. 2009), 23(1):63-73.
Metz; et al., "Application of proteomics in the discovery of candidate protein biomarkers in a diabetes autoantibody standardization program sample subset", J Proteome Res (Feb. 2008), 7(2):698-707.
Sato; et al., "Aberrant CD3- and CD3-mediated signaling events in cord blood T Cells are associated with dysfunctional regulation of Fas ligand-mediated cytotoxicity", The Journal of Immunology (Apr. 1999), 162 (8):4464-4471.
Sigdel; et al., "Profiling of autoantibodies in IgA nephropathy, an integrative antibiomics approach", Clin J Am Soc Nephrol (Dec. 2011), 6(12):2775-2784.
Li; et al., "A Peripheral Blood Diagnostic Test for Acute Rejection in Renal Transplantation", American Journal of Transplantation (Oct. 2012), 12(10):2710-2718.
Nesslinger; et al., "A viral vaccine encoding prostate-specific antigen induces antigen spreading to a common set of self-proteins in prostate cancer patients", Clinical Cancer Research (Aug. 2010), 16(15):4046-4056.
"Affymetrix Human genome U133 Plus 2.0 Array", Gene Expression Omnibus (Nov. 2003), XP002627319, 3pgs.
Al-Lamki; et al., "Expression of Tumor Necrosis Factor Receptors in Normal Kidney and Rejecting Renal Transplants", Laboratory Investigation (Nov. 2001), 81(11): 1503-1515.
Chen; et al., "Differentially Expressed RNA from Public Microarray Data Identifies Serum Protein Biomarkers for Cross-Organ Transplant Rejection and Other Conditions", Plos Computational Biology (Sep. 2010), 6(9):e1000940.
Hardiman, "Microarray platforms—comparisons and contrasts", Pharmacogenomics (Jan. 2004), 5(5): 487-502.
Hauser; et al., "Prediction of Acute Renal Allograft Rejection by Urinary Monokine Induced by IFN-gamma (MIG)", The American Society of Nephrology (Jan. 2005), 16(6):1849-1858.
Hidalgo; et al., "The Transcriptome of Human Cytotoxic T Cells: Measuring the Burden of CTL-Associated Transcripts in Human Kidney Transplants", American Journal of Transplantation (Mar. 2008), 8(3):637-646.
Mengel; et al., "Scoring Total Inflammation Is Superior to the Current Banff Inflammation Score in Predicting Outcome and the Degree of Molecular Disturbance in Renal Allografts", American Journal of Transplantation (Aug. 2009), 9(8):1859-1867.
Morgun; et al., "Molecular Profiling Improves Diagnoses of Rejected and Infection in Transplanted Organs", Circulation Research (Jun. 2006), 98(12):e74-83.
Gerrits; et al., "Donor-reactive cytokine production after HLA-identical living related kidney transplantation: a protein-array analysis", (Nov. 2006), 38(9):2825-7.
Joosten; et al., "Antibody response against the glomerular basement membrane protein agrin in patients with transplant glomerulopathy", American Journal of Transplantation (Feb. 2005), 5(2):383-93.
Mizutani; et al., "Frequency of MIC antibody in rejected renal transplant patients without HLA antibody", Human Immunology (Mar. 2006), 67(3):223-9.
Agilent-014850 whole human genome microarray 4×44K G4112F (Probe Name Version), GEO (2008), XP002594592.
Carvalho-Gaspar; et al., "Chemokine gene expression during allograft rejection: Comparison of two quantitative PCR techniques", Journal of Immunological Methods (2005), 301(1-2):41-52.
Farivar; et al., "The role of CC and CXC chemokines in cardiac allograft rejection in rats", Experimental and Molecular Pathology (2005), 78(3):171-176.
Lee et al., "Expression profiling of murine double-negative regularoty T cells suggest mechanisms for prolonged cardiac allograft survival", J. Immunol. (2005), 174(8):4535-4544.
Serody; et al., "T-lymphocyte production of macrophage inflammatory protein-lalpha is critical to the recruitment of CD8(+) T cells to the liver, lung, and spleen during graft-versus-host disease", Blood (2000), 96(9):2973-2980.
Shi; et al., "[Clinical significance of RANTES and MIP-1 alpha in acute rejection episode in kidney transplantation]", Zhongguo Yi Xue Ke Xue Yuan Xue Bao (2004), abstract.
Famulski; et al., "Changes in the Transcriptome in Allograft Rejection: IFN-.gamma.-Induced Transcripts in Mouse Kidney Allografts", American Journal of Transplantation (Jun. 2006), 6(6):1342-1354.
Takahashi et al. "Induction of Pluripotent Stem Cells from Adult Human Fibroblasts by Defined Factors", Cell, vol. 131, Nov. 30, 2007, pp. 861-872.
Shiro, "Organ Transplant and Molecular Pathology", Journal of the Japan Society for Transplantation, 2004, 39(2) pp. 138-144 (Partial English translation only).

(56) References Cited

OTHER PUBLICATIONS

Anglicheau et al. "Noninvasive Prediction of Organ Graft Rejection and Outcome Using Gene Expression Patterns", Transplantation, vol. 86, No. 2, Jul. 27, 2008, pp. 192-199.
Hartono et al. "Noninvasive Diagnosis of Acute Rejection of Renal Allografts", Current Opinion in Organ Transplantation, vol. 15, No. 1, Feb. 2010, pp. 35-41.

* cited by examiner

| Gene | Array (n=59, 31AR) Fold | qscore(%) |
| --- | --- | --- |
| NKTR | −1.5 | 0.2 |
| MAPK9 | −1.8 | 0.0 |
| DUSP1 | 1.7 | 5.6 |
| CFLAR | 1.7 | 3.0 |
| RNF130 | 1.8 | 2.4 |
| PBEF1 | 2.6 | 1.6 |
| IFNGR1 | 2.0 | 4.6 |
| ITGAX | 1.5 | 5.1 |
| PSEN1 | 1.4 | 6.7 |
| RYBP | 1.4 | 7.3 |

| Gene | PCR Verification Set Fold | p value |
| --- | --- | --- |
| NKTR | −2.0 | 0.002 |
| MAPK9 | −2.7 | <0.001 |
| DUSP1 | 3.4 | <0.001 |
| CFLAR | 2.2 | 0.02 |
| RNF130 | 2.7 | 0.03 |
| PBEF1 | 8.8 | <0.001 |
| IFNGR1 | 9.1 | 0.01 |
| ITGAX | 5.3 | 0.001 |
| PSEN1 | 3.6 | <0.001 |
| RYBP | 2.6 | 0.001 |

| Gene | PCR Validation Set 1 Fold | p value |
| --- | --- | --- |
| NKTR | −3.5 | 0.002 |
| MAPK9 | −2.1 | 0.003 |
| DUSP1 | 3.9 | <0.001 |
| PBEF1 | 7.4 | <0.001 |
| PSEN1 | 7.2 | <0.001 |

FIG. 3
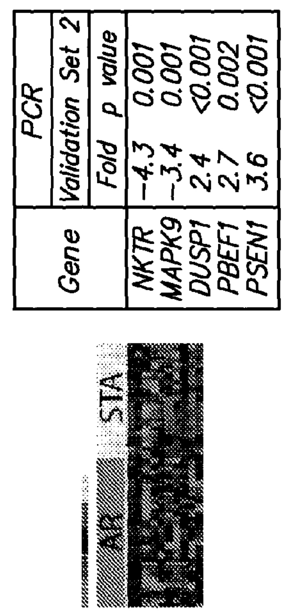
| Gene | PCR Validation Set 2 | |
|---|---|---|
| | Fold | p value |
| NKTR | −4.3 | 0.001 |
| MAPK9 | −3.4 | 0.001 |
| DUSP1 | 2.4 | <0.001 |
| PBEF1 | 2.7 | 0.002 |
| PSEN1 | 3.6 | <0.001 |
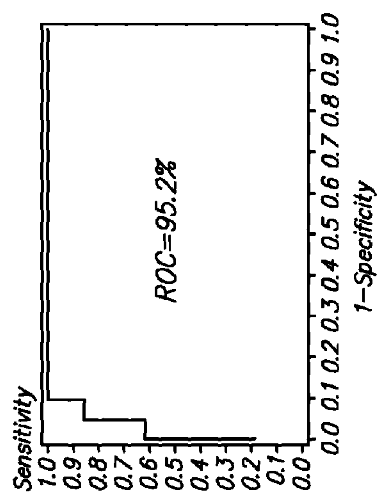
FIG. 4A
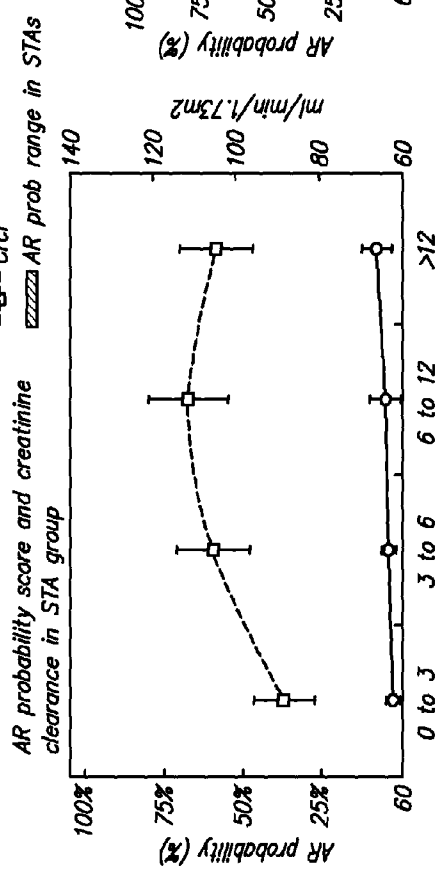
FIG. 4B
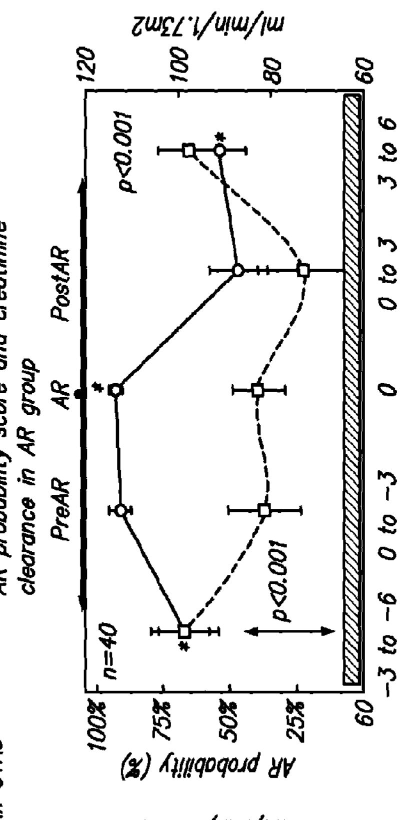

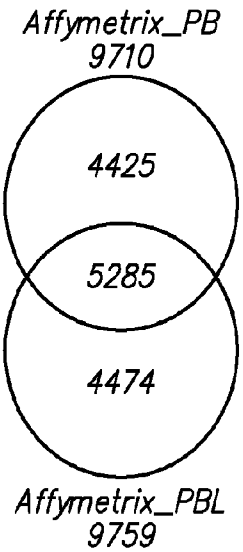

FIG. 5A

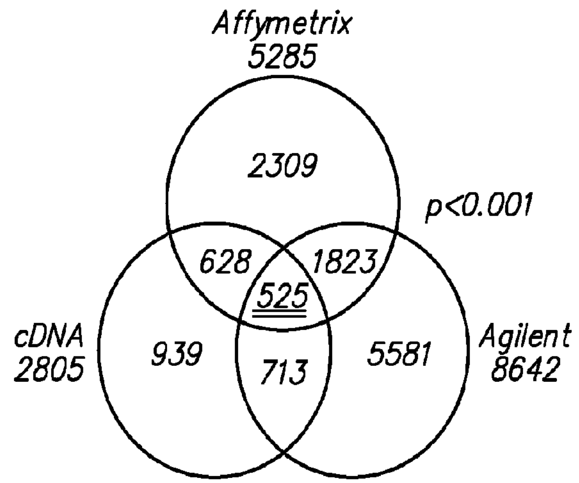

FIG. 5B

| Gene Symbol | GeneName | ABI Probe ID |
|---|---|---|
| DUSP1 | Dual specificity phosphatase 1 | Hs00610256_ml |
| CFLAR | CASP8 and FADD-like apoptosis regulator | Hs00236002_ml |
| IFNGR1 | Interferon-gamma receptor 1 | Hs00166223_ml |
| ITGAX | Integrin, alpha X (complement component 3 receptor 4 subunit) | Hs00174217_ml |
| MAPK9 | Mitogen-activated protein kinase 9 | Hs00177102_ml |
| NKTR | Natural killer-tumor recognition sequence | Hs00234637_ml |
| PBEF1 | pre-B-cell colony enhancing factor 1 | Hs00237184_ml |
| PSEN1 | Presenilin 1 (Alzheimer disease 3) | Hs00997789_ml |
| RNF130 | Ring finger protein 130 | Hs00218335_ml |
| RYBP | RING1 and YY 1 binding protein | Hs00171928_ml |
| PFN1 | Profilin 1 | Hs00748915_sl |
| GZMB | Granzyme B | Hs00234637_ml |
| FOXP3 | Forkhead box P3 | Hs00203958_ml |

FIG. 6A

Normalized Expression Values for 10 genes by Q-PCR across 34 Blood Samples (17 AR, 17 STA) in the Verification Set

| Unique Sample IDs for Verification Set | CFLAR | DUSP1 | IFNGR1 | ITGAX | MAPK9 | NKTR | PBEF1 | PSEN1 | RNF130 | RYBP |
|---|---|---|---|---|---|---|---|---|---|---|
| A04 | 5.0 | 6.7 | 37.5 | 5.5 | 1.9 | 2.6 | 9.4 | 5.1 | 0.6 | 4.7 |
| A09 | 22.1 | 2.7 | 8.2 | 11.3 | 0.1 | 0.2 | 6.1 | 9.1 | 1.7 | 9.1 |
| A20 | 3.1 | 1.6 | 3.0 | 5.7 | 1.3 | 1.3 | 1.9 | 2.4 | 1.2 | 4.2 |
| A11 | 3.6 | 2.6 | 4.4 | 3.1 | 0.5 | 0.9 | 1.6 | 1.9 | 5.4 | 1.4 |
| A12 | 4.1 | 2.4 | 16.8 | 5.9 | 1.4 | 1.2 | 1.3 | 6.8 | 3.2 | 1.7 |
| A14 | 4.8 | 1.6 | 2.0 | 1.2 | 1.0 | 1.8 | 1.6 | 2.0 | 4.6 | 2.5 |
| A15 | 8.1 | 4.9 | 2.2 | 10.7 | 1.1 | 1.5 | 2.0 | 2.5 | 2.2 | 1.8 |
| A17 | 4.6 | 1.2 | 2.1 | 2.2 | 0.4 | 0.3 | 1.8 | 3.3 | 0.9 | 2.5 |
| A21 | 3.9 | 2.1 | 4.3 | 1.4 | 0.5 | 1.4 | 5.6 | 2.9 | 1.2 | 5.5 |
| A48 | 4.1 | 2.9 | 4.9 | 1.2 | 0.5 | 0.6 | 4.1 | 2.3 | 1.1 | 3.1 |
| A22 | 5.5 | 6.6 | 1.6 | 1.1 | 0.6 | 1.9 | 3.8 | 3.4 | 0.9 | 2.7 |
| A23 | 1.8 | 1.2 | 26.6 | 1.3 | 0.2 | 0.5 | 4.2 | 2.7 | 10.2 | 4.1 |
| A25 | 4.6 | 1.3 | 6.8 | 5.7 | 0.4 | 0.4 | 4.5 | 3.1 | 6.1 | 3.5 |
| A26 | 5.3 | 4.8 | 4.0 | 1.3 | 0.2 | 0.3 | 4.9 | 1.6 | 0.4 | 1.4 |
| A30 | 10.1 | 1.8 | 8.9 | 1.6 | 0.1 | 0.1 | 0.5 | 5.9 | 1.3 | 1.2 |
| A31 | 4.1 | 2.8 | 33.6 | 5.9 | 0.1 | 0.1 | 1.3 | 6.8 | 1.3 | 1.7 |
| A38 | 3.4 | 4.2 | 2.1 | 1.7 | 0.8 | 0.3 | 2.0 | 2.8 | 0.3 | 2.0 |
| S30 | 1.5 | 0.4 | 1.8 | 0.9 | 9.5 | 2.0 | 0.4 | 0.5 | 0.7 | 0.9 |
| S19 | 1.4 | 0.2 | 0.8 | 0.9 | 2.5 | 1.1 | 0.4 | 0.6 | 0.8 | 1.0 |
| S31 | 0.5 | 1.5 | 0.4 | 1.0 | 2.2 | 1.7 | 0.4 | 0.5 | 2.2 | 0.5 |
| S32 | 1.8 | 1.7 | 1.0 | 2.1 | 2.0 | 2.5 | 0.6 | 0.4 | 3.9 | 1.0 |
| S33 | 1.4 | 0.4 | 1.7 | 0.9 | 2.0 | 2.0 | 0.4 | 0.5 | 0.7 | 0.9 |
| S35 | 1.8 | 0.6 | 1.4 | 0.5 | 3.8 | 1.6 | 0.2 | 2.7 | 1.0 | 1.2 |
| S36 | 2.6 | 0.6 | 0.7 | 0.6 | 4.7 | 3.8 | 0.2 | 1.8 | 0.1 | 1.7 |
| S37 | 2.8 | 0.8 | 0.6 | 0.5 | 2.9 | 2.6 | 0.2 | 0.7 | 0.2 | 1.9 |
| S23 | 3.3 | 1.2 | 0.8 | 0.7 | 1.9 | 0.7 | 0.2 | 1.0 | 0.3 | 1.7 |
| S39 | 4.4 | 0.6 | 1.2 | 0.3 | 2.2 | 0.6 | 0.1 | 0.6 | 0.9 | 1.3 |
| S41 | 5.6 | 1.0 | 0.6 | 0.4 | 1.8 | 1.3 | 0.2 | 3.0 | 0.2 | 0.9 |
| S42 | 1.4 | 1.3 | 2.0 | 0.3 | 1.8 | 2.3 | 0.2 | 1.9 | 0.6 | 1.1 |
| S43 | 2.3 | 0.6 | 1.5 | 0.3 | 2.2 | 2.7 | 0.2 | 0.7 | 0.9 | 1.7 |
| S24 | 4.4 | 0.6 | 0.9 | 0.3 | 2.2 | 0.7 | 0.8 | 0.5 | 0.3 | 1.2 |
| S44 | 5.9 | 1.0 | 1.4 | 0.3 | 6.7 | 3.5 | 1.1 | 0.8 | 0.1 | 0.9 |
| S46 | 1.4 | 2.2 | 0.9 | 1.4 | 3.3 | 2.2 | 0.2 | 1.0 | 2.6 | 1.2 |
| S47 | 2.7 | 0.2 | 0.9 | 1.0 | 5.1 | 1.1 | 0.5 | 0.6 | 0.4 | 1.1 |
| AR_mean | 6 | 3 | 10 | 4 | 1 | 1 | 3 | 4 | 2 | 3 |
| STA_mean | 2.7 | 0.9 | 1.1 | 0.7 | 3.3 | 1.9 | 0.4 | 1.0 | 0.9 | 1.2 |
| FOLD(AR/STA) | 2.2 | 3.4 | 9.1 | 5.3 | −2.7 | −2.0 | 8.8 | 3.6 | 2.7 | 2.6 |
| T test | 0.02 | 0.0002 | 0.01 | 0.001 | 0.0001 | 0.002 | 0.0001 | 0.0001 | 0.03 | 0.001 |

FIG. 6B

Summary of Gene Expression Values on Array and by Q-PCR for 3 genes selected form literature review as differentially expressed in AR across the 34 samples in the Verification Set

| Gene | Array | | | | | | | | qPCR | |
|---|---|---|---|---|---|---|---|---|---|---|
| | Affy_PB | | Affy_PBL | | cDNA | | Agilent | | | |
| | q | fold | q | fold | q | fold | q | fold | Fold | p |
| PFN1 | NA | NA | NA | NA | 0.02 | −1.6 | NA | NA | 1.8 | 0.1 |
| GZMB | NA | NA | 4.4 | −1.6 | NA | NA | 0.3 | −3.6 | 2.2 | 0.03 |
| FOXP3 | NA | NA | NA | NA | NA | NA | NA | NA | 2.6 | 0.001 |

FIG. 7

Normalized Expression Values for 10 genes by Q-PCR across 42 Independent Blood Samples (21 AR, 21 STA) in Validation Set 1

| Unique Sample ID in Validation Set 1 | CFLAR | DUSP1 | IFNGR1 | ITGAX | MAPK9 | NKTR | PBEF1 | PSEN1 | RNF130 | RYBP |
|---|---|---|---|---|---|---|---|---|---|---|
| A49 | 14.5 | 4.1 | 5.3 | 17.1 | 2.2 | 0.6 | 6.6 | 11.4 | 10.7 | 2.8 |
| A50 | 2.7 | 2.5 | 4.0 | 2.0 | 0.9 | 1.4 | 2.6 | 17.8 | 2.3 | 1.5 |
| A51 | 16.7 | 3.0 | 3.9 | 7.5 | 0.7 | 0.3 | 4.6 | 3.7 | 2.4 | 8.5 |
| A52 | 2.2 | 4.8 | 13.1 | 2.7 | 0.6 | 1.2 | 3.0 | 9.9 | 2.8 | 1.8 |
| A53 | 1.9 | 2.8 | 2.2 | 1.9 | 1.6 | 1.5 | 1.2 | 4.8 | 3.9 | 1.4 |
| A54 | 3.9 | 2.5 | 2.5 | 6.7 | 0.3 | 1.0 | 2.7 | 2.4 | 5.2 | 3.0 |
| A55 | 2.1 | 3.9 | 1.8 | 3.0 | 0.8 | 0.2 | 2.0 | 1.0 | 5.6 | 5.7 |
| A56 | 3.5 | 1.4 | 2.2 | 2.8 | 0.8 | 0.2 | 2.0 | 2.3 | 3.6 | 10.3 |
| A57 | 14.9 | 4.3 | 1.2 | 5.8 | 0.5 | 0.6 | 7.6 | 12.5 | 4.3 | 9.5 |
| A58 | 13.9 | 6.6 | 7.9 | 11.0 | 0.3 | 0.1 | 5.7 | 5.6 | 1.3 | 10.7 |
| A59 | 3.9 | 2.7 | 2.5 | 6.7 | 0.4 | 0.4 | 2.0 | 3.8 | 1.8 | 1.9 |
| A60 | 4.8 | 10.2 | 1.7 | 17.9 | 0.1 | 2.0 | 2.3 | 3.9 | 6.9 | 9.6 |
| A61 | 0.5 | 0.3 | 0.4 | 1.0 | 0.6 | 0.2 | 1.9 | 3.7 | 1.1 | 4.8 |
| A62 | 3.7 | 1.3 | 2.0 | 6.1 | 0.4 | 0.5 | 1.7 | 7.9 | 6.3 | 5.7 |
| A63 | 7.5 | 5.9 | 2.9 | 11.0 | 0.6 | 0.5 | 7.7 | 7.4 | 1.3 | 23.7 |
| A64 | 2.5 | 1.5 | 3.6 | 5.8 | 0.2 | 0.5 | 2.3 | 6.8 | 0.3 | 1.2 |
| A65 | 3.2 | 9.8 | 2.2 | 9.2 | 1.1 | 0.2 | 0.9 | 4.9 | 1.1 | 32.0 |
| A66 | 2.8 | 3.6 | 1.9 | 3.2 | 0.8 | 0.2 | 1.8 | 1.2 | 1.5 | 1.3 |
| A67 | 5.0 | 3.9 | 3.8 | 4.6 | 0.6 | 0.3 | 4.8 | 4.6 | 27.1 | 7.8 |
| A68 | 2.5 | 4.4 | 7.1 | 2.9 | 0.2 | 0.9 | 1.2 | 2.7 | 0.1 | 1.2 |
| A69 | 5.9 | 3.3 | 11.7 | 11.4 | 0.9 | 0.7 | 3.4 | 4.9 | 4.7 | 2.7 |
| S15 | 2.1 | 0.9 | 0.9 | 0.7 | 1.1 | 0.9 | 0.8 | 0.8 | 0.8 | 0.5 |
| S57 | 1.3 | 1.8 | 0.8 | 3.3 | 1.3 | 8.2 | 0.3 | 0.5 | 0.6 | 2.8 |
| S58 | 2.5 | 0.5 | 2.2 | 4.7 | 2.4 | 1.8 | 0.6 | 1.1 | 1.0 | 2.7 |
| S59 | 1.2 | 0.2 | 0.6 | 1.8 | 0.7 | 2.0 | 0.2 | 0.4 | 0.1 | 1.2 |
| S60 | 3.3 | 0.7 | 1.6 | 1.3 | 1.4 | 4.6 | 0.6 | 1.6 | 0.8 | 2.4 |
| S61 | 1.5 | 1.3 | 3.1 | 2.5 | 2.1 | 1.1 | 1.0 | 1.0 | 1.0 | 1.5 |
| S62 | 1.9 | 0.9 | 0.8 | 1.1 | 3.3 | 1.5 | 0.1 | 0.6 | 0.7 | 2.6 |
| S63 | 2.6 | 2.0 | 3.4 | 8.4 | 1.4 | 0.8 | 0.5 | 1.1 | 1.1 | 1.6 |
| S64 | 1.0 | 1.9 | 1.3 | 2.6 | 1.0 | 3.9 | 0.1 | 0.8 | 0.5 | 0.8 |
| S65 | 0.3 | 0.2 | 0.2 | 0.8 | 0.3 | 1.4 | 0.0 | 0.1 | 0.2 | 0.5 |
| S66 | 0.5 | 0.9 | 0.2 | 1.1 | 1.1 | 0.2 | 0.1 | 0.1 | 0.2 | 0.9 |
| S67 | 3.7 | 0.5 | 1.6 | 7.7 | 3.5 | 1.3 | 1.5 | 1.6 | 3.3 | 3.5 |
| S68 | 1.5 | 2.0 | 1.8 | 6.2 | 0.8 | 3.4 | 0.3 | 1.0 | 0.7 | 1.4 |
| S69 | 1.9 | 2.1 | 2.0 | 2.8 | 0.4 | 1.5 | 0.2 | 1.3 | 2.0 | 1.9 |
| S70 | 1.2 | 2.1 | 0.6 | 1.8 | 1.0 | 2.8 | 0.2 | 0.4 | 0.1 | 1.2 |
| S71 | 2.6 | 0.3 | 2.6 | 5.6 | 0.1 | 1.7 | 0.6 | 1.2 | 2.1 | 2.5 |
| S72 | 3.8 | 0.7 | 3.0 | 8.2 | 1.2 | 1.1 | 0.7 | 1.4 | 1.5 | 3.2 |
| S73 | 3.5 | 0.2 | 1.5 | 2.1 | 3.3 | 0.8 | 0.2 | 0.5 | 0.5 | 1.5 |

FIG. 8

| | | | | | | | | | | |
|---|---|---|---|---|---|---|---|---|---|---|
| S74 | 0.2 | 0.2 | 0.1 | 0.6 | 3.3 | 6.5 | 0.1 | 0.1 | 0.3 | 1.7 |
| S75 | 0.2 | 1.3 | 0.1 | 0.5 | 0.6 | 0.7 | 0.0 | 0.1 | 0.1 | 0.2 |
| S76 | 2.2 | 0.7 | 4.2 | 9.1 | 1.4 | 1.0 | 0.8 | 1.1 | 0.7 | 3.1 |
| AR_mean | 5.7 | 3.9 | 4.0 | 6.7 | 0.7 | 0.6 | 3.3 | 5.9 | 4.5 | 7.0 |
| STA_mean | 1.9 | 1.0 | 1.6 | 3.5 | 1.5 | 2.2 | 0.4 | 0.8 | 0.9 | 1.8 |
| FOLD(AR/STA) | 3.0 | 3.9 | 2.5 | 1.9 | 0.5 | 0.3 | 7.4 | 7.2 | 5.0 | 3.9 |
| T test | 0.002 | 0.00003 | 0.004 | 0.013 | 0.003 | 0.002 | 0.00001 | 0.00002 | 0.010 | 0.006 |

Normalized Expression Values for 5 genes by Q-PCR across 64 Independent Blood Samples (32 AR, 32 STA) in Validation Set 2

| Unique Sample IDs for Validation Set 2 | phenotype (AR=1; STA=0) | DUSP1 | MAPK9 | NKTR | PBEF1 | PSEN1 | AR Probability | Predict AR | TP | FP | TN | FN |
|---|---|---|---|---|---|---|---|---|---|---|---|---|
| A70 | 1 | 2.2 | 1.7 | 0.5 | 2.0 | 3.5 | 100% | 1 | TRUE | FALSE | FALSE | FALSE |
| A71 | 1 | 1.5 | 0.3 | 0.3 | 1.6 | 2.1 | 98% | 1 | TRUE | FALSE | FALSE | FALSE |
| A72 | 1 | 3.5 | 0.0 | 0.1 | 0.4 | 2.8 | 99% | 1 | TRUE | FALSE | FALSE | FALSE |
| A73 | 1 | 5.7 | 0.1 | 0.3 | 0.5 | 8.7 | 100% | 1 | TRUE | FALSE | FALSE | FALSE |
| A74 | 1 | 0.1 | 0.0 | 0.1 | 15.6 | 8.1 | 100% | 1 | TRUE | FALSE | FALSE | FALSE |
| A75 | 1 | 1.1 | 0.6 | 0.8 | 2.1 | 2.2 | 99% | 1 | TRUE | FALSE | FALSE | FALSE |
| A76 | 1 | 2.1 | 0.1 | 0.1 | 1.8 | 2.8 | 100% | 1 | TRUE | FALSE | FALSE | FALSE |
| A77 | 1 | 1.5 | 0.2 | 0.4 | 5.2 | 1.1 | 100% | 1 | TRUE | FALSE | FALSE | FALSE |
| A78 | 1 | 2.2 | 0.0 | 0.0 | 3.0 | 2.1 | 100% | 1 | TRUE | FALSE | FALSE | FALSE |
| A79 | 1 | 1.6 | 0.4 | 0.2 | 2.5 | 2.8 | 100% | 1 | TRUE | FALSE | FALSE | FALSE |
| A80 | 1 | 6.3 | 0.0 | 0.1 | 1.3 | 5.1 | 100% | 1 | TRUE | FALSE | FALSE | FALSE |
| A81 | 1 | 0.9 | 0.1 | 0.1 | 4.6 | 6.9 | 100% | 1 | TRUE | FALSE | FALSE | FALSE |
| A82 | 1 | 1.5 | 0.0 | 0.0 | 2.8 | 2.1 | 100% | 1 | TRUE | FALSE | FALSE | FALSE |
| A83 | 1 | 2.7 | 0.0 | 0.1 | 2.7 | 3.3 | 100% | 1 | TRUE | FALSE | FALSE | FALSE |
| A84 | 1 | 0.2 | 0.6 | 0.0 | 2.9 | 4.1 | 100% | 1 | TRUE | FALSE | FALSE | FALSE |
| A85 | 1 | 1.0 | 0.6 | 0.2 | 3.8 | 4.8 | 100% | 1 | TRUE | FALSE | FALSE | FALSE |
| A86 | 1 | 1.5 | 0.0 | 0.0 | 3.1 | 3.9 | 100% | 1 | TRUE | FALSE | FALSE | FALSE |
| A87 | 1 | 2.1 | 2.3 | 1.3 | 2.5 | 15.6 | 100% | 1 | TRUE | FALSE | FALSE | FALSE |
| A88 | 1 | 4.6 | 0.3 | 0.8 | 2.0 | 5.4 | 100% | 1 | TRUE | FALSE | FALSE | FALSE |
| A89 | 1 | 3.1 | 0.0 | 0.6 | 2.1 | 5.8 | 100% | 1 | TRUE | FALSE | FALSE | FALSE |
| A90 | 1 | 0.8 | 0.7 | 0.7 | 2.0 | 3.5 | 100% | 1 | TRUE | FALSE | FALSE | FALSE |
| A91 | 1 | 1.6 | 0.6 | 0.0 | 1.7 | 4.3 | 100% | 1 | TRUE | FALSE | FALSE | FALSE |
| A92 | 1 | 3.1 | 0.2 | 0.1 | 1.1 | 1.8 | 99% | 1 | TRUE | FALSE | FALSE | FALSE |
| A93 | 1 | 2.1 | 0.2 | 0.2 | 2.3 | 1.5 | 100% | 1 | TRUE | FALSE | FALSE | FALSE |
| A94 | 1 | 6.9 | 0.7 | 0.6 | 1.2 | 3.1 | 100% | 1 | TRUE | FALSE | FALSE | FALSE |
| A95 | 1 | 1.7 | 0.4 | 0.3 | 1.8 | 2.7 | 100% | 1 | TRUE | FALSE | FALSE | FALSE |
| A96 | 1 | 2.3 | 0.3 | 0.7 | 1.3 | 5.5 | 100% | 1 | TRUE | FALSE | FALSE | FALSE |
| A97 | 1 | 2.5 | 0.1 | 0.1 | 2.1 | 2.5 | 100% | 1 | TRUE | FALSE | FALSE | FALSE |
| A98 | 1 | 1.6 | 0.2 | 0.1 | 2.5 | 1.0 | 100% | 1 | TRUE | FALSE | FALSE | FALSE |
| A99 | 1 | 3.3 | 1.5 | 0.1 | 1.1 | 2.4 | 97% | 1 | TRUE | FALSE | FALSE | FALSE |
| A100 | 1 | 0.9 | 0.7 | 0.6 | 1.6 | 3.3 | 98% | 1 | TRUE | FALSE | FALSE | FALSE |
| A101 | 1 | 7.3 | 0.0 | 0.1 | 1.0 | 0.5 | 100% | 1 | TRUE | FALSE | FALSE | FALSE |

| Confidence | original |
|---|---|
| Sensitivity | 100.0% |
| PPV | 94.1% |
| Specificity | 93.8% |
| NPV | 100.0% |

| | | | | | | | | | | | | |
|---|---|---|---|---|---|---|---|---|---|---|---|---|
| S77 | 0 | 1.0 | 1.8 | 1.2 | 1.5 | 2.2 | 13% | 0 | FALSE | FALSE | TRUE | FALSE |
| S78 | 0 | 0.3 | 1.9 | 1.7 | 0.5 | 0.5 | 0% | 0 | FALSE | FALSE | TRUE | FALSE |
| S79 | 0 | 1.8 | 0.7 | 1.4 | 0.4 | 0.4 | 0% | 0 | FALSE | FALSE | TRUE | FALSE |
| S80 | 0 | 0.9 | 0.1 | 0.5 | 1.2 | 0.4 | 8% | 0 | FALSE | FALSE | TRUE | FALSE |
| S81 | 0 | 0.2 | 2.0 | 1.9 | 0.1 | 0.5 | 0% | 0 | FALSE | FALSE | TRUE | FALSE |
| S82 | 0 | 2.0 | 0.9 | 0.7 | 1.0 | 1.5 | 21% | 0 | FALSE | FALSE | TRUE | FALSE |
| S83 | 0 | 1.7 | 1.4 | 1.5 | 1.4 | 1.1 | 5% | 0 | FALSE | FALSE | TRUE | FALSE |
| S84 | 0 | 0.4 | 4.5 | 2.1 | 2.3 | 0.9 | 0% | 0 | FALSE | FALSE | TRUE | FALSE |
| S85 | 0 | 1.3 | 1.8 | 2.6 | 2.7 | 1.2 | 41% | 0 | FALSE | FALSE | TRUE | FALSE |
| S86 | 0 | 0.8 | 2.0 | 1.9 | 1.4 | 2.6 | 3% | 0 | FALSE | FALSE | TRUE | FALSE |
| S87 | 0 | 0.3 | 0.9 | 3.8 | 0.1 | 1.2 | 0% | 0 | FALSE | FALSE | TRUE | FALSE |
| S88 | 0 | 0.8 | 1.9 | 1.1 | 1.2 | 4.4 | 72% | 1 | FALSE | TRUE | FALSE | FALSE |
| S89 | 0 | 0.2 | 2.0 | 0.8 | 1.4 | 3.6 | 42% | 0 | FALSE | FALSE | TRUE | FALSE |
| S90 | 0 | 0.5 | 2.0 | 1.0 | 2.0 | 1.0 | 5% | 0 | FALSE | FALSE | TRUE | FALSE |
| S91 | 0 | 1.7 | 0.1 | 1.6 | 1.3 | 0.7 | 10% | 0 | FALSE | FALSE | TRUE | FALSE |
| S92 | 0 | 2.2 | 1.4 | 0.8 | 1.1 | 1.4 | 13% | 0 | FALSE | FALSE | TRUE | FALSE |
| S93 | 0 | 1.8 | 0.4 | 0.5 | 0.3 | 0.9 | 1% | 0 | FALSE | FALSE | TRUE | FALSE |
| S94 | 0 | 0.1 | 0.1 | 0.4 | 0.6 | 0.4 | 0% | 0 | FALSE | FALSE | TRUE | FALSE |
| S95 | 0 | 0.3 | 2.3 | 1.0 | 1.1 | 0.7 | 0% | 0 | FALSE | FALSE | TRUE | FALSE |
| S96 | 0 | 0.2 | 1.9 | 0.9 | 0.1 | 0.4 | 0% | 0 | FALSE | FALSE | TRUE | FALSE |
| S97 | 0 | 0.3 | 2.2 | 1.0 | 1.0 | 0.8 | 0% | 0 | FALSE | FALSE | TRUE | FALSE |
| S98 | 0 | 0.2 | 2.2 | 1.3 | 0.3 | 0.7 | 0% | 0 | FALSE | FALSE | TRUE | FALSE |
| S99 | 0 | 1.6 | 1.1 | 0.5 | 1.3 | 1.9 | 58% | 1 | FALSE | TRUE | FALSE | FALSE |
| S100 | 0 | 3.4 | 2.1 | 3.1 | 1.3 | 0.6 | 0% | 0 | FALSE | FALSE | TRUE | FALSE |
| S101 | 0 | 0.5 | 1.5 | 1.2 | 1.5 | 1.0 | 1% | 0 | FALSE | FALSE | TRUE | FALSE |
| S102 | 0 | 0.2 | 2.3 | 1.5 | 0.8 | 0.8 | 0% | 0 | FALSE | FALSE | TRUE | FALSE |
| S103 | 0 | 1.4 | 0.1 | 0.6 | 1.3 | 0.8 | 35% | 0 | FALSE | FALSE | TRUE | FALSE |
| S104 | 0 | 0.3 | 0.1 | 0.4 | 0.1 | 0.3 | 0% | 0 | FALSE | FALSE | TRUE | FALSE |
| S105 | 0 | 3.2 | 0.9 | 1.6 | 0.1 | 0.3 | 0% | 0 | FALSE | FALSE | TRUE | FALSE |
| S106 | 0 | 1.7 | 1.9 | 2.1 | 0.8 | 0.8 | 0% | 0 | FALSE | FALSE | TRUE | FALSE |
| S107 | 0 | 1.1 | 0.7 | 0.8 | 0.3 | 0.2 | 0% | 0 | FALSE | FALSE | TRUE | FALSE |
| S108 | 0 | 0.2 | 0.1 | 0.5 | 0.4 | 0.4 | 0% | 0 | FALSE | FALSE | TRUE | FALSE |
| AR_mean | | 1.0 | 1.4 | 1.3 | 1.0 | 1.1 | | | | | | |
| STA_mean | | 2.5 | 0.4 | 0.3 | 2.6 | 3.9 | n=TRUE | | 32 | 2 | 30 | 0 |
| FOLD(AR/STA) | | 2.4 | 0.3 | 0.2 | 2.7 | 3.6 | | | | | | |
| T test | | <0.001 | <0.001 | <0.001 | 0.002 | <0.001 | | | | | | |

FIG. 9 (CONT.)

Testing Multiple Methods for building Classification Models for AR Classification Across the 10 gene-set
Train: Validation Set 1; Test: Validation Set 2 (10 genes)

| Method | PPV | NPV | Sensitivity | Specificity | Accuracy |
|---|---|---|---|---|---|
| ClassificationViaRegression | 75% | 92% | 94% | 69% | 81% |
| NaiveBayes | 89% | 100% | 100% | 88% | 94% |
| NaiveBayesMultinomial | 82% | 100% | 100% | 78% | 89% |
| NaiveBayesSimple | 89% | 100% | 100% | 88% | 94% |
| NaiveBayesUpdateable | 89% | 100% | 100% | 88% | 94% |
| MultilayerPerceptron (Neural network) | 94% | 100% | 100% | 94% | 97% |
| BayesNet | 97% | 100% | 100% | 97% | 98% |
| Logistic (Multinomial logistic regression) | 100% | 100% | 100% | 100% | 100% |
| SimpleLogistic (Linear logistic regression) | 91% | 94% | 94% | 91% | 92% |
| Sequential Minimal optimization (SMO) | 94% | 100% | 100% | 94% | 97% |

Testing Multiple Methods for building Classification Models for AR Classification Across the 5 gene-set. The model that performs best (Logistic Regression) is highlighted
Train: Validation Set 1; Test: Validation Set 2 (5 genes)

| Method | PPV | NPV | Sensitivity | Specificity | Accuracy |
|---|---|---|---|---|---|
| ClassificationViaRegression | 75% | 92% | 94% | 69% | 81% |
| NaiveBayes | 86% | 100% | 100% | 84% | 92% |
| NaiveBayesMultinomial | 80% | 100% | 100% | 75% | 88% |
| NaiveBayesSimple | 84% | 100% | 100% | 81% | 91% |
| NaiveBayesUpdateable | 86% | 100% | 100% | 84% | 92% |
| MultilayerPerceptron (Neural network) | 86% | 100% | 100% | 84% | 92% |
| BayesNet | 80% | 100% | 100% | 75% | 88% |
| Logistic (Multinomial logistic regression) | 91% | 100% | 100% | 91% | 95% |
| SimpleLogistic (Linear logistic regression) | 91% | 94% | 94% | 91% | 92% |
| Sequential Minimal optimization (SMO) | 100% | 84% | 81% | 100% | 91% |

The 18 Demographic and Clincial Confounders Examined for all Q-PCR Experiments

| | post_Tx_time | Recipient Age | Recipient Gender | Donor Gender | Donor Source | Donor Age | Steroid-Free (SF) vs. Steroid-Based (SB) | WBC count | Heamtocrit (HCT) | CMV+=1 | EBV+=1 | BKV+=1 | bacterial Infection=1 | Donor Specific Antig | PRA (1=yes) | Induction(Daclizuma | FK=1/CSA=2 | MMF=1/AZA=2 |
|---|---|---|---|---|---|---|---|---|---|---|---|---|---|---|---|---|---|---|
| A04 | 7.2 | 14.9 | M | F | LRD | 44.9 | SF | 9.7 | 37.6 | 2 | 2 | 2 | 2 | 1 | 2 | 1 | 1 | 1 |
| A09 | 20.1 | 12.1 | M | M | LRD | 34.1 | SB | 7.9 | 34.9 | 2 | 2 | 2 | 2 | 1 | 2 | 1 | 1 | 1 |
| A11 | 68.7 | 12.2 | M | F | LRD | 47.0 | SB | 4.6 | 36.0 | 2 | 2 | 2 | 2 | 1 | 2 | 2 | 2 | 2 |
| A12 | 140.5 | 4.2 | M | M | LRD | 22.0 | SB | 14.6 | 38.2 | 2 | 2 | 2 | 1 | 1 | 2 | 2 | 2 | 2 |
| A14 | 9.3 | 18.7 | F | M | LRD | 38.9 | SF | 2.3 | 22.4 | 2 | 2 | 2 | 1 | 1 | 2 | 1 | 1 | 1 |
| A15 | 54.9 | 11.8 | F | M | LRD | 37.7 | SB | 12.1 | 32.0 | 2 | 2 | 2 | 2 | 1 | 2 | 2 | 2 | 2 |
| A17 | 97.6 | 10.1 | M | M | LRD | 34.2 | SB | 8.2 | 33.7 | 2 | 2 | 2 | 2 | 1 | 2 | 2 | 2 | 2 |
| A20 | 14.1 | 13.0 | M | NA | CAD | NA | SB | 6.4 | 30.2 | 2 | 2 | 2 | 2 | 1 | 1 | 1 | 1 | 1 |
| A21 | 8.2 | 20.7 | F | M | CAD | 50.1 | SB | 6.9 | 29.2 | 2 | 2 | 2 | 2 | 1 | 2 | 1 | 1 | 1 |
| A22 | 4.2 | 9.7 | M | F | LRD | 31.0 | SF | 5.2 | 28.0 | 2 | 1 | 1 | 2 | 1 | 2 | 1 | 1 | 1 |
| A23 | 2.1 | 17.3 | M | F | CAD | 34.0 | SB | 9.1 | 38.4 | 2 | 2 | 2 | 2 | 2 | 2 | 1 | 1 | 1 |
| A25 | 5.5 | 9.7 | M | F | LRD | 31.0 | SF | 2.2 | 26.4 | 2 | 1 | 2 | 2 | 1 | 2 | 1 | 1 | 1 |
| A26 | 7.0 | 9.3 | M | F | CAD | 9.1 | SF | 4.3 | 35.5 | 2 | 2 | 2 | 2 | 1 | 2 | 1 | 1 | 1 |
| A30 | 25.0 | 11.6 | F | F | CAD | 16.0 | SF | 6.0 | 37.5 | 2 | 2 | 2 | 2 | 1 | 2 | 1 | 1 | 1 |
| A31 | 51.4 | 12.1 | M | M | LRD | 34.1 | SB | 7.3 | 37.2 | 2 | 2 | 2 | 2 | 1 | 2 | 1 | 1 | 1 |
| A38 | 6.1 | 11.8 | F | NA | CAD | 26.8 | SB | 9.7 | 36.0 | 2 | 2 | 2 | 1 | 1 | 2 | 1 | 1 | 1 |
| A48 | 6.3 | 1.6 | F | F | LRD | 42.0 | SB | 6.0 | 29.6 | 2 | 2 | 2 | 2 | 2 | 2 | 1 | 1 | 1 |
| A49 | 28.2 | 17.0 | M | M | LRD | 36.3 | SF | 13.9 | 37.5 | 2 | 2 | 2 | 2 | 2 | 2 | 1 | 1 | 1 |
| A50 | 69.8 | 12.2 | M | F | LRD | 41.0 | SB | 4.6 | 35.2 | 2 | 2 | 2 | 2 | 1 | 2 | 2 | 2 | 2 |
| A51 | 56.9 | 11.8 | F | M | LRD | 37.7 | SB | 12.5 | 35.1 | 2 | 2 | 2 | 2 | 1 | 2 | 2 | 2 | 2 |
| A52 | 5.6 | 1.3 | F | F | LRD | 32.2 | SF | 6.3 | 27.2 | 2 | 1 | 2 | 2 | 1 | 2 | 1 | 1 | 1 |
| A53 | 32.6 | 14.9 | M | F | LRD | 44.0 | SB | 8.0 | 40.9 | 2 | 2 | 2 | 2 | 1 | 2 | 1 | 1 | 1 |

FIG. 11 (CONT.)

| | | | | | | | | | | | | | | | | | | |
|---|---|---|---|---|---|---|---|---|---|---|---|---|---|---|---|---|---|---|
| A54 | 0.4 | 3.3 | M | F | CAD | 33.1 | SF | 16.9 | 31.2 | 2 | 1 | 2 | 1 | 2 | 2 | 1 | 1 | 1 |
| A55 | 0.1 | 9.1 | M | M | CAD | 16.0 | SF | 6.1 | 27.6 | 2 | 2 | 2 | 2 | 2 | 2 | 1 | 1 | 1 |
| A56 | 0.4 | 16.0 | F | F | CAD | 29.0 | SF | 5.6 | 20.8 | 2 | 2 | 2 | 2 | 2 | 2 | 1 | 1 | 1 |
| A57 | 45.5 | 10.4 | M | M | LRD | 44.7 | SF | 6.8 | 29.0 | 2 | 2 | 2 | 2 | 1 | 2 | 1 | 1 | 1 |
| A58 | 0.2 | 17.3 | F | M | CAD | 14.0 | SB | 6.1 | 28.2 | 2 | 2 | 2 | 2 | 2 | 2 | 1 | 1 | 1 |
| A59 | 3.7 | 3.2 | M | M | CAD | 5.0 | SB | 3.0 | 34.4 | 2 | 2 | 2 | 2 | 2 | 2 | 1 | 1 | 1 |
| A60 | 47.0 | 10.4 | M | M | LRD | 44.7 | SF | 5.4 | 24.3 | 2 | 2 | 2 | 2 | 1 | 2 | 1 | 1 | 1 |
| A61 | 4.2 | 3.2 | M | M | CAD | 5.0 | SB | | | 2 | 2 | 2 | 2 | 2 | 2 | 1 | 1 | 1 |
| A62 | 6.0 | 17.1 | M | F | CAD | 31.0 | SB | 8.8 | 44.0 | 2 | 2 | 2 | 2 | 2 | 2 | 1 | 1 | 1 |
| A63 | 11.7 | 6.4 | M | F | CAD | 16.0 | SF | 7.3 | 36.4 | 2 | 2 | 2 | 2 | 2 | 2 | 1 | 1 | 1 |
| A64 | 1.9 | 15.2 | M | M | CAD | 22.0 | SB | 3.6 | 33.1 | 2 | 2 | 2 | 2 | 2 | 2 | 1 | 1 | 1 |
| A65 | 5.5 | 15.7 | M | M | CAD | 23.0 | SB | | | 2 | 2 | 2 | 2 | 2 | 2 | 1 | 1 | 1 |
| A66 | 0.9 | 15.8 | M | M | CAD | 28.0 | SF | 5.5 | 23.8 | 2 | 2 | 2 | 2 | 2 | 2 | 1 | 1 | 1 |
| A67 | 6.2 | 17.7 | F | M | CAD | 18.0 | SF | 8.9 | 36.8 | 2 | 2 | 2 | 2 | 2 | 2 | 1 | 1 | 1 |
| A68 | 5.6 | 4.6 | M | F | CAD | 28.0 | SF | 9.9 | 33.4 | 2 | 1 | 2 | 2 | 2 | 2 | 1 | 1 | 1 |
| A69 | 6.2 | 17.1 | F | M | LRD | 37.0 | SF | 2.4 | 27.6 | 2 | 2 | 2 | 2 | 2 | 2 | 1 | 1 | 1 |
| A70 | 8.8 | 17.0 | M | M | LRD | 39.0 | SF | 6.4 | 30.1 | 2 | 2 | 2 | 2 | 1 | 2 | 1 | 1 | 1 |
| A71 | 64.6 | 12.2 | M | F | LRD | 41.0 | SB | 3.8 | 34.6 | 2 | 2 | 2 | 2 | 1 | 2 | 2 | 2 | 2 |
| A72 | 23.9 | 12.1 | M | M | LRD | 34.1 | SB | 11.1 | 36.3 | 2 | 2 | 2 | 2 | 1 | 2 | 1 | 1 | 1 |
| A73 | 59.7 | 11.8 | F | M | LRD | 37.7 | SB | 10.4 | 30.6 | 2 | 2 | 2 | 2 | 1 | 2 | 2 | 2 | 2 |
| A75 | 9.0 | 20.7 | F | M | CAD | 50.1 | SB | 5.4 | 27.3 | 2 | 2 | 2 | 2 | 1 | 2 | 1 | 1 | 1 |
| A76 | 8.6 | 9.3 | M | F | CAD | 9.1 | SF | 6.5 | 38.6 | 2 | 1 | 1 | 2 | 1 | 2 | 1 | 1 | 1 |
| A77 | 11.6 | 1.6 | F | F | LRD | 42.0 | SB | 8.1 | 30.1 | 2 | 2 | 2 | 2 | 2 | 2 | 1 | 1 | 1 |
| A78 | 10.8 | 15.5 | M | F | LRD | 19.0 | SF | 8.8 | 34.7 | 2 | 2 | 2 | 2 | 1 | 2 | 1 | 1 | 1 |
| A79 | 2.7 | 2.8 | M | M | LRD | 48.0 | SF | 4.4 | 25.9 | 2 | 2 | 2 | 2 | 2 | 2 | 1 | 1 | 1 |
| A80 | 11.6 | 9.3 | M | F | CAD | 9.1 | SF | 5.1 | 36.7 | 2 | 1 | 1 | 2 | 1 | 2 | 1 | 1 | 1 |
| A81 | 17.9 | 20.7 | F | M | LRD | 50.1 | SB | 9.1 | 36.1 | 2 | 2 | 2 | 2 | 1 | 1 | 1 | 1 | 1 |
| A82 | 58.0 | 4.5 | M | M | LRD | 38.0 | SF | 5.9 | 24.1 | 2 | 2 | 2 | 2 | 1 | 2 | 1 | 1 | 1 |
| A83 | 0.2 | 16.8 | M | F | LRD | 49.0 | SF | 5.0 | 42.1 | 2 | 2 | 2 | 2 | 2 | 2 | 1 | 1 | 1 |
| A84 | 0.2 | 14.3 | M | M | LRD | 36.0 | SF | 5.6 | 28.3 | 2 | 2 | 2 | 2 | 2 | 2 | 1 | 1 | 1 |
| A85 | 0.9 | 17.3 | F | M | CAD | 14.0 | SB | 3.0 | 19.9 | 2 | 2 | 2 | 2 | 2 | 2 | 1 | 1 | 1 |
| A86 | 13.3 | 6.9 | M | F | LRD | 43.0 | SF | 8.0 | 32.8 | 2 | 1 | 2 | 2 | 1 | 2 | 1 | 1 | 1 |

FIG. 11 (CONT.)

| | | | | | | | | | | | | | | | | | | |
|---|---|---|---|---|---|---|---|---|---|---|---|---|---|---|---|---|---|---|
| A87 | 1.6 | 14.8 | F | F | LRD | 38.0 | SB | 10.1 | 31.0 | 2 | 2 | 2 | 2 | 2 | 2 | 1 | 1 | 1 |
| A88 | 1.5 | 14.3 | M | M | LRD | 36.0 | SF | 3.3 | 24.1 | 2 | 2 | 2 | 2 | 2 | 2 | 1 | 1 | 1 |
| A89 | 51.0 | 12.1 | M | M | LRD | 34.1 | SB | 8.6 | 42.8 | 2 | 2 | 2 | 2 | 1 | 2 | 1 | 1 | 1 |
| A90 | 5.6 | 14.9 | M | F | CAD | 17.0 | SB | 5.8 | 35.9 | 2 | 2 | 2 | 2 | 2 | 2 | 1 | 1 | 1 |
| A91 | 0.3 | 16.3 | M | F | LRD | 43.0 | SF | 12.0 | 34.4 | 2 | 2 | 2 | 2 | 2 | 2 | 1 | 1 | 1 |
| A92 | 6.1 | 11.1 | F | M | CAD | 16.0 | SB | | | 2 | 2 | 2 | 2 | 2 | 2 | 1 | 1 | 1 |
| A93 | 33.0 | 8.0 | F | F | CAD | 4.0 | SB | | | 2 | 1 | 2 | 2 | 1 | 2 | 1 | 1 | 1 |
| A94 | 10.7 | 17.6 | M | M | CAD | 37.1 | SF | 9.1 | 29.8 | 2 | 2 | 2 | 2 | 1 | 2 | 1 | 1 | 1 |
| A95 | 5.6 | 10.8 | M | F | LRD | 33.0 | SF | 13.3 | 39.7 | 2 | 2 | 2 | 2 | 2 | 2 | 1 | 1 | 1 |
| A96 | 3.5 | 14.3 | M | F | LRD | 44.0 | SF | 4.9 | 31.2 | 2 | 2 | 2 | 2 | 1 | 2 | 1 | 1 | 1 |
| A97 | 6.1 | 3.6 | M | M | CAD | 15.0 | SF | 7.3 | 25.4 | 2 | 1 | 2 | 1 | 1 | 2 | 1 | 1 | 1 |
| A98 | 15.8 | 17.6 | M | M | CAD | 37.1 | SF | 9.5 | 27.5 | 2 | 2 | 2 | 2 | 1 | 2 | 1 | 1 | 1 |
| A99 | 5.2 | 4.5 | F | F | CAD | 26.0 | SF | 9.6 | 22.6 | 2 | 2 | 2 | 2 | 2 | 2 | 1 | 1 | 1 |
| A100 | 6.3 | 16.5 | F | M | CAD | 26.0 | SB | 6.0 | 35.0 | 2 | 2 | 2 | 2 | 2 | 2 | 1 | 1 | 1 |
| A101 | 14.2 | 19.7 | F | M | CAD | 17.0 | SB | | | 2 | 2 | 2 | 2 | 2 | 2 | 1 | 1 | 1 |
| S100 | 3.0 | 17.6 | M | M | CRD | 37.0 | SF | 4.8 | 41.3 | 2 | 2 | 2 | 2 | 1 | 2 | 1 | 1 | 1 |
| S101 | 3.0 | 18.8 | F | F | CAD | 19.0 | SB | 8.2 | 38.6 | 2 | 2 | 2 | 2 | 2 | 2 | 1 | 1 | 1 |
| S102 | 6.0 | 15.8 | F | M | LRD | 38.5 | SB | 6.8 | 37.4 | 2 | 2 | 2 | 2 | 2 | 2 | 1 | 1 | 1 |
| S103 | 5.8 | 19.0 | M | M | LRD | 47.0 | SF | 6.9 | 39.8 | 2 | 2 | 2 | 2 | 2 | 2 | 1 | 1 | 1 |
| S104 | 12.0 | 16.6 | M | F | LRD | 47.1 | SF | 6.1 | 36.3 | 2 | 2 | 2 | 2 | 2 | 2 | 1 | 1 | 1 |
| S105 | 5.8 | 17.4 | M | F | CAD | 20.0 | SB | 3.1 | 25.5 | 2 | 2 | 2 | 2 | 2 | 2 | 1 | 1 | 1 |
| S106 | 12.0 | 14.6 | M | M | LRD | 43.0 | SB | 7.0 | 39.7 | 2 | 2 | 2 | 2 | 2 | 2 | 1 | 1 | 1 |
| S107 | 5.8 | 18.7 | F | M | CAD | 14.0 | SB | 5.1 | 40.0 | 2 | 2 | 2 | 2 | 2 | 2 | 1 | 1 | 1 |
| S108 | 2.9 | 1.0 | F | M | LRD | 28.1 | SF | 3.8 | 27.6 | 2 | 1 | 2 | 2 | 2 | 2 | 1 | 1 | 1 |
| S15 | 41.5 | 16.4 | M | F | LRD | 41.4 | SB | 10.5 | 39.5 | 2 | 2 | 2 | 2 | 1 | 2 | 2 | 2 | 2 |
| S19 | 3.3 | 2.0 | M | M | LRD | 33.8 | SF | | | 2 | 2 | 2 | 2 | 2 | 2 | 1 | 1 | 1 |
| S22 | 6.0 | 17.2 | M | F | LRD | 29.0 | SB | 7.0 | 38.6 | 2 | 2 | 2 | 2 | 1 | 2 | 1 | 1 | 1 |
| S23 | 4.8 | 10.9 | F | F | LRD | 31.3 | SB | 5.3 | 32.9 | 2 | 2 | 2 | 2 | 2 | 2 | 1 | 1 | 1 |
| S24 | 6.8 | 1.2 | F | M | LRD | 27.1 | SF | 5.6 | 34.3 | 2 | 2 | 2 | 2 | 2 | 2 | 1 | 1 | 1 |
| S30 | 2.8 | 1.3 | F | F | LRD | 32.2 | SF | 9.9 | 38.5 | 2 | 1 | 2 | 2 | 1 | 2 | 1 | 1 | 1 |
| S30 | 2.8 | 1.3 | F | F | LRD | 32.2 | SF | 9.9 | 38.5 | 2 | 1 | 2 | 2 | 1 | 2 | 1 | 1 | 1 |
| S31 | 94.5 | 10.1 | M | M | LRD | 34.2 | SB | 8.0 | 42.7 | 2 | 2 | 2 | 2 | 1 | 2 | 2 | 2 | 2 |
| S31 | 94.5 | 10.1 | M | M | LRD | 34.2 | SB | 8.0 | 42.7 | 2 | 2 | 2 | 2 | 1 | 2 | 2 | 2 | 2 |

FIG. 11 (CONT.)

| | | | | | | | | | | | | | | | | | | |
|---|---|---|---|---|---|---|---|---|---|---|---|---|---|---|---|---|---|---|
| S32 | 3.1 | 1.6 | F | F | LRD | 42.0 | SB | 5.1 | 26.1 | 2 | 1 | 2 | 2 | 2 | 2 | 1 | 1 | 1 |
| S32 | 3.1 | 1.6 | F | F | LRD | 42.0 | SB | 5.1 | 26.1 | 2 | 2 | 2 | 2 | 2 | 2 | 1 | 1 | 1 |
| S33 | 6.2 | 20.7 | F | M | CAD | 50.1 | SB | 5.9 | 38.7 | 2 | 2 | 2 | 2 | 1 | 2 | 1 | 1 | 1 |
| S33 | 6.2 | 20.7 | F | M | CAD | 50.1 | SB | 5.9 | 38.7 | 2 | 2 | 2 | 2 | 1 | 2 | 1 | 1 | 1 |
| S35 | 24.1 | 16.0 | M | F | LRD | 40.1 | SF | 6.2 | 37.5 | 2 | 2 | 2 | 2 | 2 | 2 | 1 | 1 | 1 |
| S36 | 31.4 | 3.3 | M | M | LRD | 19.8 | SF | 12.0 | 37.8 | 2 | 2 | 2 | 2 | 1 | 2 | 1 | 1 | 1 |
| S37 | 6.8 | 16.7 | M | M | LRD | 37.0 | SB | 6.0 | 30.4 | 2 | 2 | 2 | 2 | 2 | 2 | 1 | 1 | 1 |
| S39 | 6.0 | 1.4 | M | M | LRD | 28.0 | SB | 12.0 | 37.5 | 2 | 2 | 2 | 2 | 2 | 2 | 1 | 1 | 1 |
| S41 | 23.0 | 3.6 | M | F | LRD | 30.8 | SF | 5.5 | 35.8 | 2 | 2 | 2 | 2 | 2 | 2 | 1 | 1 | 1 |
| S42 | 5.5 | 6.4 | M | F | CAD | 16.0 | SF | 2.9 | 29.0 | 2 | 2 | 2 | 2 | 2 | 2 | 1 | 1 | 1 |
| S43 | 5.4 | 5.8 | F | M | LRD | 44.0 | SB | 3.1 | 30.4 | 2 | 2 | 2 | 2 | 2 | 2 | 1 | 1 | 1 |
| S44 | 6.1 | 20.0 | F | F | CAD | 24.0 | SF | 6.4 | 34.1 | 2 | 2 | 2 | 2 | 2 | 2 | 1 | 1 | 1 |
| S46 | 2.4 | 3.6 | M | M | CAD | 14.8 | SF | 4.9 | 27.0 | 1 | 1 | 1 | 1 | 2 | 2 | 1 | 1 | 1 |
| S47 | 6.1 | 8.1 | F | M | CAD | 15.0 | SF | 7.4 | 31.4 | 2 | 2 | 2 | 2 | 2 | 2 | 1 | 1 | 1 |
| S57 | 12.0 | 18.0 | M | F | LRD | 38.8 | SF | 10.2 | 50.3 | 2 | 2 | 2 | 2 | 2 | 2 | 1 | 1 | 1 |
| S58 | 23.7 | 11.7 | F | M | LRD | 48.1 | SF | 11.8 | 34.9 | 2 | 2 | 2 | 2 | 2 | 2 | 1 | 1 | 1 |
| S59 | 6.2 | 18.6 | M | M | CAD | 25.1 | SF | 3.9 | 45.4 | 2 | 2 | 2 | 2 | 1 | 2 | 1 | 1 | 1 |
| S60 | 6.0 | 17.8 | M | M | LRD | 21.0 | SF | 4.0 | 37.4 | 2 | 2 | 2 | 2 | 2 | 2 | 1 | 1 | 1 |
| S61 | 24.1 | 2.2 | F | F | LRD | 27.0 | SB | 8.9 | 35.8 | 2 | 1 | 2 | 2 | 2 | 2 | 1 | 1 | 1 |
| S62 | 12.0 | 17.8 | M | M | LRD | 21.0 | SF | 4.2 | 39.5 | 2 | 2 | 2 | 2 | 2 | 2 | 1 | 1 | 1 |
| S63 | 6.1 | 10.0 | M | M | CAD | 18.0 | SB | 5.2 | 35.2 | 2 | 2 | 2 | 2 | 2 | 2 | 1 | 1 | 1 |
| S64 | 6.0 | 15.8 | F | M | LRD | 38.5 | SB | 6.8 | 37.4 | 2 | 2 | 2 | 2 | 2 | 2 | 1 | 1 | 1 |
| S65 | 13.4 | 18.4 | M | F | LRD | 50.6 | SF | 7.1 | 39.1 | 2 | 2 | 2 | 2 | 2 | 2 | 1 | 1 | 1 |
| S66 | 5.5 | 2.5 | F | F | LRD | 54.0 | SB | 5.1 | 33.0 | 2 | 2 | 2 | 2 | 2 | 2 | 1 | 1 | 1 |
| S67 | 13.0 | 9.2 | M | F | LRD | 30.4 | SF | 6.8 | 33.5 | 2 | 2 | 2 | 2 | 2 | 2 | 1 | 1 | 1 |
| S68 | 5.9 | 7.4 | M | F | CAD | 32.0 | SF | 6.1 | 35.5 | 2 | 2 | 2 | 2 | 2 | 2 | 1 | 1 | 1 |
| S69 | 5.4 | 15.2 | F | M | LRD | 35.0 | SB | 7.4 | 33.1 | 2 | 2 | 2 | 2 | 2 | 2 | 1 | 1 | 1 |
| S70 | 6.1 | 13.8 | F | F | CAD | 20.0 | SB | 2.9 | 32.0 | 2 | 2 | 2 | 2 | 2 | 2 | 1 | 1 | 1 |
| S71 | 5.8 | 15.8 | F | F | LRD | 36.0 | SF | 1.7 | 28.8 | 2 | 2 | 2 | 2 | 2 | 2 | 1 | 1 | 1 |
| S72 | 6.0 | 12.5 | M | M | LRD | 21.0 | SF | 5.8 | 34.8 | 2 | 2 | 2 | 2 | 2 | 2 | 1 | 1 | 1 |
| S73 | 6.0 | 16.5 | M | F | CAD | 28.0 | SB | 10.4 | 28.9 | 2 | 2 | 2 | 2 | 2 | 2 | 1 | 1 | 1 |
| S74 | 5.9 | 18.0 | F | F | CAD | 25.0 | SF | 3.4 | 34.3 | 2 | 2 | 2 | 2 | 2 | 2 | 1 | 1 | 1 |

FIG. 11 (CONT.)

| | | | | | | | | | | | | | | | | | |
|---|---|---|---|---|---|---|---|---|---|---|---|---|---|---|---|---|---|
| S75 | 6.0 | 9.8 | M | F | CAD | 18.0 | SB | 4.0 | 32.4 | 2 | 2 | 2 | 2 | 2 | 2 | 1 | 1 | 1 |
| S76 | 5.9 | 16.3 | F | M | CAD | 24.0 | SF | 3.1 | 37.1 | 2 | 2 | 2 | 2 | 2 | 2 | 1 | 1 | 1 |
| S77 | 3.0 | 10.4 | F | M | LRD | 36.0 | SF | 5.0 | 39.0 | 2 | 2 | 2 | 2 | 2 | 2 | 1 | 1 | 1 |
| S78 | 3.1 | 20.2 | M | F | LRD | 51.0 | SF | 2.9 | 34.6 | 2 | 2 | 2 | 2 | 1 | 2 | 1 | 1 | 1 |
| S79 | 5.8 | 20.3 | F | M | CAD | 24.0 | SF | | | 2 | 2 | 2 | 2 | 2 | 2 | 1 | 1 | 1 |
| S80 | 6.0 | 11.7 | F | M | LRD | 48.0 | SF | 5.2 | 30.1 | 2 | 2 | 2 | 1 | 2 | 2 | 1 | 1 | 1 |
| S81 | 2.9 | 16.0 | M | F | LRD | 40.1 | SF | 2.8 | 31.2 | 2 | 2 | 2 | 2 | 2 | 2 | 1 | 1 | 1 |
| S82 | 2.6 | 14.7 | M | M | LRD | 39.8 | SF | 4.6 | 36.0 | 2 | 2 | 2 | 2 | 2 | 2 | 1 | 1 | 1 |
| S83 | 12.9 | 8.0 | F | F | LRD | 44.1 | SF | 9.3 | 40.8 | 2 | 2 | 2 | 2 | 2 | 2 | 1 | 1 | 1 |
| S84 | 12.1 | 16.0 | M | F | LRD | 40.1 | SF | 7.2 | 43.5 | 2 | 2 | 2 | 2 | 2 | 2 | 1 | 1 | 1 |
| S85 | 3.5 | 18.9 | M | F | LRD | 42.8 | SF | 4.7 | 38.7 | 2 | 2 | 2 | 2 | 2 | 2 | 1 | 1 | 1 |
| S86 | 6.0 | 18.9 | F | F | LRD | 42.8 | SF | 5.1 | 42.0 | 2 | 2 | 2 | 2 | 2 | 2 | 1 | 1 | 1 |
| S87 | 1.2 | 17.8 | M | F | CAD | 42.3 | SB | 5.3 | 39.3 | 2 | 2 | 2 | 2 | 2 | 2 | 1 | 1 | 1 |
| S88 | 2.8 | 20.7 | F | M | LRD | 50.1 | SB | 10.0 | 40.3 | 2 | 2 | 2 | 2 | 1 | 1 | 1 | 1 | 1 |
| S89 | 27.7 | 15.5 | F | F | LRD | 42.0 | SB | 8.1 | 33.8 | 2 | 2 | 2 | 2 | 2 | 2 | 1 | 1 | 1 |
| S90 | 3.7 | 18.6 | M | M | CAD | 25.1 | SF | 4.7 | 40.7 | 2 | 2 | 2 | 2 | 1 | 2 | 1 | 1 | 1 |
| S91 | 13.2 | 18.9 | M | F | LRD | 42.8 | SF | 4.4 | 46.0 | 2 | 2 | 2 | 2 | 2 | 2 | 1 | 1 | 1 |
| S92 | 5.9 | 18.2 | F | 0 | CAD | 14.2 | SF | | | 2 | 2 | 2 | 2 | 1 | 2 | 1 | 1 | 1 |
| S93 | 2.8 | 1.8 | M | M | LRD | 22.0 | SF | 6.2 | 34.7 | 2 | 1 | 2 | 1 | 1 | 2 | 1 | 1 | 1 |
| S94 | 2.4 | 18.4 | M | F | LRD | 50.6 | SF | 6.8 | 35.8 | 2 | 2 | 2 | 2 | 2 | 2 | 1 | 1 | 1 |
| S95 | 3.0 | 6.9 | M | F | LRD | 43.0 | SF | 5.0 | 21.2 | 2 | 2 | 2 | 2 | 1 | 2 | 1 | 1 | 1 |
| S96 | 2.7 | 16.6 | M | F | LRD | 47.0 | SF | 6.4 | 32.0 | 2 | 2 | 2 | 2 | 2 | 2 | 1 | 1 | 1 |
| S97 | 3.0 | 14.5 | F | M | LRD | 47.0 | SF | 6.0 | 30.0 | 2 | 2 | 2 | 2 | 2 | 2 | 1 | 1 | 1 |
| S98 | 0.2 | 18.8 | F | M | CRD | 19.0 | SB | 8.2 | 20.5 | 2 | 2 | 2 | 2 | 2 | 2 | 1 | 1 | 1 |
| S99 | 12.0 | 6.9 | F | F | LRD | 37.8 | SB | 10.0 | 32.8 | 2 | 2 | 2 | 2 | 2 | 2 | 1 | 1 | 1 |

FIG. 12

| | post transplant time | Recipient Age | Recipient Sex | Donor Sex | Donor Source | Donor Age | SF or SB | CMV | EBV |
|---|---|---|---|---|---|---|---|---|---|
| CFLAR | r=0.13<br>p=0.13 | r=0.02<br>p=0.81 | r=−0.03<br>p=0.72 | r=−0.08<br>p=0.34 | r=−0.06<br>p=0.45 | r=−0.05<br>p=0.55 | r=0.08<br>p=0.34 | r=0.05<br>p=0.54 | r=0.04<br>p=0.63 |
| DUSP1 | r=0.15<br>p=0.09 | r=−0.06<br>p=0.5 | r=−0.09<br>p=0.32 | r=−0.12<br>p=0.18 | r=0.16<br>p=0.06 | r=−0.15<br>p=0.07 | r=0<br>p=0.98 | r=−0.01<br>p=0.94 | r=−0.11<br>p=0.19 |
| IFNGR1 | r=0.15<br>p=0.08 | r=0.05<br>p=0.58 | r=−0.08<br>p=0.32 | r=0.04<br>p=0.63 | r=−0.05<br>p=0.55 | r=0.01<br>p=0.9 | r=0.07<br>p=0.39 | r=0.05<br>p=0.56 | r=−0.01<br>p=0.89 |
| ITGAX | r=0.15<br>p=0.09 | r=0.01<br>p=0.92 | r=−0.11<br>p=0.2 | r=−0.15<br>p=0.07 | r=−0.01<br>p=0.89 | r=−0.02<br>p=0.85 | r=−0.08<br>p=0.38 | r=0.05<br>p=0.56 | r=0.03<br>p=0.69 |
| MAPK9 | r=−0.09<br>p=0.31 | r=−0.06<br>p=0.48 | r=0.13<br>p=0.13 | r=0.06<br>p=0.48 | r=−0.08<br>p=0.36 | r=0<br>p=0.96 | r=−0.15<br>p=0.08 | r=−0.13<br>p=0.13 | r=−0.01<br>p=0.94 |
| NKTR | r=−0.07<br>p=0.44 | r=0.16<br>p=0.06 | r=0.01<br>p=0.88 | r=0.12<br>p=0.16 | r=−0.06<br>p=0.48 | r=0.11<br>p=0.19 | r=−0.12<br>p=0.15 | r=−0.07<br>p=0.39 | r=0.07<br>p=0.42 |
| PBEF1 | r=0.03<br>p=0.69 | r=0.04<br>p=0.64 | r=−0.08<br>p=0.36 | r=0.05<br>p=0.6 | r=−0.04<br>p=0.62 | r=0.02<br>p=0.84 | r=0.02<br>p=0.84 | r=0.07<br>p=0.43 | r=0<br>p=0.98 |
| PSEN1 | r=0.29<br>p=0 | r=0<br>p=0.98 | r=−0.09<br>p=0.32 | r=0<br>p=0.96 | r=−0.12<br>p=0.15 | r=0.03<br>p=0.73 | r=0.14<br>p=0.11 | r=0.05<br>p=0.55 | r=0.02<br>p=0.83 |
| RNG130 | r=0.1<br>p=0.24 | r=0.05<br>p=0.58 | r=−0.02<br>p=0.86 | r=−0.08<br>p=0.37 | r=0.03<br>p=0.72 | r=−0.01<br>p=0.88 | r=−0.08<br>p=0.33 | r=−0.02<br>p=0.8 | r=−0.02<br>p=0.78 |
| RYBP | r=0.02<br>p=0.79 | r=−0.01<br>p=0.89 | r=−0.07<br>p=0.4 | r=−0.1<br>p=0.27 | r=0.18<br>p=0.03 | r=−0.15<br>p=0.08 | r=0.04<br>p=0.66 | r=0.03<br>p=0.76 | r=0.07<br>p=0.4 |

FIG. 12 (CONT.)

| BKV | bacteria Infection | DSA | PRA | Induction | FK or CSA | MMF or AZA | WBC | HCT |
|---|---|---|---|---|---|---|---|---|
| r=0.03 p=0.71 | r=0.01 p=0.91 | r=−0.22 p=0.01 | r=0.03 p=0.76 | r=0.09 p=0.28 | r=0.09 p=0.28 | r=0.09 p=0.28 | r=0.16 p=0.07 | r=−0.1 p=0.25 |
| r=−0.21 p=0.01 | r=−0.03 p=0.71 | r=−0.24 p=0 | r=0.07 p=0.4 | r=0.09 p=0.3 | r=0.09 p=0.3 | r=0.09 p=0.3 | r=0.14 p=0.11 | r=−0.18 p=0.04 |
| r=0 p=0.99 | r=0 p=0.99 | r=−0.25 p=0 | r=0.03 p=0.73 | r=0.04 p=0.61 | r=0.04 p=0.61 | r=0.04 p=0.61 | r=0.17 p=0.04 | r=0.02 p=0.81 |
| r=−0.02 p=0.8 | r=0.05 p=0.57 | r=−0.07 p=0.42 | r=−0.11 p=0.18 | r=0.02 p=0.81 | r=0.02 p=0.81 | r=0.02 p=0.81 | r=0.15 p=0.08 | r=−0.1 p=0.25 |
| r=0.03 p=0.71 | r=0.06 p=0.51 | r=0.14 p=0.1 | r=0.02 p=0.86 | r=−0.08 p=0.35 | r=−0.08 p=0.35 | r=−0.08 p=0.35 | r=0.13 p=0.13 | r=0.14 p=0.11 |
| r=0.01 p=0.88 | r=0.04 p=0.61 | r=0.15 p=0.08 | r=0.04 p=0.64 | r=−0.06 p=0.47 | r=−0.06 p=0.47 | r=−0.06 p=0.47 | r=−0.1 p=0.27 | r=0.27 p=0 |
| r=0 p=0.98 | r=0.05 p=0.58 | r=−0.26 p=0 | r=−0.05 p=0.54 | r=−0.01 p=0.87 | r=−0.01 p=0.87 | r=−0.01 p=0.87 | r=0.12 p=0.16 | r=−0.08 p=0.33 |
| r=−0.02 p=0.84 | r=0.03 p=0.71 | r=−0.27 p=0 | r=−0.09 p=0.28 | r=0.2 p=0.02 | r=0.2 p=0.02 | r=0.2 p=0.02 | r=0.18 p=0.03 | r=−0.05 p=0.53 |
| r=0.02 p=0.82 | r=−0.04 p=0.61 | r=−0.04 p=0.63 | r=0.02 p=0.82 | r=0.05 p=0.52 | r=0.05 p=0.52 | r=0.05 p=0.52 | r=0.14 p=0.09 | r=−0.09 p=0.27 |
| r=0.04 p=0.61 | r=0.03 p=0.69 | r=0.02 p=0.79 | r=0.02 p=0.79 | r=−0.02 p=0.84 | r=−0.02 p=0.84 | r=−0.02 p=0.84 | r=0.09 p=0.31 | r=−0.11 p=0.19 |

Correlation Between Biopsy Banff Grade, Peritubular C4d positivity and Humoral vs Cellular AR, and the AR Prediction Probability

| Unique Sample IDs for Validation Set 1 and Validation Set 2 | AR probability | Banff score | BL&1A=1; >1A=2 | C4d (1=yes, 2=no) | Humoral(1)/Cellular(2) |
|---|---|---|---|---|---|
| A49 | 100.0% | Borderline | 1 | NA | NA |
| A50 | 100.0% | Borderline | 1 | 2 | 2 |
| A51 | 100.0% | 1B | 2 | 2 | 2 |
| A52 | 100.0% | 1A | 1 | 2 | 2 |
| A53 | 99.6% | 1A | 1 | 2 | 2 |
| A54 | 100.0% | Borderline | 1 | 2 | 2 |
| A55 | 99.9% | IA | 1 | 2 | 2 |
| A56 | 99.6% | IA | 1 | 1 | 2 |
| A57 | 100.0% | 1A | 1 | 2 | 2 |
| A58 | 100.0% | IB | 2 | 2 | 2 |
| A59 | 100.0% | IA | 1 | 2 | 2 |
| A60 | 100.0% | Borderline | 1 | 1 | 1 |
| A61 | 99.8% | IIB | 2 | 1 | 1 |
| A62 | 100.0% | Borderline | 1 | 2 | 2 |
| A63 | 100.0% | Borderline | 1 | 2 | 2 |
| A64 | 100.0% | Borderline | 1 | 2 | 2 |
| A65 | 100.0% | IA | 1 | 2 | 2 |
| A66 | 99.8% | Borderline | 1 | 2 | 2 |
| A67 | 100.0% | IA | 1 | 2 | 2 |
| A68 | 99.9% | 1A | 1 | 2 | 2 |
| A69 | 100.0% | IA | 1 | 2 | 2 |
| A70 | 99.9% | IIA | 2 | 2 | 2 |
| A71 | 97.6% | Borderline | 1 | 2 | 2 |
| A72 | 98.6% | Borderline | 1 | 1 | 1 |
| A73 | 100.0% | Borderline | 1 | 2 | 2 |
| A74 | 100.0% | 1A | 1 | 2 | 2 |
| A75 | 98.9% | 1B | 2 | 1 | 2 |

FIG. 14

| | | | | | |
|---|---|---|---|---|---|
| A76 | 100.0% | 1A | 1 | 1 | 1 |
| A77 | 100.0% | 1B | 2 | 2 | 2 |
| A78 | 100.0% | Borderline | 1 | 2 | 2 |
| A79 | 100.0% | Borderline | 1 | 2 | 2 |
| A80 | 100.0% | 1B | 2 | 2 | 2 |
| A81 | 100.0% | Borderline | 1 | 1 | 1 |
| A82 | 100.0% | Borderline | 1 | 2 | 2 |
| A83 | 100.0% | IIA | 2 | 2 | 2 |
| A84 | 100.0% | Borderline | 1 | 2 | 2 |
| A85 | 100.0% | Borderline | 1 | 2 | 2 |
| A86 | 100.0% | IB | 2 | 2 | 2 |
| A87 | 100.0% | IIA | 2 | 2 | 2 |
| A88 | 100.0% | Borderline | 1 | 2 | 2 |
| A89 | 100.0% | IIA | 2 | 2 | 2 |
| A90 | 99.8% | IIA | 2 | NA | NA |
| A91 | 100.0% | Borderline | 1 | 2 | 2 |
| A92 | 99% | Borderline | 1 | 2 | 2 |
| A93 | 100.0% | IIB | 2 | 1 | 1 |
| A94 | 100.0% | 1A | 1 | 1 | 1 |
| A95 | 99.9% | Borderline | 1 | 2 | 2 |
| A96 | 100.0% | 1B | 2 | 2 | 2 |
| A97 | 100.0% | 1B | 2 | 2 | 2 |
| A98 | 99.9% | Borderline | 1 | 2 | 2 |
| A99 | 97.2% | IB | 2 | NA | NA |
| A100 | 98.3% | IIB | 2 | NA | NA |
| A101 | 100.0% | IB | 2 | NA | NA |
| Correlation Coefficient R (AR probability vs Validation Set 1& Set 2) | | | −0.12674736 | 0.2122 | 0.0703 |

FIG. 14 (CONT.)

Prediction Probability of AR in Paired Samples Collected Within 6 Months Before and After the AR episode

| Sample Collection Time pre and postAR | AR probability | std. error | Calculated Schwartz Clearance (CrCL) | std. error | number of samples |
|---|---|---|---|---|---|
| −3 to −6 (preAR) | 68% | 0.09491447 | 98.5 | 7.2223806 | 16 |
| 0 to −3 (preAR) | 92% | 0.04205993 | 81.3 | 7.2050639 | 11 |
| 0 (at AR) | 93% | 0.02008312 | 82.8 | 5.6887337 | 40 |
| 0 to 3 (postAR) | 47% | 0.10926877 | 72.9 | 9.6104671 | 12 |
| 3 to 6 (postAR) | 55% | 0.09715168 | 97.7 | 6.986191 | 18 |

FIG. 15A p values comparing the AR prediction Score at AR vs preAR and postAR Scores

| Comparisons | p value |
|---|---|
| AR vs. 3−6 mo postAR | 2.57335E−06 |
| AR vs 3−6 mo preAR | 0.000418945 |
| AR vs 0−3 mo preAR | 5.09941E−08 |

FIG. 15B

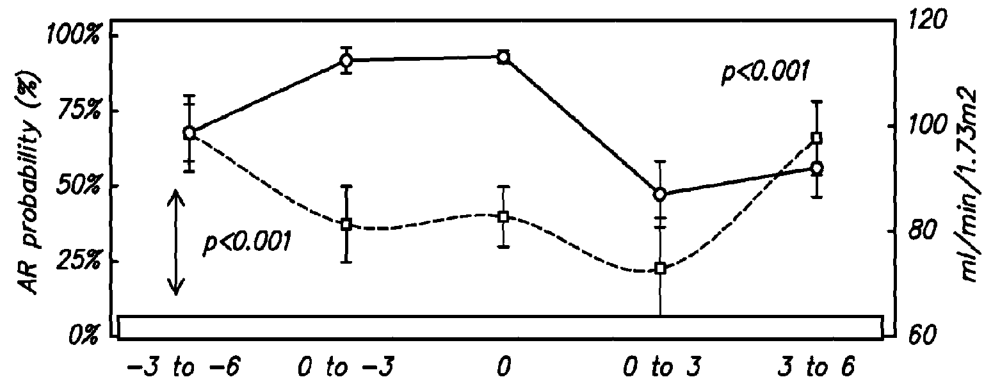

FIG. 15C

| sta | AR probability | crcl | n (CrCl) | stdev-crcl | stderr-crcl | AR_stdev | n | AR_stdev |
|---|---|---|---|---|---|---|---|---|
| 0 to 3 | 3% | 88.2 | 9 | 22.0 | 7.3 | 0.1 | 14.0 | 0.0 |
| 3 to 6 | 4% | 105.3 | 17 | 36.3 | 8.8 | 0.1 | 27.0 | 0.0 |
| 6 to 12 | 5% | 111.3 | 10 | 30.5 | 9.6 | 0.2 | 12.0 | 0.0 |
| >12 | 8% | 104.7 | 12 | 30.2 | 8.7 | 0.0 | 17.0 | 0.0 |

Biological Relevance Analysis for the Overlapping 525 Genes Across the 3 Array Platforms using Ingenuity Systems (IPA; 2008)

| Pathway | -Log(P-value) | Ratio | Molecules |
|---|---|---|---|
| Integrin Signaling | 6.19E+00 | 1.14E-01 | FYN, ARPC5L (includes EG:81873), PIK3R1, ARHGEF7, PPP1CB, KRAS, BCAR3, TNK2, RAP1A, ITGB7, PTEN, PTK2, WIPF1, RRAS2, MAP2K2, RHOT1, RHOA, ACTN4, TSPAN4, VASP, ACTN1, ITGAX |
| Leukocyte Extravasation Signaling | 4.23E+00 | 9.33E-02 | CD99 (includes EG:4267), MYL6, PIK3R1, CTNNA1, DLC1, RAP1A, PTK2, WIPF1, MAP2K2, EZR, RHOA, CYBB, GRLF1, RASSF5, ACTN4, ARHGAP1, VASP, ACTN1 |
| Hypoxia Signaling in the Cardiovascular System | 4.05E+00 | 1.41E-01 | UBE2A, UBE2D2, HSP90AA1, UBE2D3, UBE2E3, UBE2D1, UBE2J1, VHL, PTEN, ATM |
| PI3K/AKT Signaling | 3.31E+00 | 9.23E-02 | YWHAQ (includes EG:10971), IKBKB, CDC37, RRAS2, PPP2R5C, MAP2K2, GAB1, PIK3R1, HSP90AA1, KRAS, RHEB, PTEN |
| Actin Cytoskeleton Signaling | 3.27E+00 | 7.66E-02 | MYL6, ARPC5L (includes EG:81873), PIK3R1, ARHGEF7, GNA12, PPP1CB, KRAS, LIMK2, PTK2, CYFIP2, RRAS2, MAP2K2, EZR, RHOA, GRLF1, ACTN4, ACTN1 |
| Ephrin Receptor Signaling | 3.20E+00 | 7.98E-02 | FYN, AXIN1, ARPC5L (includes EG:81873), GNA12, KRAS, LIMK2, STAT3, RAP1A, GNG7, PTK2, WIPF1, RRAS2, MAP2K2, ABI1, RHOA |
| Chemokine Signaling | 3.16E+00 | 1.20E-01 | PTK2, CAMK2D, RRAS2, MAP2K2, RHOA, CALM2, PPP1CB, KRAS, LIMK2 |
| T Cell Receptor Signaling | 2.81E+00 | 9.52E-02 | FYN, SHB, IKBKB, LCK, RRAS2, MAP2K2, NFATC3, PIK3R1, CALM2, KRAS |
| IL-8 Signaling | 2.76E+00 | 7.65E-02 | PIK3R1, GNA12, KRAS, LIMK2, GNG7, PTK2, IKBKB, CCND2, RRAS2, MAP2K2, RHOT1, RHOA, CYBB, ITGAX |
| Glucocorticoid Receptor Signaling | 2.70E+00 | 6.55E-02 | TAF12, SMAD2, TAF11, NFATC3, POU2F2, PIK3R1, SMAD3, KRAS, TAF7, STAT3, POLR2B, SMARCA4, IKBKB, PTGES3, RRAS2, MAP2K2, HSP90AA1, TAF2 |
| B Cell Receptor Signaling | 2.50E+00 | 7.95E-02 | IKBKB, CAMK2D, RRAS2, MAP2K2, GAB1, NFATC3, POU2F2, PIK3R1, CALM2, LYN, KRAS, PTEN |

FIG. 16

| | | | |
|---|---|---|---|
| SAPK/JNK Signaling | 2.47E+00 | 9.68E−02 | SH2D2A, LCK, RRAS2, GAB1, NFATC3, PIK3R1, GNA12, KRAS, GNG7 |
| JAK/Stat Signaling | 2.45E+00 | 1.19E−01 | STAT4, PIAS3, RRAS2, MAP2K2, PIK3R1, KRAS, STAT3 |
| GM−CSF Signaling | 2.41E+00 | 1.13E−01 | CAMK2D, RRAS2, MAP2K2, PIK3R1, LYN, KRAS, STAT3 |
| Macropinocytosis | 2.21E+00 | 1.00E−01 | RRAS2, ABI1, RHOA, PIK3R1, KRAS, ACTN4, ITGB7 |
| VEGF Signaling | 2.18E+00 | 8.70E−02 | PTK2, EIF2B4, RRAS2, MAP2K2, PIK3R1, KRAS, ACTN4, ACTN1 |
| Protein Ubiquitination Pathway | 2.03E+00 | 6.44E−02 | UBE2A, UBR2, UBE2D2, PSMD6, UBE2D1, USP32, PSMC6, STUB1, HSP90AA1, UBE2D3, UBE2E3, UBE2J1, VHL |
| IL−6 Signaling | 1.97E+00 | 8.51E−02 | IL6ST, IKBKB, RRAS2, MAP2K2, CYP19A1, KRAS, STAT3, IL1R1 |
| Estrogen Receptor Signaling | 1.95E+00 | 7.63E−02 | TAF12, TAF11, RRAS2, MAP2K2, KRAS, TAF7, POLR2B, TAF2, SMARCA4 |
| Fc?? Receptor−mediated Phagocytosis in Macrophages and Monocytes | 1.81E+00 | 7.69E−02 | FYN, YES1, ARPC5L (includes EG:81873), EZR, PIK3R1, LYN, VASP, PTEN |
| ERK/MAPK Signaling | 1.77E+00 | 6.56E−02 | PTK2, YWHAQ (includes EG:10971), FYN, RRAS2, PPP2R5C, MAP2K2, PIK3R1, PPP1CB, KRAS, STAT3, RAP1A, ELF1 |
| Axonal Guidance Signaling | 1.67E+00 | 5.12E−02 | DPYSL2, FYN, MYL6, ARPC5L (includes EG:81873), NFATC3, PIK3R1, ARHGEF7, GNA12, KRAS, LIMK2, RAP1A, GNG7, PTK2, WIPF1, RRAS2, MAP2K2, RHOA, RTN4, RASSF5, VASP |
| Insulin Receptor Signaling | 1.59E+00 | 6.77E−02 | FYN, EIF2B4, RRAS2, MAP2K2, GAB1, PIK3R1, PPP1CB, KRAS, PTEN |
| Neuregulin Signaling | 1.57E+00 | 7.53E−02 | RRAS2, MAP2K2, PIK3R1, HSP90AA1, KRAS, PSEN1, PTEN |
| IL−2 Signaling | 1.55E+00 | 9.43E−02 | LCK, RRAS2, MAP2K2, PIK3R1, KRAS |
| PTEN Signaling | 1.53E+00 | 7.45E−02 | PTK2, IKBKB, RRAS2, MAP2K2, PIK3R1, KRAS, PTEN |
| PPAR Signaling | 1.53E+00 | 7.14E−02 | PPARA, IKBKB, RRAS2, MAP2K2, HSP90AA1, KRAS, IL1R1 |

FIG. 16 (CONT.)

| | | | |
|---|---|---|---|
| Inositol Phosphate Metabolism | 1.45E+00 | 5.20E−02 | INPP4B, ITPKB, MAP2K2, INPP5B, PIK3R1, CSNK1A1, LIMK2, PTEN, ATM |
| Fc Epsilon RI Signaling | 1.37E+00 | 6.93E−02 | FYN, RRAS2, MAP2K2, GAB1, PIK3R1, LYN, KRAS |
| Methionine Metabolism | 1.32E+00 | 3.95E−02 | AMD1, MTR, DNMT1 |
| PPAR??/RXR?? Activation | 1.21E+00 | 5.49E−02 | PPARA, SMAD2, IKBKB, RRAS2, MAP2K2, SMAD3, HSP90AA1, NR2C2, KRAS, IL1R1 |
| Regulation of Actin-based Motility by Rho | 1.18E+00 | 6.52E−02 | WIPF1, MYL6, RHOT1, ARPC5L (includes EG:81873), RHOA, PPP1CB |
| Synaptic Long Term Potentiation | 1.18E+00 | 6.25E−02 | CAMK2D, RRAS2, MAP2K2, CALM2, PPP1CB, KRAS, RAP1A |
| Neurotrophin/TRK Signaling | 1.16E+00 | 6.76E−02 | RRAS2, MAP2K2, GAB1, PIK3R1, KRAS |
| IGF-1 Signaling | 1.12E+00 | 6.45E−02 | PTK2, YWHAQ (includes EG:10971), RRAS2, MAP2K2, PIK3R1, KRAS |
| Tight Junction Signaling | 1.09E+00 | 5.49E−02 | CPSF2, MYL6, PPP2R5C, RHOA, VAPA, CTNNA1, CSTF3, VASP, PTEN |
| Citrate Cycle | 1.08E+00 | 5.08E−02 | SDHD, IDH3A, OGDH |
| PDGF Signaling | 1.08E+00 | 6.76E−02 | RRAS2, MAP2K2, PIK3R1, KRAS, STAT3 |
| Aryl Hydrocarbon Receptor Signaling | 1.03E+00 | 5.26E−02 | PTGES3, CCND2, NQO2, HSP90AA1, AHR, SMARCA4, ATM, MCM7 |
| Ceramide Signaling | 9.39E−01 | 6.10E−02 | RRAS2, PPP2R5C, PIK3R1, CYCS (includes EG:54205), KRAS |
| Acute Phase Response Signaling | 9.38E−01 | 5.11E−02 | IL6ST, IKBKB, RRAS2, MAP2K2, PIK3R1, NOLC1, KRAS, STAT3, IL1R1 |
| Cell Cycle: G1/S Checkpoint Regulation | 9.22E−01 | 6.90E−02 | CCND2, SMAD3, E2F3, ATM |

FIG. 16 (CONT.)

| | | | |
|---|---|---|---|
| Caveolar-mediated Endocytosis | 9.03E-01 | 6.17E-02 | FLNB, FYN, CD55, ITGB7, ITGAX |
| TGF-?? Signaling | 9.03E-01 | 6.02E-02 | SMAD2, RRAS2, MAP2K2, SMAD3, KRAS |
| Pyrimidine Metabolism | 8.86E-01 | 3.51E-02 | DPYSL2, DUT (includes EG:1854), DPYD, ITPA, POLE2, POLR3E, POLR2B, POLE |
| Natural Killer Cell Signaling | 8.44E-01 | 5.45E-02 | FYN, LCK, RRAS2, MAP2K2, PIK3R1, KRAS |
| Death Receptor Signaling | 8.41E-01 | 6.15E-02 | TANK, IKBKB, CYCS (includes EG:54205), CFLAR |
| IL-12 Signaling and Production in Macrophages | 8.30E-01 | 4.69E-02 | STAT4, IKBKB, MAP2K2, PIK3R1, IFNGR1, SPI1 |
| Pantothenate and CoA Biosynthesis | 7.92E-01 | 3.17E-02 | DPYSL2, DPYD |
| Apoptosis Signaling | 7.75E-01 | 5.49E-02 | IKBKB, RRAS2, MAP2K2, CYCS (includes EG:54205), KRAS |
| p53 Signaling | 7.46E-01 | 5.75E-02 | CCNG1, CCND2, PIK3R1, PTEN, ATM |
| IL-4 Signaling | 7.35E-01 | 5.71E-02 | RRAS2, NFATC3, PIK3R1, KRAS |
| Erythropoietin Signaling | 7.19E-01 | 5.33E-02 | RRAS2, MAP2K2, PIK3R1, KRAS |
| G-Protein Coupled Receptor Signaling | 6.92E-01 | 4.46E-02 | FYN, IKBKB, CAMK2D, RRAS2, MAP2K2, PIK3R1, KRAS, STAT3, RAP1A |
| ??-Adrenergic Signaling | 6.92E-01 | 4.67E-02 | RRAS2, MAP2K2, CALM2, KRAS, GNG7 |
| Xenobiotic Metabolism Signaling | 6.75E-01 | 4.40E-02 | PTGES3, CAMK2D, RRAS2, PPP2R5C, MAP2K2, NQO2, PIK3R1, HSP90AA1, KRAS, NDST1, AHR |
| N-Glycan Degradation | 6.49E-01 | 6.67E-02 | MAN2C1, MAN2A1 |
| N-Glycan Biosynthesis | 6.26E-01 | 3.45E-02 | STT3B, ST6GAL1, MAN2A1 |

FIG. 16 (CONT.)

| | | | |
|---|---|---|---|
| Role of BRCA1 in DNA Damage Response | 6.09E−01 | 5.77E−02 | E2F3, SMARCA4, ATM |
| Amyloid Processing | 5.93E−01 | 5.77E−02 | CSNK1E, CSNK1A1, PSEN1 |
| 14−3−3−mediated Signaling | 5.72E−01 | 4.49E−02 | YWHAQ (includes EG:10971), RRAS2, MAP2K2, PIK3R1, CSNK1A1, KRAS, LIMK2 |
| Complement System | 5.03E−01 | 5.56E−02 | CD59, CD55 |
| Synaptic Long Term Depression | 4.87E−01 | 3.73E−02 | RRAS2, PPP2R5C, MAP2K2, GNA12, LYN, KRAS |
| Nucleotide Excision Repair Pathway | 4.69E−01 | 5.71E−02 | POLR2B, RAD23B |
| IL−10 Signaling | 4.56E−01 | 4.23E−02 | IKBKB, STAT3, IL1R1 |
| NF−??B Signaling | 4.56E−01 | 4.14E−02 | IKBKB, LCK, RRAS2, PIK3R1, KRAS, IL1R1 |
| Glutamate Metabolism | 4.38E−01 | 2.56E−02 | CCDC92 (includes EG:80212), QARS |
| Nicotinate and Nicotinamide Metabolism | 4.27E−01 | 3.10E−02 | MAP2K2, CSNK1A1, NAMPT, LIMK2 |
| Notch Signaling | 4.23E−01 | 4.88E−02 | DTX1, PSEN1 |
| Phenylalanine, Tyrosine and Tryptophan Biosynthesis | 4.12E−01 | 1.54E−02 | YARS |
| Lysine Degradation | 4.12E−01 | 2.08E−02 | PPP2R5C, PCSK7, OGDH |
| Cell Cycle: G2/M DNA Damage Checkpoint Regulation | 4.09E−01 | 4.65E−02 | CCNB2, ATM |
| Aminoacyl−tRNA Biosynthesis | 3.96E−01 | 2.38E−02 | YARS, QARS |

FIG. 16 (CONT.)

| | | | |
|---|---|---|---|
| Role of PKR in Interferon Induction and Antiviral Response | 3.83E-01 | 4.26E-02 | IKBKB, CYCS (includes EG:54205) |
| Bile Acid Biosynthesis | 3.83E-01 | 2.06E-02 | ADH6, ADHFE1 |
| cAMP-mediated Signaling | 3.73E-01 | 3.77E-02 | AKAP13, CAMK2D, MAP2K2, CALM2, STAT3, RAP1A |
| Parkinson's Signaling | 3.68E-01 | 5.88E-02 | CYCS (includes EG:54205) |
| Hepatic Fibrosis / Hepatic Stellate Cell Activation | 3.67E-01 | 3.70E-02 | SMAD2, MYL6, SMAD3, IFNGR1, IL1R1 |
| Clatrin-mediated Endocytosis | 3.66E-01 | 3.64E-02 | CD2AP, AP1G2, ARPC5L (includes EG:81873), PIK3R1, TFRC, ITGB7 |
| EGF Signaling | 3.59E-01 | 4.26E-02 | PIK3R1, STAT3 |
| Nitric Oxide Signaling in the Cardiovascular System | 3.45E-01 | 3.33E-02 | PIK3R1, CALM2, HSP90AA1 |
| Chondroitin Sulfate Biosynthesis | 3.36E-01 | 3.28E-02 | B3GALT6, NDST1 |
| Role of RIG1-like Receptors in Antiviral Innate Immunity | 3.36E-01 | 3.85E-02 | TANK, IKBKB |
| Endoplasmic Reticulum Stress Pathway | 3.30E-01 | 5.56E-02 | MBTPS1 |
| BMP signaling pathway | 3.28E-01 | 3.75E-02 | RRAS2, MAP2K2, KRAS |

FIG. 16 (CONT.)

| | | | |
|---|---|---|---|
| Mitochondrial Dysfunction | 3.28E-01 | 2.94E-02 | NDUFV1, SDHD, CYCS (includes EG:54205), OGDH, PSEN1 |
| Toll-like Receptor Signaling | 3.06E-01 | 3.70E-02 | PPARA, IKBKB |
| VDR/RXR Activation | 3.04E-01 | 3.75E-02 | SERPINB1, CCNC, MXD1 |
| Riboflavin Metabolism | 2.98E-01 | 2.04E-02 | NUP160 |
| Purine Metabolism | 2.93E-01 | 2.40E-02 | DLG1, IMPDH2, ITPA, POLE2, PSMC6, POLR3E, ADK, POLR2B, SMARCA4, POLE |
| FGF Signaling | 2.89E-01 | 3.57E-02 | GAB1, PIK3R1, STAT3 |
| Calcium Signaling | 2.84E-01 | 2.97E-02 | CAMK2D, MYL6, NFATC3, CALM2, RAP1A, RCAN1 |
| One Carbon Pool by Folate | 2.84E-01 | 2.63E-02 | MTR |
| ??-alanine Metabolism | 2.69E-01 | 2.02E-02 | DPYSL2, DPYD |
| Cardiac ??-adrenergic Signaling | 2.46E-01 | 2.94E-02 | AKAP13, PPP2R5C, PPP1CB, GNG7 |
| Glutamate Receptor Signaling | 2.45E-01 | 2.99E-02 | CALM2, GNG7 |
| TREM1 Signaling | 2.31E-01 | 2.90E-02 | STAT3, ITGAX |
| O-Glycan Biosynthesis | 2.04E-01 | 2.33E-02 | GALNT1 |
| Circadian Rhythm Signaling | 2.04E-01 | 3.12E-02 | CSNK1E |
| Interferon Signaling | 2.04E-01 | 3.45E-02 | IFNGR1 |
| Biosynthesis of Steroids | 1.95E-01 | 7.87E-03 | NQO2 |

| Unique Sample ID | cDNA_PB | Agilent_PB | Affy_PB | Affy_PBL | PCR_verification | PCR_validation 1 | PCR_validation 2 | paired AR | preAR | postAR | Sample_date | Tx_date | DOB | post_Tx_time | Recipient Age | Recipient Gender | Donor Gender | Donor Source | Donor Age | Steroid-Free (SF) vs Steroid Based (SB) | HLA_Match |
|---|---|---|---|---|---|---|---|---|---|---|---|---|---|---|---|---|---|---|---|---|---|
| S01 | | | | | | | | | | | 3/19/02 | 12/1/99 | 9/5/88 | 27.5 | 11.2 | F | M | LRD | 43.7 | SF | |
| S02 | | | | | | | | | | | 5/17/02 | 12/1/99 | 9/5/88 | 29.4 | 11.2 | F | M | LRD | 43.7 | SF | |
| S03 | | | | | | | | | | | 1/31/03 | 1/16/02 | 8/10/91 | 12.5 | 10.4 | F | F | LRD | 35.8 | SF | |
| S04 | | | | | | | | | | | 3/7/03 | 7/21/92 | 1/27/85 | 127.2 | 7.5 | M | | | | SB | |
| S05 | | | | | | | | | | | 3/14/03 | 2/27/02 | 4/23/01 | 12.5 | 0.8 | M | M | LRD | 27.6 | SF | |
| S06 | | | | | | | | | | | 5/12/03 | 11/18/02 | 11/21/86 | 5.7 | 16.0 | M | F | LRD | 40.1 | SF | |
| S07 | | | | | | | | | | | 8/4/03 | 12/9/02 | 5/21/88 | 7.8 | 14.6 | F | F | LUD | 36.3 | SF | |
| S08 | | | | | | | | | | | 8/15/03 | 5/20/03 | 12/5/95 | 2.9 | 7.5 | M | M | LRD | 39.7 | SF | |
| S09 | | | | | | | | | | | 9/4/03 | | 1/7/03 | | | M | | | | SB | |
| S10 | | | | | | | | | | | 9/4/03 | 8/1/01 | 10/26/87 | 25.0 | 13.8 | M | F | LUD | 22.8 | SF | |
| S11 | | | | | | | | | | | 9/4/03 | 11/7/01 | 10/6/91 | 21.8 | 10.1 | M | F | LRD | 44.4 | SF | |
| S12 | | | | | | | | | | | 9/4/03 | | 7/17/97 | | | M | | | | | |
| S13 | | | | | | | | | | | 9/4/03 | 11/26/96 | 2/2/82 | 81.1 | 14.8 | M | | LRD | | | |
| S14 | | | | | | | | | | | 9/4/03 | 1/0/00 | 6/25/98 | | | F | | | | | |
| A01 | | | | | | | | | | | 2/4/02 | 3/21/01 | 1/7/99 | 10.5 | 2.2 | M | M | LRD | 46.0 | SF | |
| A02 | | | | | | | | | | | 4/19/02 | 4/22/98 | 2/2/86 | 47.8 | 12.2 | M | F | LRD | 41.6 | SB | |
| A03 | | | | | | | | | | | 5/16/02 | 4/10/02 | 4/11/84 | 1.2 | 18.0 | F | F | LRD | 38.0 | SF | |
| A04 | | | | | | | | | | | 7/5/02 | 11/28/01 | 12/23/86 | 7.2 | 14.9 | M | F | LRD | 44.9 | SF | |
| A05 | | | | | | | | | | | 10/11/02 | 11/28/01 | 12/23/86 | 10.4 | 14.9 | M | M | LRD | 44.9 | SF | |
| A06 | | | | | | | | | | | 11/11/02 | 11/28/01 | 12/23/86 | 11.4 | 14.9 | M | F | LRD | 44.9 | SF | |
| A07 | | | | | | | | | | | 11/15/02 | 6/4/93 | 1/19/90 | 113.1 | 3.4 | F | | | | SB | |
| S15 | | | | | | | | | | | 5/1/02 | 11/11/98 | 6/18/82 | 41.5 | 16.4 | M | F | LRD | 41.4 | SB | |
| S16 | | | | | | | | | | | 5/14/02 | 12/3/99 | 5/5/83 | 29.3 | 16.6 | F | M | CAD | 39.1 | SF | |
| S17 | | | | | | | | | | | 7/26/02 | 12/14/95 | 3/2/80 | 79.2 | 15.8 | F | | LRD | 40.9 | SB | |
| S18 | | | | | | | | | | | 4/3/03 | 2/28/01 | 4/27/83 | 25.0 | 17.8 | M | F | LRD | 41.0 | SF | |
| S19 | | | | | | | | | | | 4/16/04 | 1/5/04 | 1/14/02 | 3.3 | 2.0 | M | M | LRD | 33.8 | SF | |
| S20 | | | | | | | | | | | 6/9/04 | 5/4/02 | 4/18/85 | 25.1 | 17.0 | M | M | Cad | 17.7 | SB | |
| S21 | | | | | | | | | | | 9/20/04 | 3/7/04 | 8/4/85 | 6.5 | 18.6 | M | M | CAD | 25.1 | SF | |
| S22 | | | | | | | | | | | 9/27/04 | 3/28/04 | 1/6/87 | 6.0 | 17.2 | M | F | LRD | 29.0 | SB | |
| S23 | | | | | | | | | | | 4/4/05 | 11/10/04 | 12/29/93 | 4.8 | 10.9 | F | F | LRD | 31.3 | SB | |
| S24 | | | | | | | | | | | 1/12/06 | 6/20/05 | 4/3/04 | 6.8 | 1.2 | F | M | LRD | 27.1 | SF | |
| S25 | | | | | | | | | | | 8/7/06 | 8/10/05 | 10/30/86 | 11.9 | 18.8 | F | M | CAD | 19.0 | SB | |
| A08 | | | | | | | | | | | 12/13/02 | 12/6/99 | 1/18/83 | 36.2 | 16.9 | F | F | LRD | 39.2 | SB | |
| A09 | | | | | | | | | | | 6/16/03 | 10/10/01 | 8/25/89 | 20.1 | 12.1 | M | M | LRD | 34.1 | SB | |
| A10 | | | | | | | | | | | 11/27/03 | 4/2/92 | 5/1/86 | 139.5 | 5.9 | F | F | LRD | 8.3 | SB | |
| A11 | | | | | | | | | | | 1/16/04 | 4/22/98 | 2/2/86 | 68.7 | 12.2 | M | F | LRD | 47.0 | SB | |
| A12 | | | | | | | | | | | 1/29/04 | 5/7/92 | 2/16/88 | 140.5 | 4.2 | M | M | LRD | 22.0 | SB | |
| A13 | | | | | | | | | | | 2/20/04 | 8/13/02 | 7/6/84 | 18.2 | 18.1 | M | M | CAD | 21.0 | SF | |
| A14 | | | | | | | | | | | 3/18/04 | 6/9/03 | 9/14/84 | 9.3 | 18.7 | F | M | LRD | 38.9 | SF | |
| A15 | | | | | | | | | | | 4/1/04 | 9/1/99 | 11/15/87 | 54.9 | 11.8 | F | M | LRD | 37.7 | SB | |
| A16 | | | | | | | | | | | 7/13/04 | 5/12/03 | 8/9/93 | 14.0 | 9.8 | M | M | LRD | 33.1 | SF | |
| A17 | | | | | | | | | | | 9/2/04 | 7/10/96 | 6/20/86 | 97.6 | 10.1 | M | M | LRD | 34.2 | SB | |
| A18 | | | | | | | | | | | 7/27/00 | 2/11/00 | 8/27/82 | 5.5 | 17.5 | F | F | Cad | 0.0 | SB | |
| A19 | | | | | | | | | | | 7/27/00 | 7/10/96 | 6/20/86 | 48.5 | 10.1 | M | M | LRD | 34.2 | SB | |
| S26 | | | | | | | | | | | 4/21/03 | 4/2/92 | 5/1/86 | 132.3 | 5.9 | F | F | LRD | 8.3 | SB | 1 |
| S27 | | | | | | | | | | | 7/29/03 | 8/5/02 | 3/14/91 | 11.7 | 11.4 | F | M | LRD | 21.4 | SF | 2 |
| S28 | | | | | | | | | | | 1/29/04 | 1/9/02 | 8/6/91 | 24.6 | 10.4 | M | M | LURD | 44.7 | SF | 1 |
| S29 | | | | | | | | | | | 3/12/04 | 10/3/03 | 2/10/92 | 5.3 | 11.6 | F | F | CAD | 16.0 | SF | 0 |
| S30 | | | | | | | | | | | 4/6/04 | 1/12/04 | 10/1/02 | 2.8 | 1.3 | F | F | LRD | 32.2 | SF | 2 |
| S31 | | | | | | | | | | | 6/1/04 | 7/10/96 | 6/20/86 | 94.5 | 10.1 | M | M | LRD | 34.2 | SB | 2 |
| S32 | | | | | | | | | | | 9/30/04 | 6/28/04 | 11/13/02 | 3.1 | 1.6 | F | F | LRD | 42.0 | SB | 3 |
| S33 | | | | | | | | | | | 10/5/04 | 3/30/04 | 7/9/83 | 6.2 | 20.7 | F | M | CAD | 50.1 | SB | 2 |
| S34 | | | | | | | | | | | 10/19/04 | 8/28/97 | 10/26/94 | 85.5 | 2.8 | F | F | CAD | 7.8 | SB | 5 |
| S35 | | | | | | | | | | | 11/23/04 | 11/18/02 | 11/21/86 | 24.1 | 16.0 | M | F | LRD | 40.1 | SF | 4 |
| S36 | | | | | | | | | | | 12/21/04 | 5/8/02 | 1/26/99 | 31.4 | 3.3 | M | M | LRD | 19.8 | SF | 3 |
| S37 | | | | | | | | | | | 1/24/05 | 6/30/04 | 10/12/87 | 6.8 | 16.7 | M | M | LRD | 37.0 | SB | 0 |
| S38 | | | | | | | | | | | 3/9/05 | 7/12/04 | 7/7/90 | 7.9 | 14.0 | M | M | LRD | 37.5 | SB | 3 |
| S39 | | | | | | | | | | | 6/22/05 | 12/20/04 | 7/15/03 | 6.0 | 1.4 | M | M | LRD | 28.0 | SB | 1 |
| S40 | | | | | | | | | | | 7/25/05 | 5/16/05 | 7/31/89 | 2.3 | 15.8 | F | M | LURD | 38.5 | SB | 4 |
| S41 | | | | | | | | | | | 7/26/05 | 8/25/03 | 2/2/00 | 23.0 | 3.6 | M | F | LRD | 30.8 | SF | 6 |
| S42 | | | | | | | | | | | 11/22/05 | 6/7/05 | 1/5/99 | 5.5 | 6.4 | M | F | CAD | 16.0 | SF | 2 |
| S43 | | | | | | | | | | | 1/9/06 | 7/28/05 | 10/14/99 | 5.4 | 5.8 | F | M | LRD | 44.0 | SB | 1 |
| S44 | | | | | | | | | | | 4/5/06 | 9/30/05 | 10/7/85 | 6.1 | 20.0 | F | F | CAD | 24.0 | SF | 0 |
| S45 | | | | | | | | | | | 6/2/06 | 12/3/05 | 3/13/99 | 5.9 | 6.7 | F | F | CAD | 23.0 | SF | 0 |
| S46 | | | | | | | | | | | 6/9/06 | 3/28/06 | 8/21/02 | 2.4 | 3.6 | M | M | CAD | 14.8 | SF | 4 |
| S47 | | | | | | | | | | | 7/25/06 | 1/19/06 | 11/28/97 | 6.1 | 8.1 | F | M | CAD | 15.0 | SF | 1 |
| A20 | | | | | | | | | | | 12/5/03 | 10/1/02 | 9/14/89 | 14.1 | 13.0 | M | | CAD | | SB | 2 |
| A21 | | | | | | | | | | | 12/5/04 | 3/30/04 | 7/9/83 | 8.2 | 20.7 | F | M | CAD | 50.1 | SB | 2 |
| A22 | | | | | | | | | | | 2/3/05 | 9/27/04 | 1/2/95 | 4.2 | 9.7 | M | F | LRD | 31.0 | SF | 3 |

Fig. 18 (cont.)

| | | | | | | | | | | | |
|---|---|---|---|---|---|---|---|---|---|---|---|
| A23 | 2/11/05 | 12/10/04 | 8/6/87 | 2.1 | 17.3 | M | F | CAD | 34.0 | SB | 0 |
| A24 | 2/16/05 | 8/10/04 | 4/1/93 | 6.2 | 11.4 | M | M | LRD | 43.0 | SF | 2 |
| A25 | 3/13/05 | 9/27/04 | 1/2/95 | 5.5 | 9.7 | M | F | LRD | 31.0 | SF | 3 |
| A26 | 3/21/05 | 8/20/04 | 4/28/95 | 7.0 | 9.3 | M | F | CAD | 9.1 | SF | 5 |
| A27 | 4/6/05 | 9/27/04 | 1/2/95 | 6.3 | 9.7 | M | F | LRD | 31.0 | SF | 2 |
| A28 | 5/12/05 | 12/10/04 | 8/6/87 | 5.0 | 17.3 | M | F | CAD | 34.0 | SB | 0 |
| A29 | 8/31/05 | 3/30/04 | 7/9/83 | 17.0 | 20.7 | F | M | CAD | 50.1 | SB | 2 |
| A30 | 11/4/05 | 10/3/03 | 2/10/92 | 25.0 | 11.6 | F | F | CAD | 16.0 | SF | 0 |
| A31 | 1/25/06 | 10/10/01 | 8/25/89 | 51.4 | 12.1 | M | M | LRD | 34.1 | SB | 2 |
| A32 | 2/27/06 | 8/29/05 | 11/22/90 | 6.0 | 14.8 | M | M | LRD | 42.2 | SF | 3 |
| A33 | 2/23/06 | 3/30/04 | 7/9/83 | 22.8 | 20.7 | F | M | CAD | 50.1 | SB | 2 |
| A34 | 4/12/06 | 1/1/06 | 12/26/93 | 3.3 | 12.0 | F | M | CAD | 23.0 | SB | 0 |
| A35 | 4/27/06 | 7/10/05 | 12/10/87 | 9.5 | 17.6 | M | | CAD | 37.1 | SF | 2 |
| A36 | 5/1/06 | 10/11/04 | 11/4/97 | 18.6 | 6.9 | M | F | LRD | 43.0 | SF | 2 |
| A37 | 7/11/06 | 8/28/97 | 10/26/94 | 106.2 | 2.8 | F | F | CAD | 7.8 | SB | 5 |
| A38 | 7/14/06 | 1/8/06 | 3/13/94 | 6.1 | 11.8 | F | | CAD | 26.8 | SB | 3 |
| A39 | 7/25/06 | 8/2/04 | 2/1/89 | 23.7 | 15.5 | M | F | LRD | 19.5 | SF | 2 |
| A40 | 9/26/06 | 10/11/04 | 11/4/97 | 23.4 | 6.9 | M | F | LRD | 43.0 | SF | 2 |
| S48 | 9/7/06 | 3/28/04 | 1/6/87 | 29.3 | 17.2 | M | F | CAD | 30.0 | SB | |
| S49 | 9/22/06 | 3/15/06 | 7/7/97 | 6.3 | 8.7 | F | M | LRD | 39.2 | SB | |
| S50 | 10/2/06 | 11/7/01 | 10/6/91 | 58.7 | 10.1 | M | F | LRD | 44.4 | SF | |
| S51 | 10/11/06 | 9/9/02 | 9/21/85 | 49.0 | 17.0 | M | M | LRD | 39.6 | SF | |
| S52 | 11/17/06 | 5/3/06 | 1/2/90 | 6.5 | 16.3 | M | M | LRD | 46.4 | SF | |
| S53 | 12/1/06 | 10/4/04 | 5/7/86 | 25.8 | 18.4 | M | F | LRD | 50.6 | SF | |
| S54 | 2/12/07 | 4/24/06 | 4/25/05 | 9.6 | 1.0 | F | M | LRD | 28.9 | SF | |
| S55 | 2/16/07 | 8/23/04 | 9/26/97 | 29.7 | 6.9 | F | F | LRD | 37.8 | SB | |
| S56 | 2/25/07 | 3/21/05 | 7/31/88 | 23.1 | 16.6 | M | F | LRD | 47.1 | SF | |
| A41 | 7/20/06 | 8/28/97 | 10/26/94 | 106.5 | 2.8 | F | M | CAD | 6.0 | SB | |
| A42 | 7/25/06 | 8/2/04 | 2/1/89 | 23.7 | 15.5 | M | F | LRD | 19.5 | SF | |
| A43 | 10/16/06 | 10/11/04 | 11/4/97 | 24.1 | 6.9 | M | F | LRD | 43.0 | SF | |
| A44 | 11/3/06 | 7/10/05 | 12/10/87 | 15.8 | 17.6 | M | M | CAD | 37.0 | SF | |
| A45 | 11/22/06 | 1/9/02 | 8/6/91 | 58.3 | 10.4 | M | M | LRD | 44.7 | SF | |
| A46 | 4/3/07 | 9/25/06 | 11/24/89 | 6.2 | 16.8 | M | F | LRD | 50.9 | SF | |
| A47 | 4/3/07 | 3/28/04 | 1/6/87 | 36.1 | 17.2 | M | F | CAD | 30.0 | SB | |
| A48 | 1/7/05 | 6/28/04 | 11/13/02 | 6.3 | 1.6 | F | F | LRD | 42.0 | SB | 3 |
| S57 | 7/1/04 | 6/30/03 | 7/10/85 | 12.0 | 18.0 | M | F | LRD | 38.8 | SF | 2 |
| S58 | 7/14/04 | 7/22/02 | 11/21/90 | 23.7 | 11.7 | F | M | LRD | 48.1 | SF | 4 |
| S59 | 9/13/04 | 3/7/04 | 8/4/85 | 6.2 | 18.6 | M | M | CAD | 25.1 | SF | 1 |
| S60 | 3/30/05 | 9/29/04 | 12/4/86 | 6.0 | 17.8 | M | M | LRD | 21.0 | SF | 3 |
| S61 | 8/2/05 | 7/30/03 | 5/10/01 | 24.1 | 2.2 | F | F | LRD | 27.0 | SB | 5 |
| S62 | 9/29/05 | 9/29/04 | 12/4/86 | 12.0 | 17.8 | M | M | LRD | 21.0 | SF | 3 |
| S63 | 10/6/05 | 4/4/05 | 4/21/95 | 6.1 | 10.0 | M | M | CAD | 18.0 | SB | 0 |
| S64 | 11/14/05 | 5/16/05 | 7/31/89 | 6.0 | 15.8 | F | M | LRD | 38.5 | SB | 4 |
| S65 | 11/18/05 | 10/4/04 | 5/7/86 | 13.4 | 18.4 | M | F | LRD | 50.6 | SF | 4 |
| S66 | 12/15/05 | 6/30/05 | 1/2/03 | 5.5 | 2.5 | F | F | LRD | 54.0 | SB | 3 |
| S67 | 12/16/05 | 11/15/04 | 8/23/95 | 13.0 | 9.2 | M | F | LRD | 30.4 | SF | 2 |
| S68 | 1/27/06 | 8/1/05 | 3/6/98 | 5.9 | 7.4 | M | F | CAD | 32.0 | SF | 2 |
| S69 | 3/6/06 | 9/22/05 | 7/19/90 | 5.4 | 15.2 | F | M | LRD | 35.0 | SB | 0 |
| S70 | 3/7/06 | 9/1/05 | 11/25/91 | 6.1 | 13.8 | F | F | CAD | 20.0 | SB | 0 |
| S71 | 6/15/06 | 12/19/05 | 2/27/90 | 5.8 | 15.8 | F | F | LRD | 36.0 | SF | 3 |
| S72 | 7/6/06 | 1/4/06 | 6/22/93 | 6.0 | 12.5 | M | M | LRD | 21.0 | SF | 4 |
| S73 | 7/26/06 | 1/25/06 | 7/15/89 | 6.0 | 16.5 | M | F | CAD | 28.0 | SB | 0 |
| S74 | 9/26/06 | 3/31/06 | 4/10/88 | 5.9 | 18.0 | F | F | CAD | 25.0 | SF | 0 |
| S75 | 10/19/06 | 4/19/06 | 6/17/96 | 6.0 | 9.8 | M | F | CAD | 18.0 | SB | 1 |
| S76 | 10/26/06 | 4/28/06 | 12/22/89 | 5.9 | 16.3 | F | M | CAD | 24.0 | SF | 1 |
| A49 | 4/21/03 | 12/11/00 | 12/11/83 | 28.2 | 17.0 | M | M | LRD | 36.3 | SF | 4 |
| A50 | 2/20/04 | 4/22/98 | 2/2/86 | 69.8 | 12.2 | M | F | LRD | 41.0 | SB | 4 |
| A51 | 6/1/04 | 9/1/99 | 11/15/87 | 56.9 | 11.8 | F | M | LRD | 37.7 | SB | 5 |
| A52 | 7/2/04 | 1/12/04 | 10/1/02 | 5.6 | 1.3 | F | F | LRD | 32.2 | SF | 2 |
| A53 | 8/17/04 | 11/28/01 | 12/23/86 | 32.6 | 14.9 | M | F | LRD | 44.0 | SB | 3 |
| A54 | 3/1/05 | 2/17/05 | 11/1/01 | 0.4 | 3.3 | M | F | CAD | 33.1 | SF | 3 |
| A55 | 4/8/05 | 4/6/05 | 2/19/96 | 0.1 | 9.1 | M | M | CAD | 16.0 | SF | 0 |
| A56 | 8/24/05 | 8/13/05 | 7/30/89 | 0.4 | 16.0 | F | F | CAD | 29.0 | SF | 1 |
| A57 | 10/28/05 | 1/9/02 | 8/6/91 | 45.5 | 10.4 | M | M | LRD | 44.7 | SF | 1 |
| A58 | 10/27/05 | 10/21/05 | 6/23/88 | 0.2 | 17.3 | F | M | CAD | 14.0 | SB | 0 |
| A59 | 12/8/05 | 8/16/05 | 6/6/02 | 3.7 | 3.2 | M | M | CAD | 5.0 | SB | 0 |
| A60 | 12/13/05 | 1/9/02 | 8/6/91 | 47.0 | 10.4 | M | M | LRD | 44.7 | SF | 1 |
| A61 | 12/22/05 | 8/16/05 | 6/6/02 | 4.2 | 3.2 | M | M | CAD | 5.0 | SB | 0 |
| A62 | 5/30/06 | 11/27/05 | 10/16/88 | 6.0 | 17.1 | M | F | CAD | 31.0 | SB | 0 |
| A63 | 5/30/06 | 6/7/05 | 1/5/99 | 11.7 | 6.4 | M | F | CAD | 16.0 | SF | 2 |
| A64 | 6/9/06 | 4/13/06 | 1/20/91 | 1.9 | 15.2 | M | M | CAD | 22.0 | SB | 0 |
| A65 | 6/20/06 | 1/4/06 | 4/16/90 | 5.5 | 15.7 | M | M | CAD | 23.0 | SB | 1 |
| A66 | 7/3/06 | 6/5/06 | 8/29/90 | 0.9 | 15.8 | M | M | CAD | 28.0 | SF | 0 |
| A67 | 7/21/06 | 1/12/06 | 5/4/88 | 6.2 | 17.7 | F | M | CAD | 18.0 | SF | 0 |
| A68 | 9/11/06 | 3/24/06 | 8/10/01 | 5.6 | 4.6 | M | F | CAD | 28.0 | SF | 4 |
| A69 | 9/26/06 | 3/20/06 | 2/13/89 | 6.2 | 17.1 | F | M | LRD | 37.0 | SF | 2 |
| S77 | 4/19/02 | 1/16/02 | 8/10/91 | 3.0 | 10.4 | F | M | LRD | 36.0 | SF | 3 |

Fig. 18 (cont.)

| | | | | | | | | | | | |
|---|---|---|---|---|---|---|---|---|---|---|---|
| S78 | 5/30/02 | 2/25/02 | 12/14/81 | 3.1 | 20.2 | M | F | LRD | 51.0 | SF | 0 |
| S79 | 11/12/02 | 5/20/02 | 1/14/82 | 5.8 | 20.3 | F | M | CAD | 24.0 | SF | 1 |
| S80 | 1/21/03 | 7/22/02 | 11/21/90 | 6.0 | 11.7 | F | M | LRD | 48.0 | SF | 4 |
| S81 | 2/13/03 | 11/18/02 | 11/21/86 | 2.9 | 16.0 | M | F | LRD | 40.1 | SF | 4 |
| S82 | 6/10/03 | 3/24/03 | 7/26/88 | 2.6 | 14.7 | M | M | LRD | 39.8 | SF | 1 |
| S83 | 8/13/03 | 7/17/02 | 7/28/94 | 12.9 | 8.0 | F | F | LRD | 44.1 | SF | 4 |
| S84 | 11/21/03 | 11/18/02 | 11/21/86 | 12.1 | 16.0 | M | F | LRD | 40.1 | SF | 4 |
| S85 | 12/3/03 | 8/18/03 | 10/6/84 | 3.5 | 18.9 | M | F | LRD | 42.8 | SF | 2 |
| S86 | 2/16/04 | 8/18/03 | 10/6/84 | 6.0 | 18.9 | F | F | LRD | 42.8 | SF | 2 |
| S87 | 5/7/04 | 3/30/04 | 6/14/86 | 1.2 | 17.8 | M | F | CAD | 42.3 | SB | 1 |
| S88 | 6/23/04 | 3/30/04 | 7/9/83 | 2.8 | 20.7 | F | M | LRD | 50.1 | SB | 2 |
| S89 | 6/28/04 | 3/6/02 | 8/23/86 | 27.7 | 15.5 | F | F | LRD | 42.0 | SB | 4 |
| S90 | 6/28/04 | 3/7/04 | 8/4/85 | 3.7 | 18.6 | M | M | CAD | 25.1 | SF | 1 |
| S91 | 9/24/04 | 8/18/03 | 10/6/84 | 13.2 | 18.9 | M | F | LRD | 42.8 | SF | 2 |
| S92 | 10/26/04 | 4/29/04 | 2/20/86 | 5.9 | 18.2 | F | 0 | CAD | 14.2 | SF | 1 |
| S93 | 12/13/04 | 9/20/04 | 12/16/02 | 2.8 | 1.8 | M | M | LRD | 22.0 | SF | 4 |
| S94 | 12/17/04 | 10/4/04 | 5/7/86 | 2.4 | 18.4 | M | F | LRD | 50.6 | SF | 4 |
| S95 | 1/12/05 | 10/11/04 | 11/4/97 | 3.0 | 6.9 | M | F | LRD | 43.0 | SF | 2 |
| S96 | 6/10/05 | 3/21/05 | 7/31/88 | 2.7 | 16.6 | M | F | LRD | 47.0 | SF | 3 |
| S97 | 8/2/05 | 5/2/05 | 11/15/90 | 3.0 | 14.5 | F | M | LRD | 47.0 | SF | 3 |
| S98 | 8/16/05 | 8/10/05 | 10/30/86 | 0.2 | 18.8 | F | M | CRD | 19.0 | SB | 2 |
| S99 | 8/23/05 | 8/23/04 | 9/26/97 | 12.0 | 6.9 | F | F | LRD | 37.8 | SB | 4 |
| S100 | 10/11/05 | 7/10/05 | 12/10/87 | 3.0 | 17.6 | M | M | CRD | 37.0 | SF | 2 |
| S101 | 11/11/05 | 8/10/05 | 10/30/86 | 3.0 | 18.8 | F | F | CAD | 19.0 | SB | 2 |
| S102 | 11/14/05 | 5/16/05 | 7/31/89 | 6.0 | 15.8 | F | M | LRD | 38.5 | SB | 4 |
| S103 | 12/12/05 | 6/17/05 | 6/5/86 | 5.8 | 19.0 | M | M | LRD | 47.0 | SF | 3 |
| S104 | 3/23/06 | 3/21/05 | 7/31/88 | 12.0 | 16.6 | M | F | LRD | 47.1 | SF | 3 |
| S105 | 4/11/06 | 10/15/05 | 6/8/88 | 5.8 | 17.4 | M | F | CAD | 20.0 | SB | 1 |
| S106 | 4/6/06 | 4/6/05 | 8/22/90 | 12.0 | 14.6 | M | M | LRD | 43.0 | SB | 3 |
| S107 | 5/23/06 | 11/27/05 | 3/26/87 | 5.8 | 18.7 | F | M | CAD | 14.0 | SB | 0 |
| S108 | 7/21/06 | 4/24/06 | 4/25/05 | 2.9 | 1.0 | F | M | LRD | 28.1 | SF | 3 |
| A70 | 6/4/03 | 9/9/02 | 9/21/85 | 8.8 | 17.0 | M | M | LRD | 39.0 | SF | 5 |
| A71 | 9/12/03 | 4/22/98 | 2/2/86 | 64.6 | 12.2 | M | F | LRD | 41.0 | SB | 4 |
| A72 | 10/10/03 | 10/10/01 | 8/25/89 | 23.9 | 12.1 | M | M | LRD | 34.1 | SB | 2 |
| A73 | 8/27/04 | 9/1/99 | 11/15/87 | 59.7 | 11.8 | F | M | LRD | 37.7 | SB | 5 |
| A74 | 9/26/03 | 8/5/02 | 3/14/91 | 13.7 | 11.4 | F | M | LRD | 11.0 | SF | 3 |
| A75 | 12/30/04 | 3/30/04 | 7/9/83 | 9.0 | 20.7 | F | M | CAD | 50.1 | SB | 2 |
| A76 | 5/9/05 | 8/20/04 | 4/28/95 | 8.6 | 9.3 | M | F | CAD | 9.1 | SF | 5 |
| A77 | 6/16/05 | 6/28/04 | 11/13/02 | 11.6 | 1.6 | F | F | LRD | 42.0 | SB | 3 |
| A78 | 6/28/05 | 8/2/04 | 2/1/89 | 10.8 | 15.5 | M | F | LRD | 19.0 | SF | 2 |
| A79 | 7/29/05 | 5/9/05 | 7/6/02 | 2.7 | 2.8 | M | M | LRD | 48.0 | SF | 2 |
| A80 | 8/10/05 | 8/20/04 | 4/28/95 | 11.6 | 9.3 | M | F | CAD | 9.1 | SF | 5 |
| A81 | 9/27/05 | 3/30/04 | 7/9/83 | 17.9 | 20.7 | F | M | LRD | 50.1 | SB | 2 |
| A82 | 10/1/05 | 11/27/00 | 6/1/96 | 58.0 | 4.5 | M | M | LRD | 38.0 | SF | 3 |
| A83 | 9/29/05 | 9/23/05 | 12/12/88 | 0.2 | 16.8 | M | F | LRD | 49.0 | SF | 0 |
| A84 | 10/24/05 | 10/17/05 | 6/24/91 | 0.2 | 14.3 | M | M | LRD | 36.0 | SF | 1 |
| A85 | 11/17/05 | 10/21/05 | 6/23/88 | 0.9 | 17.3 | F | M | CAD | 14.0 | SB | 0 |
| A86 | 11/21/05 | 10/11/04 | 11/4/97 | 13.3 | 6.9 | M | F | LRD | 43.0 | SF | 2 |
| A87 | 11/22/05 | 10/3/05 | 12/11/90 | 1.6 | 14.8 | F | F | LRD | 38.0 | SB | 2 |
| A88 | 12/2/05 | 10/17/05 | 6/24/91 | 1.5 | 14.3 | M | M | LRD | 36.0 | SF | 1 |
| A89 | 1/14/06 | 10/10/01 | 8/25/89 | 51.0 | 12.1 | M | M | LRD | 34.1 | SB | 2 |
| A90 | 4/6/06 | 10/16/05 | 11/14/90 | 5.6 | 14.9 | M | F | CAD | 17.0 | SB | 0 |
| A91 | 5/12/06 | 5/4/06 | 1/3/90 | 0.3 | 16.3 | M | F | LRD | 43.0 | SF | 2 |
| A92 | 5/25/06 | 11/19/05 | 10/26/94 | 6.1 | 11.1 | F | M | CAD | 16.0 | SB | 5 |
| A93 | 5/30/06 | 8/28/03 | 9/14/95 | 33.0 | 8.0 | F | F | CAD | 4.0 | SB | 1 |
| A94 | 5/31/06 | 7/10/05 | 12/10/87 | 10.7 | 17.6 | M | M | CAD | 37.1 | SF | 2 |
| A95 | 7/17/06 | 1/26/06 | 4/13/95 | 5.6 | 10.8 | M | F | LRD | 33.0 | SF | 2 |
| A96 | 7/27/06 | 4/12/06 | 1/11/92 | 3.5 | 14.3 | M | F | LRD | 44.0 | SF | 4 |
| A97 | 9/29/06 | 3/28/06 | 8/21/02 | 6.1 | 3.6 | M | M | CAD | 15.0 | SF | 4 |
| A98 | 11/3/06 | 7/10/05 | 12/10/87 | 15.8 | 17.6 | M | M | CAD | 37.1 | SF | 2 |
| A99 | 11/2/06 | 5/26/06 | 12/5/01 | 5.2 | 4.5 | F | F | CAD | 26.0 | SF | 0 |
| A100 | 12/22/06 | 6/13/06 | 12/27/89 | 6.3 | 16.5 | F | M | CAD | 26.0 | SB | 1 |
| A101 | 1/9/07 | 11/1/05 | 2/24/86 | 14.2 | 19.7 | F | M | CAD | 17.0 | SB | 0 |
| A102 | 10/24/06 | 10/23/05 | 2/17/89 | 12.0 | 16.7 | M | M | CRD | 25.0 | SB | |
| A103 | 11/6/06 | 4/6/06 | 8/15/04 | 7.0 | 1.6 | M | F | LRD | 29.0 | SB | |
| A104 | 1/26/07 | 6/4/06 | 9/19/87 | 7.7 | 18.7 | M | M | CRD | 30.0 | SF | |
| A105 | 8/8/06 | 8/1/05 | 7/18/95 | 12.2 | 10.0 | F | F | CAD | 32.0 | SB | |
| A106 | 3/27/07 | 8/27/05 | 1/11/88 | 18.9 | 17.6 | M | M | CRD | 26.0 | SF | |
| A107 | 5/1/07 | 10/15/05 | 6/8/88 | 18.5 | 17.4 | M | F | CRD | 20.0 | SB | |
| A108 | 10/4/05 | 10/3/03 | 2/10/92 | 24.0 | 11.6 | F | F | CAD | 16.0 | SF | |
| A109 | 8/29/06 | 3/7/04 | 8/4/85 | 29.7 | 18.6 | M | M | CAD | 25.1 | SF | |
| A01a | 2/20/02 | 11/28/01 | 12/23/86 | 2.8 | 14.9 | M | F | LRD | 44.9 | SF | |
| A02a | 9/6/03 | 10/1/02 | 9/14/89 | 11.1 | 13.0 | M | 0 | CAD | 0.0 | SB | |
| A03a | 1/15/04 | 6/9/03 | 9/14/84 | 7.2 | 18.7 | F | M | LRD | 38.9 | SF | |
| A04a | 1/21/04 | 5/12/03 | 8/9/93 | 8.3 | 9.8 | M | M | LRD | 33.1 | SF | |
| A05a | 6/1/04 | 7/10/96 | 6/20/86 | 94.5 | 10.1 | M | M | LRD | 34.2 | SB | |

Fig. 18 (cont.)

| | | | | | | | | | | |
|---|---|---|---|---|---|---|---|---|---|---|
| A06a | 10/5/04 | 3/30/04 | 7/9/83 | 6.2 | 20.7 | F | M | CAD | 50.1 | SB |
| A07a | 9/30/04 | 6/28/04 | 11/13/02 | 3.1 | 1.6 | F | F | LRD | 42.0 | SB |
| A08a | 12/15/04 | 9/27/04 | 1/2/95 | 2.6 | 9.7 | M | F | LRD | 31.0 | SF |
| A09a | 2/15/05 | 8/20/04 | 4/28/95 | 5.9 | 9.3 | M | F | CAD | 9.1 | SF |
| A10a | 11/21/05 | 8/29/05 | 11/22/90 | 2.8 | 14.8 | M | M | LRD | 42.2 | SF |
| A11a | 1/9/06 | 7/10/05 | 12/10/87 | 6.0 | 17.6 | M | M | CAD | 37.1 | SF |
| A12a | 4/12/06 | 1/8/06 | 3/13/94 | 3.1 | 11.8 | F | F | CAD | 26.8 | SB |
| A13a | 4/6/04 | 1/12/04 | 10/1/02 | 2.8 | 1.3 | F | F | LRD | 32.2 | SF |
| A14a | 12/5/05 | 11/27/05 | 10/16/88 | 0.3 | 17.1 | M | F | CRD | 31.0 | SB |
| A15a | 5/11/06 | 4/13/06 | 1/20/91 | 0.9 | 15.2 | M | M | CAD | 22.0 | SB |
| A16a | 2/24/06 | 1/4/06 | 4/16/90 | 1.7 | 15.7 | M | M | CAD | 23.0 | SB |
| A17a | 8/3/06 | 3/24/06 | 8/10/01 | 4.3 | 4.6 | M | F | CAD | 28.0 | SF |
| A18a | 6/23/04 | 3/28/04 | 1/6/87 | 2.9 | 17.2 | M | F | CAD | 29.0 | SB |
| A19a | 5/25/06 | 7/10/05 | 12/10/87 | 10.5 | 17.6 | M | M | CAD | 37.1 | SF |
| A20a | 8/8/06 | 3/28/06 | 8/21/02 | 4.4 | 3.6 | M | M | CAD | 0.0 | SF |
| A21a | 7/12/06 | 5/26/06 | 12/5/01 | 1.5 | 4.5 | F | F | CRD | 26.0 | SF |
| A22a | 10/30/06 | 11/1/05 | 2/24/86 | 11.9 | 19.7 | F | M | CRD | 17.0 | SB |
| A23a | 5/2/06 | 10/23/05 | 2/17/89 | 6.3 | 16.7 | M | M | CAD | 25.0 | SB |
| A24a | 1/31/06 | 8/1/05 | 7/18/95 | 6.0 | 10.0 | F | F | CRD | 32.0 | SB |
| A25a | 8/29/06 | 8/27/05 | 1/11/88 | 12.0 | 17.6 | M | M | CRD | 26.0 | SF |
| A26a | 10/18/06 | 10/15/05 | 6/8/88 | 12.1 | 17.4 | M | F | CRD | 20.0 | SB |
| A27a | 3/13/06 | 3/7/04 | 8/4/85 | 24.1 | 18.6 | M | M | CRD | 25.1 | SF |
| A01b | 11/11/02 | 11/28/01 | 12/23/86 | 11.4 | 14.9 | M | F | LRD | 44.9 | SF |
| A02b | 6/3/04 | 6/9/03 | 9/14/84 | 11.8 | 18.7 | F | M | LRD | 38.9 | SF |
| A03b | 10/22/04 | 5/12/03 | 8/9/93 | 17.3 | 9.8 | M | M | LRD | 33.1 | SF |
| A04b | 11/22/04 | 7/10/96 | 6/20/86 | 100.2 | 10.1 | M | M | LRD | 34.2 | SB |
| A05b | 4/7/05 | 3/30/04 | 7/9/83 | 12.2 | 20.7 | F | M | CAD | 50.1 | SB |
| A06b | 4/27/05 | 9/27/04 | 1/2/95 | 7.0 | 9.7 | M | F | LRD | 31.0 | SF |
| A07b | 6/13/06 | 7/10/05 | 12/10/87 | 11.1 | 17.6 | M | M | CRD | 37.1 | SF |
| A08b | 6/16/06 | 8/29/05 | 11/23/90 | 9.5 | 14.8 | M | M | LRD | 42.2 | SF |
| A09b | 5/25/06 | 7/10/05 | 12/10/87 | 10.5 | 17.6 | M | M | CAD | 37.1 | SF |
| A10b | 6/26/06 | 10/11/04 | 11/4/97 | 20.4 | 6.9 | M | F | LRD | 43.0 | SF |
| A11b | 9/18/06 | 8/28/97 | 10/26/94 | 108.5 | 2.8 | F | F | CAD | 7.8 | SB |
| A12b | 11/15/05 | 4/6/05 | 2/19/96 | 7.3 | 9.1 | M | M | CRD | 16.0 | SF |
| A13b | 11/17/05 | 10/21/05 | 6/23/88 | 0.9 | 17.3 | F | M | CAD | 14.0 | SB |
| A14b | 11/28/06 | 11/27/05 | 10/16/88 | 12.0 | 17.1 | M | F | CRD | 31.0 | SB |
| A15b | 12/2/06 | 6/5/06 | 8/29/90 | 5.9 | 15.8 | M | M | CRD | 28.0 | SF |
| A16b | 11/28/06 | 1/12/06 | 5/4/88 | 10.5 | 17.7 | F | M | CRD | 18.0 | SF |
| A17b | 1/8/07 | 3/24/06 | 8/10/01 | 9.5 | 4.6 | M | F | CRD | 28.0 | SF |
| A18b | 3/27/07 | 3/21/06 | 2/13/89 | 12.2 | 17.1 | F | M | LRD | 37.0 | SF |
| A19b | 3/24/05 | 3/28/04 | 1/6/87 | 11.8 | 17.2 | M | F | CRD | 29.0 | SB |
| A20b | 8/2/06 | 11/19/05 | 3/20/03 | 8.4 | 2.7 | F | M | CAD | 16.0 | SB |
| A21b | 1/18/07 | 1/26/06 | 4/13/95 | 11.7 | 10.8 | M | F | LRD | 33.0 | SF |
| A22b | 11/27/06 | 5/26/06 | 12/5/01 | 6.1 | 4.5 | F | F | CRD | 26.0 | SF |
| A23b | 6/28/07 | 6/13/06 | 12/27/89 | 12.5 | 16.5 | F | M | CRD | 26.0 | SB |
| A24b | 12/8/06 | 10/23/05 | 2/17/89 | 13.5 | 16.7 | M | M | CRD | 25.0 | SB |
| A25b | 5/14/07 | 4/6/06 | 8/15/04 | 13.2 | 1.6 | M | F | LRD | 29.0 | SB |
| A26b | 9/17/07 | 6/4/06 | 9/19/87 | 15.4 | 18.7 | M | M | CRD | 30.0 | SF |
| A27b | 8/21/07 | 8/27/05 | 1/11/88 | 23.7 | 17.6 | M | M | CRD | 26.0 | SF |
| A28b | 6/25/07 | 10/15/05 | 6/8/88 | 20.3 | 17.4 | M | F | CRD | 20.0 | SB |
| A29b | 1/30/06 | 10/3/03 | 2/10/92 | 27.9 | 11.6 | F | F | CAD | 16.0 | SF |
| A30b | 12/6/06 | 3/7/04 | 8/4/85 | 32.9 | 18.6 | M | M | CAD | 25.1 | SF |

BIOMARKER PANEL FOR DIAGNOSIS AND PREDICTION OF GRAFT REJECTION

This application is a 371 National Phase Application of International Patent Application No. PCT/US2010/020599 filed 11 Jan. 2011, which claims the benefit of priority to U.S. Provisional Patent Application No. 61/145,059 filed 15 Jan. 2009, which is hereby expressly incorporated by reference in its entirety.

GOVERNMENT RIGHTS

This invention was made with Government support under contract AI061739 awarded by the National Institutes of Health. The Government has certain rights in this invention.

BACKGROUND

Transplantation of a graft organ or tissue from a donor to a host patient is a feature of certain medical procedures and treatment protocols. Despite efforts to avoid graft rejection through host-donor tissue type matching, in transplantation procedures where a donor organ is introduced into a host, immunosuppressive therapy is generally required to the maintain viability of the donor organ in the host. However, despite the wide use of immunosuppressive therapy, organ transplant rejection can occur.

Acute graft rejection (AR) of allograft tissue is a complex immune response that involves T-cell recognition of alloantigen in the allograft, co-stimulatory signals, elaboration of effectors molecules by activated T cells, and an inflammatory response within the graft. Activation and recruitment of circulating leukocytes to the allograft is a central feature of this process.

Early detection of AR is one of the major clinical concerns in the care of transplant recipients, including kidney transplant recipients. Detection of AR before the onset of renal dysfunction allows successful treatment of this condition with aggressive immunosuppression. It is equally important to reduce immunosuppression in patients who do not have AR to minimize drug toxicity.

Accordingly, techniques for monitoring for an AR response in a transplant recipient, including predicting, diagnosing and characterizing AR, are of interest in the field. The present invention meets these and other needs.

SUMMARY OF THE INVENTION

Methods are provided for monitoring a subject having a graft for an acute rejection (AR) response, e.g., to predict, to diagnose, and/or to characterize an AR response, including graft survival in a subject. In practicing the subject methods, the expression level of at least one gene in a sample from the subject, e.g., a blood or biopsy sample, is evaluated, e.g., at the nucleic acid and/or protein level, to monitor the subject. Also provided are compositions, systems, kits and computer program products that find use in practicing the subject methods. The methods and compositions find use in a variety of applications.

Aspects of the subject invention include methods of monitoring a subject who has received a graft (e.g., an allograft) for an acute rejection (AR) response including: (a) evaluating the expression level of at least one gene in a sample from the subject to obtain a gene expression result, wherein the at least one gene is selected from the group consisting of: NKTR, MAPK9, DUSP1, PBEF1 (also called NAMPT) and PSEN1; and (b) employing the gene expression result to predict the onset of an AR response, to diagnose an AR response, and/or to characterize an AR response in the subject, thereby monitoring the subject for an AR response. In certain embodiments, the expression level of all of the genes from the above 5-gene group is assessed.

In certain embodiments, the evaluating step further includes evaluating the expression level of additional genes selected from one or more of: CFLAR, RNF-130, IFNGR1, ITGAX and RYBP. In certain embodiments, the expression level of all of the 10 genes listed above is assessed. In certain embodiments, the evaluating step comprises assaying the sample for an expression product of the at least one gene. In certain embodiments, the expression product is a nucleic acid transcript whereas in other embodiments, the expression product is a protein. In certain embodiments, the assessing step comprises an RT-PCR assay. In certain embodiments, the RT-PCR assay is a quantitative RT-PCR assay. In certain embodiments, the sample is a blood sample. In certain embodiments, the allograft is a kidney allograft. In certain embodiments, the gene expression result is employed to predict the occurrence of an AR response between 6 and 3 months in advance. In certain embodiments, the gene expression result is employed to characterize an AR response as a steroid resistant AR response.

Aspects of the invention include methods for determining the identity of a tissue that is being rejected in an AR response, including evaluating the expression level of at least one gene selected from one or more of NKTR, MAPK9, DUSP1, PBEF1 (also called NAMPT), PSEN1, CFLAR, RNF-130, IFNGR1, ITGAX and RYBP in a sample from the subject to obtain a gene expression result and employing the gene expression result to determine the identity of a tissue that is being rejected. The test is applicable not just transplant rejection of numerous tissues, including kidney, heart, liver, lung and intestinal transplants.

Aspects of the subject invention include methods for determining an immunosuppressive regimen for a subject who has received a graft including: (a) evaluating the expression level of at least one gene in a sample from the subject to obtain a gene expression result, wherein the at least one gene is selected from the group consisting of: NKTR, MAPK9, DUSP1, PBEF1 (also called NAMPT) and PSEN1; and (b) employing the gene expression result to determine an immunosuppressive regimen for the subject. In certain embodiments, the expression level of all of the genes from the above 5-gene group is assessed. In certain embodiments, the evaluating step further includes evaluating the expression level of additional genes selected from one or more of: CFLAR, RNF-130, IFNGR1, ITGAX and RYBP. In certain embodiments, the expression level of all of the 10 genes listed above is assessed.

Aspects of the subject invention include systems for monitoring a subject who has received an allograft for an acute rejection (AR) response, the system including: (a) a gene expression evaluation element configured for evaluating the expression level of at least one gene in a sample from the subject to obtain a gene expression result, wherein the at least one gene is selected from the group consisting of: NKTR, MAPK9, DUSP1, PBEF1 (also called NAMPT) and PSEN1; and (b) a phenotype determination element for employing the gene expression result to predict the onset of an AR response, to diagnose an AR response, and/or to characterize an AR response in the subject, thereby monitoring the subject for an AR response. In certain embodiments, the expression level of all of the genes from the above 5-gene group is assessed. In certain embodiments, the gene expression evaluation element comprises at least one reagent for assaying a sample for an expression product of the at least one gene. In certain embodiments, the expression product of the at least one gene is a nucleic acid transcript whereas in other embodiments, the expression product is a protein. In certain embodiments, the gene expression evaluation element comprises PCR primers specific for the at least one gene. In certain embodiments, the gene expression evaluation element is further configured for evaluating the expression level of additional genes selected from one or more of: CFLAR, RNF-130, IFNGR1, ITGAX and RYBP. In certain embodiments, the expression level of all of the 10 genes listed above is assessed. In certain embodiments, the phenotype determination element comprises a reference expression value for the at least one gene.

Aspects of the subject invention include kits for monitoring a subject who has received an allograft for an acute rejection (AR) response, including: (a) a gene expression evaluation element for evaluating expression of at least one gene in a sample to obtain a gene expression result, wherein the at least one gene is selected from the group consisting of: NKTR, MAPK9, DUSP1, PBEF1 (also called NAMPT) and PSEN1; and (b) a phenotype determination element for employing the gene expression result to predict the onset of an AR response, to diagnose an AR response, and/or to characterize an AR response in the subject, thereby monitoring the subject for an AR response. In certain embodiments, the expression level of all of the genes from the above 5-gene group is assessed. In certain embodiments, the gene expression evaluation element is further configured for evaluating the expression level of additional genes selected from one or more of: CFLAR, RNF-130, IFNGR1, ITGAX and RYBP. In certain embodiments, the expression level of all of the 10 genes listed above is assessed. In certain embodiments, the gene expression evaluation element includes PCR primer pairs specific for one or more of the genes noted above (e.g., for use in an RT-PCR assay for gene expression). In certain embodiments, the gene expression evaluation element includes PCR primer pairs specific for all of the 5 genes in the 5 gene group, whereas in other embodiments, the gene expression evaluation element includes PCR primer pairs specific for all 10 genes listed above.

Aspects of the subject invention include computer program products for monitoring a subject who has received an allograft for an acute rejection (AR) response, wherein the computer program product, when loaded onto a computer, is configured to employ a gene expression result from a sample derived from the subject to determine an AR monitoring result and provide the AR monitoring result to a user in a user-readable format, wherein the AR monitoring result is selected from predicting the onset of an AR response, diagnosing an AR response, and/or characterizing an AR response in the subject, wherein the gene expression result includes expression data for one or more genes selected from: NKTR, MAPK9, DUSP1, PBEF1 and PSEN1. In certain embodiments, the expression result includes expression data for all of the genes from the above 5-gene group. In certain embodiments, the expression result includes expression data for additional genes selected from one or more of: CFLAR, RNF-130, IFNGR1, ITGAX and RYBP. In certain embodiments, the expression result includes expression data for all of the 10 genes listed above.

Definitions

For convenience, certain terms employed in the specification, examples, and appended claims are collected here.

"Acute rejection or AR" is the rejection by the immune system of a tissue transplant recipient when the transplanted tissue is immunologically foreign. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery. Generally, acute rejection can be inhibited or suppressed with immunosuppressive drugs such as rapamycin, cyclosporin A, anti-CD40L monoclonal antibody and the like.

"Chronic transplant rejection or CR" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs.

The term "transplant rejection" encompasses both acute and chronic transplant rejection.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1×SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

As used herein, the term "gene" or "recombinant gene" refers to a nucleic acid comprising an open reading frame encoding a polypeptide, including exon and (optionally) intron sequences. The term "intron" refers to a DNA sequence present in a given gene that is not translated into protein and is generally found between exons in a DNA molecule. In addition, a gene may optionally include its natural promoter (i.e., the promoter with which the exons and introns of the gene are operably linked in a non-recombinant cell, i.e., a naturally occurring cell), and associated regulatory sequences, and may or may not have sequences upstream of the AUG start site, and may or may not include untranslated leader sequences, signal sequences, downstream untranslated sequences, transcriptional start and stop sequences, polyadenylation signals, translational start and stop sequences, ribosome binding sites, and the like.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, procaryotic or eukaryotic mRNA, genomic DNA sequences from viral, procaryotic or eukaryotic DNA, and even synthetic DNA sequences. A transcription termination sequence may be located 3' to the coding sequence.

The terms "reference" and "control" are used interchangeably to refer to a known value or set of known values against which an observed value may be compared. As used herein, known means that the value represents an understood parameter, e.g., a level of expression of a marker gene in a graft survival or loss phenotype.

The term "nucleic acid" includes DNA, RNA (double-stranded or single stranded), analogs (e.g., PNA or LNA molecules) and derivatives thereof. The terms "ribonucleic acid" and "RNA" as used herein mean a polymer composed of ribonucleotides. The terms "deoxyribonucleic acid" and "DNA" as used herein mean a polymer composed of deoxyribonucleotides. The term "mRNA" means messenger RNA. An "oligonucleotide" generally refers to a nucleotide multimer of about 10 to 100 nucleotides in length, while a "polynucleotide" includes a nucleotide multimer having any number of nucleotides.

The terms "protein" and "polypeptide" used in this application are interchangeable. "Polypeptide" refers to a polymer of amino acids (amino acid sequence) and does not refer to a specific length of the molecule. Thus peptides and oligopeptides are included within the definition of polypeptide. This term does also refer to or include post-translational modifications of the polypeptide, for example, glycosylations, acetylations, phosphorylation and the like. Included within the definition are, for example, polypeptides containing one or more analogs of an amino acid, polypeptides with substituted linkages, as well as other modifications known in the art, both naturally occurring and non-naturally occurring.

The term "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

Certain abbreviations employed in this application include the following:

AR: Acute Rejection; AZA: Azathioprine; BKV: BK Virus; CMV: Cytomegalovirus; CSA: cyclosporine A; DSA: Donor Specific Antibodies; EBV: Epstein-Barr virus; FDR: false discovery rate; FK: FK506; HCT: Hematocrit; LRD: living related donors; MMF: Mycophenolate Mofetil; PBL: Peripheral Blood Leukocytes; PAM: Prediction Analysis of Microarrays; PRA: Panel Reactive Antibody; Q-PCR: quantitative real time polymerase chain reaction; ROC: Receiver Operating Characteristic; SAM: Significance Analysis of Microarrays; STA: stable; SNS: patients from the NIH-CCTPT U01 funded randomized multicenter pediatric renal transplant steroid-based vs. steroid-free transplantation study (SNS01); WBC: White blood cell.

BRIEF DESCRIPTION OF THE FIGURES

FIG. 3. Receiver Operating Characteristic (ROC) Curve. Using logistic regression model analysis, a prediction model was generated from 5 gene Q-PCR expression data of independent samples (Validation Set1). The specificity and sensitivity of the model is shown by the ROC score=95.2%. The regression model was applied to an independent sample set (Validation set 2), where the expression of 5 genes clearly separates AR from STA (unsupervised clustering), and the differentially expressed 5 genes are significantly different in AR when comparing to STA ($p<0.02$).

FIG. 4. Prediction of Acute Rejection by Blood Sampling for the 5 Gene-Set Prior to Clinical Graft Dysfunction. The regression model was applied to samples sequentially collected from patients in the STA sample set (FIG. 4A), at various times in the first 2 years post-transplantation, to evaluate the probability of prediction as AR at different times after transplantation. The STA samples were grouped to samples collected within 0 to 3 months, within 3 to 6 months, within 6 to 12 months and within 12 to 24 months post transplantation. Each of the blood samples had a paired biopsy to confirm absence of AR in the graft at the time of blood sample collection. The mean and standard error of AR probability was calculated for all STA samples using the coordinated expression of the 5 gene-set at different times after kidney transplantation. As seen, the likelihood of any of the STA samples being predicted as AR, at any time post-transplantation, was less than 50%. There were 2 misclassified STA samples (S99 with an AR probability score of 58% and S88 with an AR prediction score of 72%; see FIG. 9). Both patients with misclassified STA samples have gone on to develop biopsy proven AR within 6 months of the blood sampling. In the right panel (FIG. 4B), the mean and standard error of AR probability is shown for blood samples collected at the time of biopsy proven AR, as well as for samples collected (as part of protocol sample collection) within 1-3 months prior and 3-6 months prior to the AR sample (preAR). As seen, the probability of classification of the blood sample as AR (generally 75-100%), is in strong agreement with the biopsy diagnosis of AR. After intensification of immunosuppression at AR diagnosis (steroid pulsing or antibody), the AR prediction probability falls, demonstrating that the AR prediction probability of the 5 gene-set signature is reduced by augmenting immunosuppression. The AR prediction probability for all samples in the AR set, is significantly higher at all preAR, AR and postAR samples, than any of the STA samples ($p<0.001$), suggesting that patients who develop AR may have a higher immune activation threshold than patients who never develop AR after transplantation.

FIG. 5 provides Venn diagrams showing the significant genes for AR within each discovery platform and the overlapping significant genes in bold font, as ascertained by SAM ($q<10\%$) across sample preparations (A) or across different microarray platforms (B).The overlapping 525 genes (double underline) are statistically significantly (Hypergeometric test; $p<0.001$) regulated in AR, compared to STA samples and are common to AR, irrespective of hybridization to different array platforms are the use of different methods of peripheral blood collection.

FIG. 6A shows a list of genes and ABI probe ID for genes assayed using Q-PCR. FIG. 6B shows normalized expression values for 10-genes by Q-PCR across 34 blood samples in the verification set (17 AR, 17STA).

FIG. 7 is a summary of gene expression values on array and Q-PCR across the 34 samples in the verification set for 3 genes indicated in the literature as differentially expressed in AR.

FIG. 8 shows normalized expression values for 10 genes across 42 independent blood samples (21 AR and 21 STA) in validation set 1 by Q-PCR.

FIG. 9 shows normalized expression values for 5 genes across 64 independent blood samples (32 AR and 32 STA) in validation set 2 by Q-PCR.

FIG. 10 compares different classification models for AR across the 10 gene set (top panel) and 5 gene set (bottom panel).

FIG. 11 shows the 18 demographic and clinical Confounders examined for all Q-PCR experiments.

FIG. 12 shows results of Pearson correlation and t-test (as appropriate) to determine any influence of the 18 parameters in FIG. 11 as potential confounders for expression of the 5-genes set.

FIG. 14 shows the correlation between biopsy Banff grade, Peritubular C4d positivity and humoral vs. cellular AR and the AR prediction probability.

FIG. 16 shows biological relevance analysis for the overlapping 525 genes across the 3 array platforms using Ingenuity System (IPA; 2008).

FIG. 18 shows a table cross-referencing the samples and assays performed.

DESCRIPTION OF THE SPECIFIC EMBODIMENTS

Figure 1:
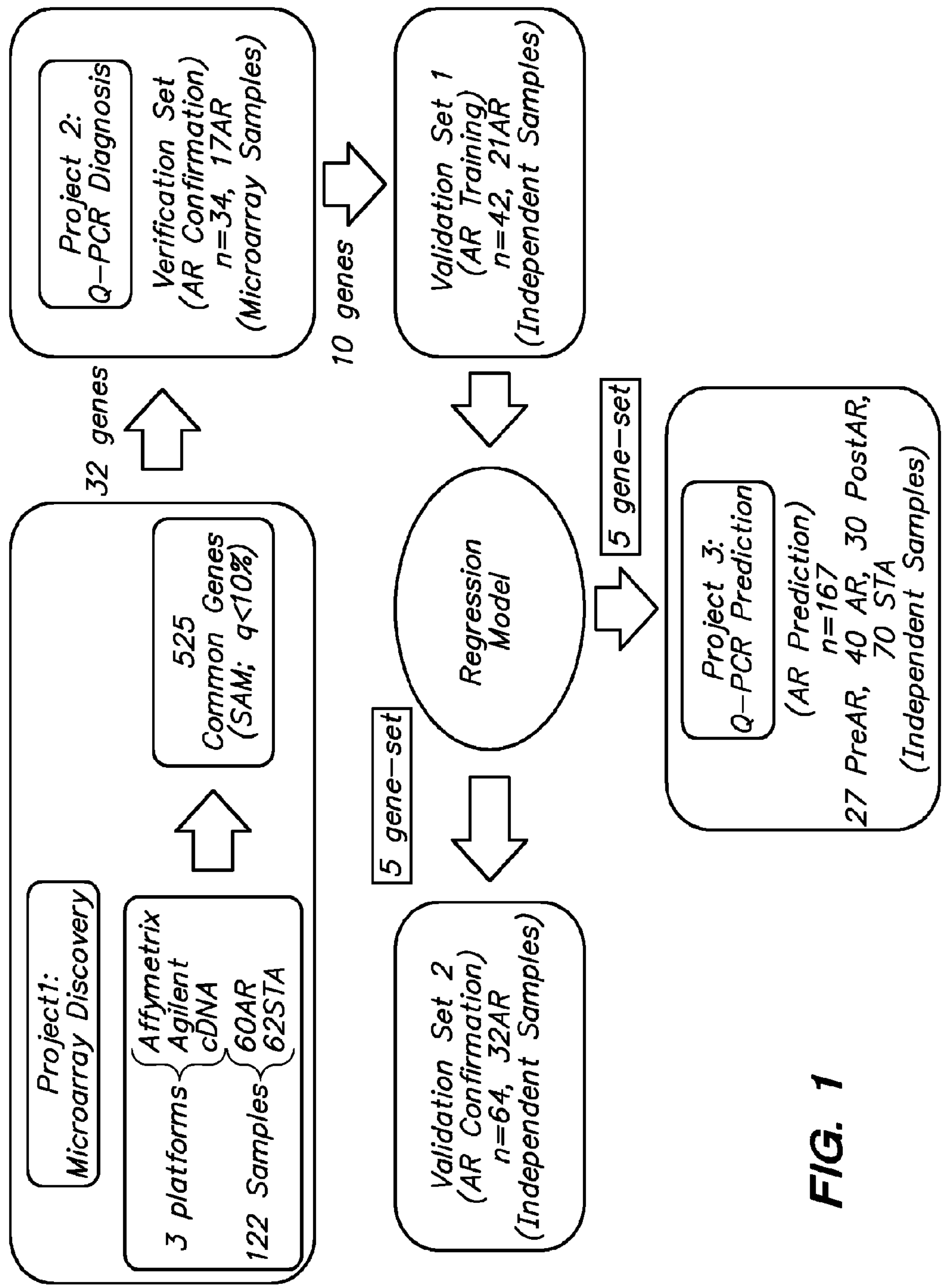
FIG. 1. Summary of Study Design. The present study was divided into 2 specific parts: In part 1 of the study: we conducted cross sectional microarray analysis of peripheral blood samples on 3 different microarray platforms—the Affymetrix, the Agilent and the cDNA arrays. Array data generated from the 3 platforms were compared by mapping the transcripts to Human Gene Organization (HUGO) gene names. Appropriate normalization procedures were applied to each dataset followed by SAM analysis for identification of genes regulated significantly in AR, using a common significance threshold (FDR<10%). 525 genes were common among all differentially expressed AR specific genes across the 3 platforms. A 32 gene-set was selected for initial verification on 34 samples (Verification Set) chosen from the samples used on the microarrays. Of 32 genes tested, the 10 most significant genes ($p<0.03$) were further validated on 42 independent samples (Validation Set1). A regression model was generated using the expression of 5 most significant genes from Validation Set 1. This model was then applied to the second independent set of 64 samples (Validation Set 2) for true AR classification. In Part 2 of the study, we performed longitudinal of 5-gene Q-PCR analysis of paired blood samples collected before (preAR; n=27) and after AR (postAR; n=30), in which the regression model was applied to 57 serial AR samples.

Methods are provided for monitoring a subject having a graft for an acute rejection (AR) response, e.g., to predict, to diagnose, and/or to characterize an AR response. In practicing the subject methods, the expression level of at least one gene in a sample from the subject, e.g., a blood or biopsy sample, is evaluated, e.g., at the nucleic acid and/or protein level, to monitor the subject. Also provided are compositions, systems, kits and computer program products that find use in practicing the subject methods. The methods and compositions find use in a variety of applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the subject invention is directed to methods of monitoring for an AR response in a subject, as well as reagents and kits for use in practicing the subject methods. In further describing the invention, the subject methods are described first, followed by a review of the reagents and kits for use in practicing the subject methods.

Methods of Monitoring for an Acute Rejection Response

As reviewed above, the subject invention provides methods for monitoring a subject who has received a graft for an AR response. In certain embodiments, a subject is monitored to predict if an AR response will occur, where the method can predict a AR from between 6 and 3 months prior to the occurrence of an AR response. In certain embodiments, a subject is monitored to determine whether there is an ongoing AR response. In certain embodiments, a subject is monitored to characterize an AR response that is or has occurred, e.g., to determine the severity and/or class of a previous AR response, e.g., whether an AR response is/was a steroid resistant AR response.

In certain embodiments, the subject invention includes methods for determining the identity of a tissue that is being rejected in an AR response. Aspects of the subject invention further include methods for determining an immunosuppressive regimen for a subject who has received a graft, e.g., an allograft.

As such, certain embodiments of the invention provide methods of evaluating, e.g., in terms of predicting, graft survival in a subject comprising a graft. For example, the subject methods can be used to determine whether a subject will mount an AR response to a graft that, in the absence of effective immunosuppressive intervention, will result in loss of the graft tissue. As such, the subject invention provides methods of evaluating whether a graft in a transplant patient or subject will survive or be lost. In certain embodiments, the methods may be viewed as methods of determining whether a transplant subject has a graft survival phenotype, i.e., a phenotype in which the graft will survive. A graft survival phenotype is a phenotype characterized by the presence of long-term graft survival. By "long-term" graft survival is meant graft survival for at least about 5 years beyond current sampling, despite the occurrence of one or more prior episodes of AR. In certain embodiments, graft survival is determined for patients in which at least one episode of acute rejection (AR) has occurred. As such, these embodiments are methods of determining or predicting graft survival following AR. Graft survival is determined or predicted in certain embodiments in the context of transplant therapy, e.g., immunosuppressive therapy, where immunosuppressive therapies are known in the art. In yet other embodiments, methods of determining the class and/or severity of acute rejection (and not just the presence thereof) are provided.

As in known in the transplantation field, a graft organ, tissue or cell(s) may be allogeneic or xenogeneic, such that the grafts may be allografts or xenografts. Organs and tissues of interest include, but are not limited to: skin, heart, kidney, liver, bone marrow, and other organs.

In practicing the subject methods, a subject or patient sample, e.g., cells or collections thereof, e.g., tissues, is assayed to monitor for an AR response in the host. Accordingly, the first step of the subject methods is to obtain a suitable sample from the subject or patient of interest, i.e., a patient having at least one graft, e.g., allograft.

The sample is derived from any initial suitable source, where sample sources of interest include, but are not limited to, many different physiological sources, e.g., cerebro-spinal fluid (CSF), urine, saliva, tears, tissue derived samples, e.g., homogenates (such as biopsy samples of the transplanted tissue or organ (including, but not limited to kidney, heart, lung biopsies)), and blood or derivatives thereof.

In certain embodiments, a suitable initial source for the patient sample is a blood sample. As such, the sample employed in the subject assays of these embodiments is generally a blood-derived sample. The blood-derived sample may be derived from whole blood or a fraction thereof, e.g., serum, plasma, cellular fraction, etc., where in certain embodiments the sample is derived from blood cells harvested from whole blood. Of particular interest as a sample source are peripheral blood mononuclear cells/lymphocytes (PBMCs/PBLs). Any convenient protocol for obtaining such samples may be employed, where suitable protocols are well known in the art (e.g., density gradient fractionation of a whole blood sample) and a representative protocol is reported in the Experimental Section, below.

In practicing the subject methods, the sample is assayed to obtain an expression level evaluation, e.g., expression profile, for one or more genes selected from Table 1, where the term expression profile is used broadly to include a genomic expression profile, e.g., an expression profile of nucleic acid transcripts, e.g., mRNAs, of the one or more genes of interest, or a proteomic expression profile, e.g., an expression profile of one or more different proteins, where the proteins/polypeptides are expression products of the one or more genes of interest. As such, in certain embodiments the expression level of only one gene in Table 1 is evaluated. In yet other embodiments, the expression level of two or more genes from Table 1 is evaluated, e.g., 3, 4 or all 5 genes in Table 1. In certain embodiments, the expression level of one or more additional gene other than those listed in Table 1 is also evaluated, where in certain embodiments, the additional gene(s) is selected from those listed in Table 2. It is noted here that an expression profile that includes an evaluation of the expression level of any combination of genes in Tables 1 and 2 finds use in monitoring a subject having or being predisposed to develop an AR response in the engrafted tissue, including evaluating the expression of all 10 genes listed in Tables 1 and 2.

TABLE 1

5 genes whose expression level can be used to monitor AR in a subject having an allograft.

| Gene Symbol | Gene Name | NCBI GeneID No. |
|---|---|---|
| DUSP1 | dual specific kinase 1 | 1843 |
| MAPK9 | mitogen-activated protein kinase | 5601 |
| NKTR | natural killer-tumor recognition sequence | 4820 |
| PBEF1 (or NAMPT) | pre-B cell colony enhancing factor | 10135 |
| PSEN1 | presenilin 1 | 5663 |

TABLE 2

5 additional genes whose expression level can be used to monitor AR in a subject having an allograft.

| Gene Symbol | Gene Name | NCBI GeneID No. |
|---|---|---|
| CFLAR | caspase 8 and FADD-like apoptosis regulator | 8837 |
| IFNGR1 | interferon gamma receptor 1 | 3459 |
| ITGAX | Integrin alpha X | 3687 |
| RNF130 | ring finger protein 130 | 55819 |
| RYBP | ring 1 and YY1 binding protein | 23429 |

In the broadest sense, the expression evaluation may be qualitative or quantitative. As such, where detection is qualitative, the methods provide a reading or evaluation, e.g., assessment, of whether or not the target analyte, e.g., nucleic acid or other expression product (e.g., protein), is present in the sample being assayed. In yet other embodiments, the methods provide a quantitative detection of whether the target analyte is present in the sample being assayed, i.e., an evaluation or assessment of the actual amount or relative abundance of the target analyte, e.g., nucleic acid in the sample being assayed. In such embodiments, the quantitative detection may be absolute or, if the method is a method of detecting two or more different analytes, e.g., target nucleic acids, in a sample, relative. As such, the term "quantifying" when used in the context of quantifying a target analyte, e.g., nucleic acid(s), in a sample can refer to absolute or to relative quantification. Absolute quantification may be accomplished by inclusion of known concentration(s) of one or more control analytes and referencing the detected level of the target analyte with the known control analytes (e.g., through generation of a standard curve). Alternatively, relative quantification can be accomplished by comparison of detected levels or amounts between two or more different target analytes to provide a relative quantification of each of the two or more different analytes, e.g., relative to each other. In addition, a relative quantitation may be ascertained using a control, or reference, sample as is commonly done in array based assays as well as in quantitative PCR/RT-PCR analyses (described in further detail below).

As noted above, genes/proteins that find use in monitoring a subject for an AR response, i.e., genes/proteins that are differentially expressed or present at different levels in subjects that have had, are currently having or will have an AR episode, are shown ion Tables 1 and 2. Note that for the genes in these tables, detailed information, including precise sequence information, can be determined through the NCBI Entrez Gene database located at the website http(colon)//www(dot)ncbi.nlm.nih(dot)gov. The detailed information for each gene is then obtained by selecting "Gene" and searching for the GeneID No. listed in these tables.

In certain embodiments, additional genes beyond those listed in Tables 1 and 2 may be assayed, and include other genes whose expression level/pattern can be used to determine an AR response as well as genes whose expression level/pattern can be used to evaluate additional transplant characteristics, including but not limited to: a graft tolerant phenotype in a subject, chronic allograft injury (chronic rejection) in blood; immunosuppressive drug toxicity or adverse side effects including drug-induced hypertension; age or body mass index associated genes that correlate with renal pathology or account for differences in recipient age-related graft acceptance; immune tolerance markers in whole blood; genes found in literature surveys with immune modulatory roles that may play a role in transplant outcomes. In addition, other array assay function related genes may be evaluated, e.g., for assessing sample quality (3'- to 5'-bias in probe location), sampling error in biopsy-based studies, cell surface markers, and normalizing genes for calibrating hybridization results (exemplary genes in these categories can be found in U.S. patent application Ser. No. 11/375,681, filed on Mar. 3, 2006, which is incorporated by reference herein in its entirety).

In certain embodiments, additional genes are evaluated to determine whether a subject who has received an allograft has a graft tolerant phenotype, e.g., as described in provisional patent application 61/089,805, filed on Aug. 18, 2008, which is incorporated herein by reference in its entirety. By graft tolerant phenotype is meant that the subject does not reject a graft organ, tissue or cell(s) that has been introduced into/onto the subject. In other words, the subject tolerates or maintains the organ, tissue or cell(s) that has been transplanted to it. A feature of the graft tolerant phenotype detected or identified is that it is a phenotype which occurs without immunosuppressive therapy, i.e., it is present in a subject that is not undergoing immunosuppressive therapy such that immunosuppressive agents are not being administered to the host.

In these embodiments, in addition to evaluating the one or more genes in Tables 1 and 2 to determine an AR response in a subject having an allograft, one or more genes selected from Tables 3 and 4 below are also evaluated to determine whether a subject has a graft tolerant phenotype. Evaluation of any combination of genes in Tables 3 and 4 find use in such embodiments, including evaluating the expression of all genes listed in either or both of Tables 3 and 4.

TABLE 3

List of 28 genes whose expression levels predict 3 distinct subject classes (HD vs. TOL vs. CAN).

| Symbol | Entrez Gene ID | HD vs. TOL vs. CAN |
|---|---|---|
| TP73 | 7161 | Y |
| CIRBP | 1153 | Y |
| VNN1 | 8876 | Y |
| ATXN1 | 6310 | Y |
| BMP2K | 55589 | Y |
| KIAA1324 | 57535 | Y |
| PLXNC1 | 10154 | Y |
| CCL3 | 6348 | Y |
| WNK1 | 65125 | Y |
| CCL3L3 | 414062 | Y |
| IL6 | 3569 | Y |
| MYL2 | 4633 | Y |
| KIF15 | 56992 | Y |
| IPO13 | 9670 | Y |
| TMEM117 | 84216 | Y |
| KIAA1609 | 57707 | Y |
| RUNX2 | 860 | Y |
| CBFA2T2 | 9139 | Y |
| TUBB4 | 10382 | Y |
| PDPN | 10630 | Y |
| PRPF40B | 25766 | Y |
| NRTN | 4902 | Y |
| KRT17 | 3872 | Y |
| TSPAN7 | 7102 | Y |
| CLGN | 1047 | Y |
| CCL2 | 6347 | Y |
| CENPN | 55839 | Y |
| DOPEY2 | 9980 | Y |

TABLE 4

A gene list (24 genes) of significant differentially expressed either up or down among 3-class (HD vs. SP vs. IN)

| gene | Entrez Gene ID | Z_JT | P value JT | HD->SP->IN | CD3+ | CD4+/CD8+ | CD45+/CD45− |
|---|---|---|---|---|---|---|---|
| AGBL3 | 340351 | −3.50419 | 0.00046 | Y | | | |
| ELAVL1 | 1994 | −3.50419 | 0.00046 | Y | | | |
| NUPL1 | 9818 | −3.39854 | 0.00068 | Y | | | |
| KLF5 | 688 | −3.22245 | 0.00127 | Y | | | |
| MYLIP | 29116 | −3.22245 | 0.00127 | Y | | | |
| ATXN3 | 4287 | −3.15201 | 0.00162 | Y | | | |
| ZDHHC17 | 23390 | −2.97592 | 0.00292 | Y | | | |
| PGM3 | 5238 | −2.87027 | 0.0041 | Y | | | |
| ZMYM2 | 7750 | −2.76462 | 0.0057 | Y | | | |
| FAM110C | 642273 | −2.58853 | 0.00964 | Y | | | Naïve |
| OR10J3 | 441911 | 3.25767 | 0.00112 | Y | | | |
| SSX3 | 10214 | 3.25767 | 0.00112 | Y | | | |
| GNG13 | 51764 | 3.29289 | 0.00099 | Y | | | |
| KIAA1751 | 85452 | 3.3281 | 0.00087 | Y | | | |
| RGMA | 56963 | 3.36332 | 0.00077 | Y | | | |
| IL1F8 | 27177 | 3.43376 | 0.0006 | Y | | | |
| GPHA2 | 170589 | 3.53941 | 0.0004 | Y | | | |
| MKL2 | 57496 | 3.57463 | 0.00035 | Y | | | |
| TRPV1 | 7442 | 3.64507 | 0.00027 | Y | | | |
| KRTAP13-1 | 140258 | 3.75072 | 0.00018 | Y | | | |
| NOTCH4 | 4855 | 3.78594 | 0.00015 | Y | | | |

TABLE 4-continued

A gene list (24 genes) of significant differentially expressed either up or down among 3-class (HD vs. SP vs. IN)

| gene | Entrez Gene ID | Z_JT | P value JT | HD->SP->IN | CD3+ | CD4+/CD8+ | CD45+/CD45− |
|---|---|---|---|---|---|---|---|
| OR13C4 | 138804 | 3.82116 | 0.00013 | Y | | | |
| KCNE1 | 3753 | 3.96203 | 0.00007 | Y | | | |

In certain embodiments, the expression profile obtained is a genomic or nucleic acid expression profile, where the amount or level of one or more nucleic acids in the sample is determined, e.g., the nucleic acid transcript of the gene of interest. In these embodiments, the sample that is assayed to generate the expression profile employed in the diagnostic methods is one that is a nucleic acid sample. The nucleic acid sample includes a plurality or population of distinct nucleic acids that includes the expression information of the phenotype determinative genes of interest of the cell or tissue being diagnosed. The nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as is, amplified, employed to prepare cDNA, cRNA, etc., as is known in the differential expression art. In certain embodiments, the sample is prepared from a cell or tissue harvested from a subject to be diagnosed, e.g., via biopsy of tissue, using standard protocols, where cell types or tissues from which such nucleic acids may be generated include any tissue in which the expression pattern of the to be determined phenotype exists, including, but not limited to, peripheral blood lymphocyte cells, etc., as reviewed above.

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array-based gene expression profile generation protocols. In certain embodiments, such applications are hybridization assays in which a nucleic acid array that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptosome), may be both qualitative and quantitative.

Alternatively, non-array based methods for quantitating the levels of one or more nucleic acids in a sample may be employed, including quantitative PCR, real-time quantitative PCR, and the like. (For general details concerning real-time PCR see Real-Time PCR: An Essential Guide, K. Edwards et al., eds., Horizon Bioscience, Norwich, U.K. (2004)).

Where the expression profile is a protein expression profile, any convenient protein quantitation protocol may be employed, where the levels of one or more proteins in the assayed sample are determined. Representative methods include, but are not limited to: proteomic arrays, flow cytometry, standard immunoassays (e.g., ELISA assays, western blots), protein activity assays, including multiplex protein activity assays, etc.

Following obtainment of the expression data, or expression profile, from the sample being assayed, the expression profile is analyzed. In certain embodiments, analysis includes comparing the expression profile with a reference or control profile to monitor the subject from which the sample was obtained/derived for an AR episode. The terms "reference" and "control" as used herein mean a standardized pattern of gene expression or levels of expression of certain genes to be used to interpret the expression signature of a given patient with respect to an AR response. The reference or control profile may be a profile that is obtained from a cell/tissue known to have the desired phenotype, e.g., having an AR phenotype, and therefore may be a positive reference or control profile. In addition, the reference/control profile may be from a cell/tissue known to not have the desired phenotype, e.g., an AR negative phenotype (e.g., STA or non-transplanted control), and therefore be a negative reference/control profile.

In certain embodiments, the obtained expression profile is compared to a single reference/control profile to obtain information regarding an AR response. In yet other embodiments, the obtained expression profile is compared to two or more different reference/control profiles to obtain more in depth information regarding the AR phenotype of the assayed cell/tissue. For example, the obtained expression profile may be compared to a positive and negative reference profile to obtain confirmed information regarding whether the cell/tissue has a particular AR phenotype.

The comparison of the obtained expression profile and the one or more reference/control profiles may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above.

The comparison step results in information regarding how similar or dissimilar the obtained expression profile is to the control/reference profile(s), which similarity/dissimilarity information is employed to determine the phenotype of the cell/tissue being assayed and thereby providing a way to monitor AR in the subject. For example, similarity of the obtained gene expression profile with the gene expression profile of a control sample from a subject experiencing an active AR response indicates that the assayed cell/tissue are from a subject experiencing AR. Likewise, similarity of the obtained gene expression profile with the gene expression profile of a control sample from a subject that has not had (or isn't having) an AR episode (e.g., STA) indicates that the assayed cell/tissue are from a subject not experiencing AR.

Depending on the type and nature of the reference/control profile(s) to which the obtained expression profile is compared, the above comparison step yields a variety of different types of information regarding the cell/tissue that is assayed. As such, the above comparison step can yield a positive/negative determination of an ongoing AR response. In many embodiments, the above-obtained information about the cell/tissue being assayed is employed to predict whether a subject will experience an AR response, e.g., within 3 to 6 months from the time of harvesting the sample, and/or to characterize an AR response, e.g., whether an AR response is steroid resistant or sensitive. In certain embodiments, the determination/prediction of AR can be coupled with a determination of additional characteristics of the graft and function thereof. For example, in certain embodiments one can assay for other graft-related pathologies, e.g., chronic rejection (or CAN) and/or drug toxicity (DT) (see, e.g., U.S. patent application Ser. No. 11/375,681, filed on Mar. 3, 2006, which is incorporated by reference herein in its entirety).

The subject methods further find use in pharmacogenomic applications. In these applications, a subject/host/patient is first monitored for AR according to the subject invention, and then treated using a protocol determined, at least in part, on the results of the monitoring. For example, a host may be evaluated for the presence or absence of AR using a protocol such as the diagnostic protocol described in the preceding section. The subject may then be treated using a protocol whose suitability is determined using the results of the monitoring step. For example, where the subject is predicted to have an AR response within the next 3 to 6 months, immunosuppressive therapy can be modulated, e.g., increased or drugs changed, as is known in the art for the treatment/prevention of AR. Likewise, where the subject is predicted to be free of current and near-term AR, the immunosuppressive therapy can be reduced in order to reduce the potential for DT.

In practicing the subject methods, a subject is typically monitored for AR following receipt of a graft or transplant. The subject may be screened once or serially following transplant receipt, e.g., weekly, monthly, bimonthly, half-yearly, yearly, etc. In certain embodiments, the subject is monitored prior to the occurrence of an AR episode. In certain other embodiments, the subject is monitored following the occurrence of an AR episode.

The subject methods may be employed with a variety of different types of transplant subjects. In many embodiments, the subjects are within the class mammalian, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the animals or hosts, i.e., subjects (also referred to herein as patients) are humans.

The methods may be used to monitor a variety of different types of grafts. Grafts of interest include, but are not limited to: transplanted heart, kidney, lung, liver, pancreas, pancreatic islets, brain tissue, stomach, large intestine, small intestine, cornea, skin, trachea, bone, bone marrow, muscle, bladder or parts thereof.

Databases of Expression Profiles of Phenotype Determinative Genes

Also provided are databases of expression profiles of AR responses. Such databases will typically comprise expression profiles of specific tissues from a transplant recipient that are indicative of one or more of: a near-term AR event (within 3 to 6 months), an ongoing AR response, a previous AR response, and a characteristic of an AR response (e.g., steroid resistant/sensitive AR response).

The expression profiles and databases thereof may be provided in a variety of media to facilitate their use (e.g., in a user-accessible/readable format). "Media" refers to a manufacture that contains the expression profile information of the present invention. The databases of the present invention can be recorded on computer readable media, e.g. any medium that can be read and accessed directly by a user employing a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc. Thus, the subject expression profile databases are accessible by a user, i.e., the database files are saved in a user-readable format (e.g., a computer readable format, where a user controls the computer).

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention, e.g., to and from a user. One format for an output means ranks expression profiles possessing varying degrees of similarity to a reference expression profile. Such presentation provides a skilled artisan (or user) with a ranking of similarities and identifies the degree of similarity contained in the test expression profile to one or more references profile(s).

Reagents, Systems and Kits

Also provided are reagents, systems and kits thereof for practicing one or more of the above-described methods. The subject reagents, systems and kits thereof may vary greatly. Reagents of interest include reagents specifically designed for use in production of the above-described expression profiles of AR phenotype determinative genes, i.e., a gene expression evaluation element made up of one or more reagents. The term system refers to a collection of reagents, however compiled, e.g., by purchasing the collection of reagents from the same or different sources. The term kit refers to a collection of reagents provided, e.g., sold, together.

One type of such reagent is an array of probe nucleic acids in which the phenotype determinative genes of interest are represented. A variety of different array formats are known in the art, with a wide variety of different probe structures, substrate compositions and attachment technologies (e.g., dot blot arrays, microarrays, etc.). Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

In certain embodiments, the arrays include probes for at least 1 of the genes listed in Table 1. As such, probes for any combination of genes in Table 1 may be employed. Therefore, in certain embodiments, the number of genes that are from Table 1 that are represented on the array is at least 2, at least 3, at least 4, at least 5, at least 8 or more, including all of the genes listed in Table 1. The subject arrays may include only those genes that are listed in Table 1 or they may include additional genes that are not listed in Table 1, such as probes for genes whose expression pattern can be used to evaluate additional transplant characteristics, including but not limited to: chronic allograft injury (chronic rejection) in blood; immunosuppressive drug toxicity or adverse side effects including drug-induced hypertension; age or body mass index associated genes that correlate with renal pathology or account for differences in recipient age-related graft acceptance; immune tolerance markers in whole blood; genes found in literature surveys with immune modulatory roles that may play a role in transplant outcomes; as well as other array assay function related genes, e.g., for assessing sample quality (3'- to 5'-bias in probe location), sampling error in biopsy-based studies, cell surface markers, and normalizing genes for calibrating hybridization results; and the like. Where the subject arrays include probes for such additional genes, in certain embodiments the number % of additional genes that are represented and are not directly or indirectly related to transplantation does not exceed about 50%, usually does not exceed about 25%. In certain embodiments where additional genes are included, a great majority of genes in the collection are transplant characterization genes, where by great majority is meant at least about 75%, usually at least about 80% and sometimes at least about 85, 90, 95% or higher, including embodiments where 100% of the genes in the collection are phenotype determinative genes. Transplant characterization genes are genes whose expression can be employed to characterize transplant function in some manner, e.g., presence of rejection, etc.

Another type of reagent that is specifically tailored for generating expression profiles of phenotype determinative genes is a collection of gene specific primers that is designed to selectively amplify such genes (e.g., using a PCR-based technique, e.g., real-time RT-PCR). Gene specific primers and methods for using the same are described in U.S. Pat. No. 5,994,076, the disclosure of which is herein incorporated by reference.

In one embodiment, one of either the gene specific primers or dNTPs, preferably the dNTPs, will be labeled such that the synthesized cDNAs are labeled. By labeled is meant that the entities comprise a member of a signal producing system and are thus detectable, either directly or through combined action with one or more additional members of a signal producing system. Examples of directly detectable labels include isotopic and fluorescent moieties incorporated into, usually covalently bonded to, a nucleotide monomeric unit, e.g. dNTP or monomeric unit of the primer. Isotopic moieties or labels of interest include 32P, 33P, 35 S, 125 I, and the like. Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum Dye™, fluorescent energy transfer dyes, such as thiazole orange-ethidium heterodimer, TOTAB, etc. Labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like. Labeled nucleic acid can also be produced by carrying out PCR in the presence of labeled primers.

Of particular interest are collections of gene specific primers that have primers for at least 1 of the genes listed in one Table 1, often a plurality of these genes, e.g., at least 2, 4, 8 or more. In certain embodiments, all of genes that are from Table 1 have primers in the collection. The subject gene specific primer collections may include only those genes that are listed in Table 1, or they may include primers for additional genes that are not listed in Table 1, such as probes for genes whose expression pattern can be used to evaluate additional transplant characteristics, including but not limited to: chronic allograft injury (chronic rejection) in blood; immunosuppressive drug toxicity or adverse side effects including drug-induced hypertension; age or body mass index associated genes that correlate with renal pathology or account for differences in recipient age-related graft acceptance; immune tolerance markers in whole blood; genes found in literature surveys with immune modulatory roles that may play a role in transplant outcomes; as well as other array assay function related genes, e.g., for assessing sample quality (3'- to 5'-bias in probe location), sampling error in biopsy-based studies, cell surface markers, and normalizing genes for calibrating hybridization results; and the like. Where the subject arrays include probes for such additional genes, in certain embodiments the number % of additional genes that are represented and are not directly or indirectly related to transplantation does not exceed about 50%, usually does not exceed about 25%. In certain embodiments where additional genes are included, a great majority of genes in the collection are transplant characterization genes, where by great majority is meant at least about 75%, usually at least about 80% and sometimes at least about 85, 90, 95% or higher, including embodiments where 100% of the genes in the collection are phenotype determinative genes.

The systems and kits of the subject invention may include the above-described arrays and/or gene specific primer collections. The systems and kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The subject systems and kits may also include a phenotype determination element, which element is, in many embodiments, a reference or control expression profile that can be employed, e.g., by a suitable computing means, to make an AR phenotype determination based on an “input” expression profile, e.g., that has been determined with the above described gene expression evaluation element. Representative phenotype determination elements include databases of expression profiles, e.g., reference or control profiles, as described above.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

Example I

Methods

Study Design

Patient demographics and clinical data were collected for all recipients providing peripheral blood samples in this study. The mean±standard deviation data for the different study sets (Verification Set, Validation Set 1 and Validation Set 2) is provided in FIG. 11 and Table 1 (below). Within each sample set, the AR and STA phenotypes have matched demographics. To interrogate the performance of blood-based genes for AR diagnosis, irrespective of time post-transplantation, sample study sets were deliberately chosen to have different mean times post-transplantation.

TABLE 1

| | Microarray_Affy | | | qPCR Verification Set | | |
|---|---|---|---|---|---|---|
| Clinical Characteristics | AR (n = 31) | STA (n = 28) | p value | AR (n = 17) | STA (n = 17) | p value |
| Recipients | | | | | | |
| Gender, % females | 34.3% | 51.4% | 0.1 | 34.6% | 50% | 0.3 |
| Mean age, year | 12.0 ± 5.1 | 10.7 ± 6.2 | 0.2 | 11.8 ± 4.7 | 7.8 ± 6.8 | 0.1 |
| Immunosuppression, % SF | 45.7% | 54.1% | 0.5 | 46.2% | 50.0% | 0.8 |
| HLA match | 1.2 ± 1.7 | 1.4 ± 1.1 | 0.7 | 0.8 ± 0.8 | 0.7 ± 1.1 | 0.9 |
| Post-txp time, month | 34.8 ± 40.7 | 23.4 ± 31.2 | 0.1 | 31.1 ± 39.4 | 14 ± 22.4 | 0.1 |
| Donor | | | | | | |
| Donor Source % LRD | 60.0% | 62.2% | 0.9 | 57.7% | 85.7% | 0.1 |
| Gender, % females | 53.1% | 48.7% | 0.7 | 50.0% | 42.9% | 0.7 |
| Mean age, year | 34.9 ± 11.3 | 30.8 ± 11.4 | 0.1 | 33.3 ± 10.9 | 30.6 ± 10.4 | 0.5 |

| | qPCR | | | | | |
|---|---|---|---|---|---|---|
| | Validation Set 1 | | | Validation Set 2 | | |
| Clinical Characteristics | AR (n = 21) | STA (n = 21) | p value | AR (n = 32) | STA (n = 32) | p value |
| Recipients | | | | | | |
| Gender, % females | 31.6% | 42.9% | 0.5 | 33.3% | 43.8% | 0.5 |
| Mean age, year | 11.2 ± 5.9 | 13.5 ± 5 | 0.2 | 12.5 ± 6.2 | 13.9 ± 6.3 | 0.5 |
| Immunosuppression, % SF | 63.1% | 57.1% | 0.7 | 66.7% | 68.8% | 0.9 |
| HLA match | 1.6 ± 1.6 | 0.8 ± 1.0 | 0.1 | 1.6 ± 1.3 | 1.8 ± 0.9 | 0.2 |
| Post-txp time, month | 12.4 ± 17.9 | 10.6 ± 9 | 0.7 | 7.9 ± 5.2 | 6.5 ± 4.4 | 0.4 |

TABLE 1-continued

| | Donor | | | | | |
|---|---|---|---|---|---|---|
| Donor Source % LRD | 31.6% | 61.9% | 0.1 | 55.6% | 75.0% | 0.2 |
| Gender, % females | 31.6% | 57.1% | 0.1 | 44.4% | 50.0% | 0.7 |
| Mean age, year | 26.4 ± 11.8 | 31.1 ± 10.9 | 0.2 | 22.1 ± 11.7 | 37 ± 10.8 | 0.2 |

Values are means ± SD (Standard Deviation).
AR, Acute rejection;
STA, stable;
SF, steriod free;
txp, transplant;
LRD, living related donor This study was undertaken as a sum of 3 projects (FIG. 1): In the first project, we performed cross-sectional microarray analysis of 122 peripheral blood samples collected either as 2.5 ml of whole blood samples (n=106) or as 5 ml of blood (n=16) for isolation of peripheral blood leukocytes (PBL)[7]. Blood samples were collected at a single time point, timed with a biopsy where acute rejection was either confirmed[10], as present (60 AR samples) or absent (62 STA samples). Sample preparation for array hybridization was done following the manufacturers' recommended protocols.

The samples were hybridized to one of 3 microarray platforms: Affymetrix (n=75, the 54K HGU133Plus2 Array), Agilent (n=26, 44K Whole Human Genome oligo Array) or the Lymphochip cDNA array (n=21, 32K cDNA clones). Appropriate probe detection and normalization methods were applied for each microarray platform. Details of sample preparation, array hybridization and analyses[11] [12] [13] [14] are provided in Supplemental Methods (see below). All microarray data files are available in GEO under Accession No. GSE14067.

In the second project, Q-PCR analysis was performed for verification and validation on selected genes from the array studies in project 1. Expression of messenger RNA for the selected candidate genes was measured in each blood sample by Q-PCR using TaqMan Gene Expression Assay products (Applied Biosystems, Foster City, Calif.). 32 genes were selected for Q-PCR verification (see Supplementary Methods/Candidate Gene Selection Criteria for Q-PCR) in 34 samples (17 AR, 17 STA; Verification Set) previously used for microarray, left with adequate quantity and quality residual RNA. Of the 32 genes, the 10 most significant genes were selected for further validation on 42 independent samples (21 AR, 21 STA; Validation Set 1) and an additional 64 independent samples (32 AR, 32 STA; Validation Set 2). We applied various classification models[15] including linear discriminant analysis, 5 different Bayesian models, multilayer perceptron and logistic regression (multinomial and linear) models to the 10 gene-set expression values obtained from Validation Set 1. Each of these models was built using Validation Set 1 and tested on the Validation Set 2 for evaluating their sensitivities, specificities and accuracies. A multinomial logistic regression model using 5 out of the 10 gene-set yielded the best overall performance. The primer list for each of the 10 genes, their corresponding ABI probe IDs, the expression of the 10 most significant genes by Q-PCR, and the comparisons of all classification models used, are all provided in FIGS. 7 to 10.

In the third project, we applied the 5-gene AR diagnosis model for AR prediction modeling on 40 patients who had serially collected peripheral blood samples, collected either before (preAR; n=27 samples) and/or after (postAR; n=30 samples) the AR episode. Longitudinal 5-gene Q-PCR analysis was done on paired preAR blood samples, collected 1 to 6 months prior to the AR episode, to estimate the prediction of AR injury, even at the time of unperturbed graft function. These were the only samples in the study that were not paired with graft biopsies. A similar analysis was done on postAR samples collected 1 to 6 months after treatment of the AR episode (paired with graft biopsies performed to follow-up for AR resolution) to interrogate the effect of intensified immunosuppression on the 5 gene-set signature (FIG. 1).

A first logistic regression model using the 5-genes set is shown in the following equation:

$$\theta = \frac{e^{10.0395+(1.8364*DUSP1)+(-1.9182*MAPK9)+(-1.8939*NKTR)+(4.9901*PBEF1)+(2.124*PSEN1)}}{1+e^{10.0395+(1.8364*DUSP1)+(-1.9182*MAPK9)+(-1.8939*NKTR)+(4.9901*PBEF1)+(2.124*PSEN1)}}$$

A second logistic regression model using a minimal 5-gene set is shown in the following equation:

$$\theta = \frac{e^{-18.6137+(3.8327*DUSP1)+(-5.1524*MAPK9)+(-3.6056*NKTR)+(8.3652*PBEF1)+(3.353*PSEN1)}}{1+e^{-18.6137+(3.8327*DUSP1)+(-5.1524*MAPK9)+(-3.6056*NKTR)+(8.3652*PBEF1)+(3.353*PSEN1)}}$$

The logistic regression model using a minimal 5-gene set based on the Stanford samples is shown in the following equation:

$$\theta = \frac{e^{-17.2226+(1.0735*IFNGR1)+(-7.7795*MAPK9)+(4.2314*PBEF1)+(3.7546*PSEN1)+(2.9103*RNF130)}}{1+e^{-17.2226+(1.0735*IFNGR1)+(-7.7795*MAPK9)+(4.2314*PBEF1)+(3.7546*PSEN1)+(2.9103*RNF130)}}$$

In each equation above, θ is the predicted probability of a given sample belonging to one of the classes (AR or STA). The threshold θ=0.5 was selected for the best sensitivity and specificity, based on the Receiver Operating Characteristic (ROC) curve, to determine whether the predictive class was an AR or STA phenotype. The model was tested in Validation Set 1 and then re-validated in Validation Set 2, for true AR classification. The accuracy of the model was assessed by evaluating the sensitivity, specificity, positive prediction value (PPV) and negative prediction value (NPV) on the test set (Validation set 2). Finally, after confirming the robustness of the model for AR diagnosis, the model was used to predict the probability of AR on paired blood samples, sequentially collected before and after AR.

Statistical and Bioinformatics Analyses

Student t-test was used for establishing the significance for gene expression differences between AR and STA samples by Q-PCR. All differences were considered statistically significant for false discovery rate (FDR)<10%. Data was collected on the following 18 demographic and clinical variables on all samples processed for Q-PCR validation studies: post-transplant time, recipient age, recipient gender, donor gender, donor source, donor age, cytomegalovirus/CMV, Epstein-Barr virus/EBV and BK virus/BKV viremia at sampling, concomitant bacterial infection, presence of donor specific antibodies (DSA) or panel reactive antibodies (PRA), usage of induction therapy, maintenance steroid usage, use of different calcineurin inhibitor drugs (FK506 or cyclosporine A/CSA), use of different anti-metabolites (mycophenolate mofetil/MMF or azathioprine/AZA), the white blood cell (WBC) count and the hematocrit (HCT) levels at the time of blood sampling (FIG. 11). Data was provided for SNSO1 samples by PPD (David Ikle). Pearson correlation and t-test were used, as appropriate, to determine any influence of the 18 parameters as potential confounders for expression of the 5-genes set (FIG. 12). As most samples had paired biopsies for evaluation, samples were divided into 2 groups according to Banff score grades (1=Banff scores≤1A; 2=Banff score≥1B); C4d$^+$ was determined if ≥0% of peritubular capillaries (PTC) had C4d deposits (FIG. 14).

Figure 17:
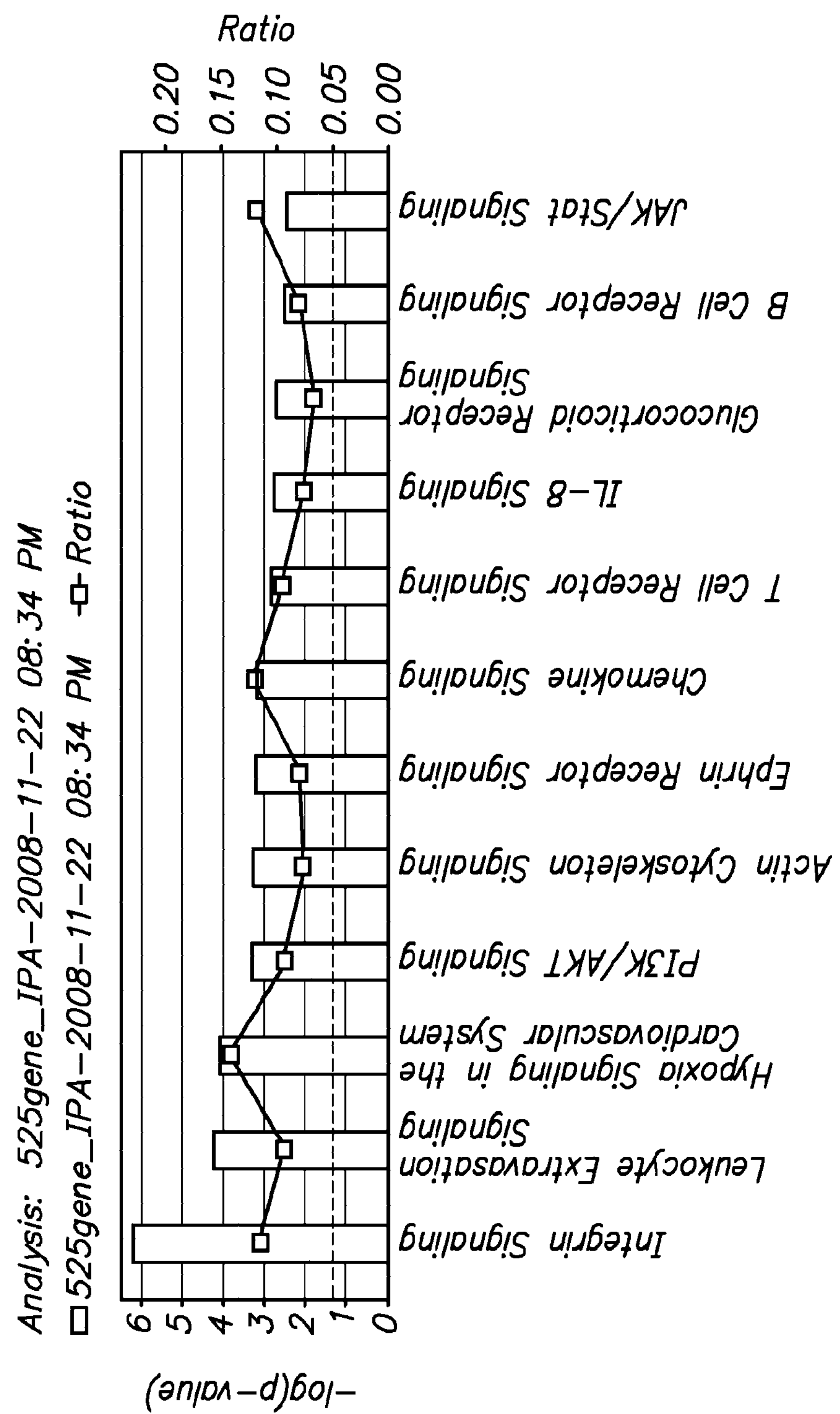
FIG. 17 is a graphical representation of the information shown in FIG. 16.

Biological relevance of the cross-platform 525 gene set was evaluated using the PANTHER classification system (http(colon)//www(dot)pantherdb(dot)org) and Ingenuity Pathway Analysis (IPA; http(colon)//www(dot)ingenuity (dot)com) (see FIGS. 16 and 17). More information is provided in Supplemental Methods.

Results

Significant Genes for AR in Peripheral Blood by Cross-Platform Microarray Analysis Microarray data generated from 3 array platforms were cross-compared, by mapping common and overlapping transcripts to Human Gene Organization (HUGO) gene names. Because each array platform uses different sets of genes, which are represented using different probe IDs, we used AILUN (http(colon)//ailun(dot)stanford(dot)edu)[12] to re-annotate the probe identifiers (IDs) with the current HUGO gene names, which identified 10,357 common genes that were shared across all 3 platforms. We applied supervised, two-class unpaired Significance Analysis of Microarray (SAM[11]) analyses with a common significance threshold of false discovery rate <10% to each of the 3 re-annotated array lists. We identified 9710 genes on the Affymetrix arrays, 8642 genes on the Agilent arrays and 2805 genes on the cDNA arrays as significantly differentially expressed in AR. Despite the large number of significant genes on each platform, only 525 genes were differentially expressed on all 3 platforms (FIG. 5), irrespective of the blood sample collection procedure.

Q-PCR Verification and Validation (Validation Set 1)

Figure 2:
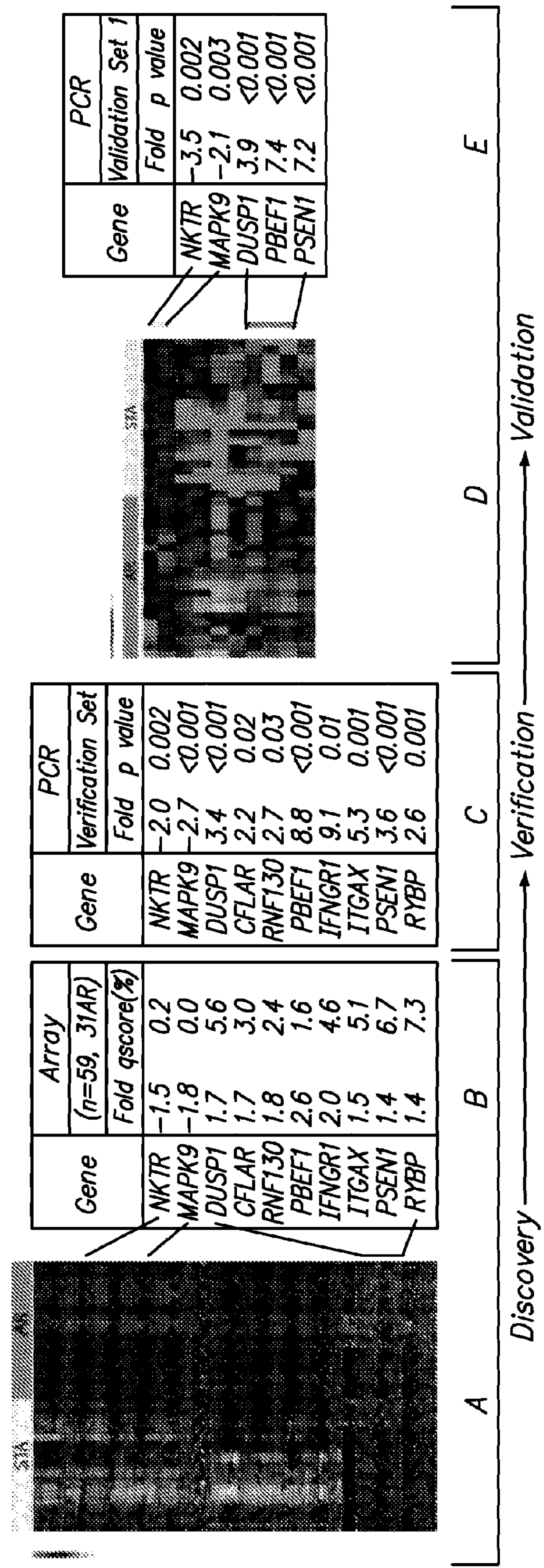
FIG. 2. Verification and Validation of Gene Expression for the 5 Gene-Set. Clustering of arrays from peripheral blood samples across the common 525 gene-set shows clustering of samples by diagnosis phenotype. Clustering of 59 samples run on Affymetrix arrays is shown here (FIG. 2A); clustering of samples by phenotype is seen across the 525 overlapping genes, differentially expressed on all 3 array platforms (see FIG. 5), irrespective of sample collection, processing or multiple clinical confounders. The samples cluster by phenotype (AR or STA) across the 525 genes. Shown here, are representative clustering data for the samples run only on the Affymetrix array. Summarized expression of the selected 10 gene-set is shown as measured on one of the array platforms (Affymetrix) (FIG. 2B). Fold changes and q score from SAM analysis of microarray data from Affymetrix in whole blood samples are shown. The expression of the same 10 genes is shown for the Verification Set of Q-PCR samples (FIG. 2C). The fold change in Q-PCR was the mean differences between AR and STA samples; the significance for expression differences by Q-PCR were determined by T test, where $p<0.05$ was taken to be significant. In the independent validation set of blood samples (Validation Set 1), the expression for the most significant 5 genes is shown. The new blood samples, not used in the array analyses, again segregate by phenotype (AR or STA) across the 5 genes (FIG. 2D). The fold changes and p values of the 5 genes in the samples used in Validation Set 1 are shown in FIG. 2E.

32 genes were selected for initial Q-PCR verification in 34 samples (17 AR, 17 STA) that had also been used on the arrays studies. From this data, the 10 most significant genes (q<10%) were further validated in 42 independent blood samples (Validation Set 1; 21 AR, 21 STA). The expression fold changes of these 10 most significant genes were in agreement with array data, with same direction fold changes and higher signal by Q-PCR than by microarray (FIG. 1), and separation of the samples into AR or STA phenotypes by unsupervised clustering of expression data for the 10-gene set by Q-PCR (FIG. 2). Individual expression data for each gene and each sample is shown in FIG. 6B. For the 3 genes chosen from the AR literature, Q-PCR expression of FOXP3[16] and GRZYB[17 18] were increased in AR compared to STA blood samples (p=0.001, p=0.03 respectively) (FIG. 7), even though these genes were not among the significant gene list from Affymetrix microarrays, and both PFN1[19] and GRZYB were conversely down regulated in AR on the cDNA and Agilent platform respectively, with no statistical difference by Q-PCR between AR and STA samples. Hence none of these 3 genes were used for further cross-validation studies.

Cross-Validation (Validation Set 2) and Prediction Modeling for AR Classification A multinomial logistic regression model, which demonstrated the best performance of the 10 classification models tested (details in FIG. 10), resulted in a minimal 5 gene model for AR prediction with high confidence shown by ROC score=95.2%, when tested on Q-PCR data from the 64 independent samples in Validation Set 2. The 5 gene-set expression shows excellent AR and STA class separation (FIG. 3), with a high AR prediction score with 100% sensitivity, 93.6% specificity, 94.1% positive predictive value (PPV) and 100% negative predictive value (NPV). The only misclassification related to 2 STA samples. Both misclassified STA samples developed clinical AR at 4 and 7 months after the initial sampling for this study, suggesting that the AR prediction of the 5 gene-test maybe more robust than estimated by the prediction model.

Figure 13:
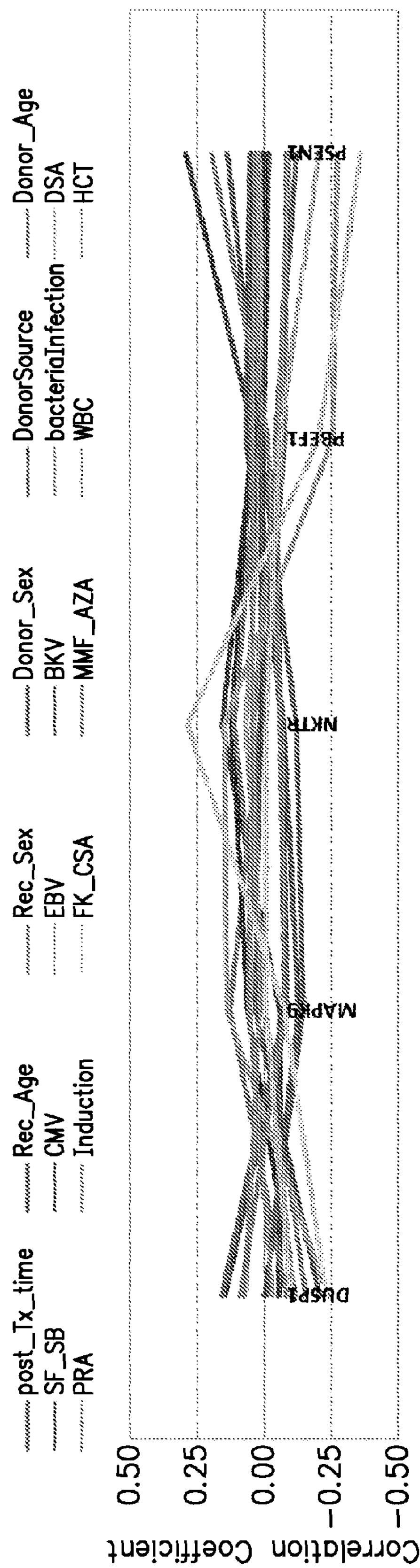
FIG. 13 is a graphical representation of the results in FIG. 12.

Evaluating for Demographic, Clinical and Biopsy Confounders for the 5 Gene-Set for AR Diagnosis To examine if any baseline, or at sampling, demographic, clinical or immunosuppression confounders may drive the segregation of the 5 gene-set prediction score for AR, Pearson correlation coefficients calculated for data collected on 18 different confounders (FIG. 11), showed no confounding effects on the expression of the 5 gene-set (maximum |r|=0.27) (FIGS. 12 and 13). By t-test, DUSP1 and PSEN1 had higher expression (p<0.01) in patients with positive DSA. Similarly, we also examined if the grade or type of rejection had an influence on expression of the 5 gene-set (FIG. 14). No correlation was found between AR probability prediction by the 5 gene-set and Banff scores (r=−0.13), humoral versus cellular rejection (r=0.07), and presence or absence of peri-tubular C4d+ (r=0.2) (FIG. 14). These data support that the coordinated expression the 5 gene-set in peripheral blood can diagnose AR with high confidence, irrespective of the differences in patient characteristics and commonly used immunosuppression choices, rejection timing or the underlying mechanism of rejection injury.

Figures 15D, 15E:
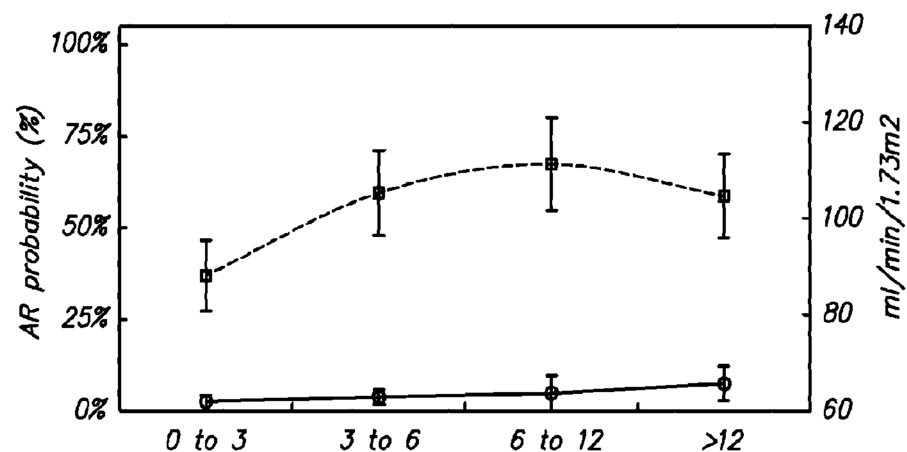
FIG. 15. Panel A shows prediction probability of AR in paired samples collected within 6 months before and after the AR episode. Panel B shows p values comparing the AR prediction score at AR vs. preAR and postAR scores. Panel C is a graphical representation of the data in panel A. Panel D is a graph showing AR probability in STA samples. Panel E shows the data used in the graph shown in panel D.

Prediction of AR Injury Prior to Graft Dysfunction and Clinically Indicated Biopsies We applied the AR regression model built on cross-sectional samples, to 27 preAR blood samples (sequentially collected 1 to 6 month prior to a biopsy proven AR episode, prior to any clinical graft dysfunction), as part of serial blood sampling protocol post-transplantation. Additionally, 70 serial blood samples from 58 unique STA patients, who did not have any AR, collected at the time of protocol biopsies at 1, 3, 6, 12 and 24 months post-transplantation were also profiled by Q-PCR for the 5 gene-set for AR prediction. As shown in FIG. 4, the 5-gene signature from STA samples that were collected at various time points post-transplantation remains "quiescent", with low AR prediction scores and with little change in expression scores over time post-transplantation (FIG. 4A). However, in the AR patient group (FIG. 4B; preAR, AR and postAR patients), the expression level for the 5 gene-set is at a significantly ($p<0.001$) higher level in rejector patients (>50% AR prediction scores in all AR patients, versus <20% in all STA patients), even 6 months prior to an AR episode. This finding suggests that patients who undergo AR episodes after transplantation have an immune activation profile in their peripheral blood that can be measured quantitatively well before a clinically relevant and biopsy documented AR episode. It is noteworthy that the AR prediction score for blood samples examined within 3 months of the rejection episode is equivalent to the sample collected at the time of AR (FIG. 4B), providing a potential window for immunosuppression intensification to mitigate or treat early AR and/or instigate an earlier biopsy. When immunosuppression treatment is intensified at AR (steroid bolus or thymoglobulin in this study), there is a rapid decrement of the 5-gene signature over the next 3 months regardless of AR treatment drug (FIG. 4B). FIG. 15 provides mean AR probabilities along with standard errors and calculated creatinine clearances[20] for each group of samples.

Discussion

The transplant biopsy is the current gold standard for AR diagnosis but is limited by its invasive nature, difficulty in obtaining multiple samples, and often identifying AR only in the presence of advanced tissue injury and clinical graft dysfunction. There is no reliable blood test currently available to diagnose and predict AR, as many clinical confounders, including over-representation of globin genes in whole blood samples, drive expression changes[7], and in the past, robust blood-based AR biomarker identification has been hampered by small sample size, experimental variance[7], concomitant infections and the underlying molecular heterogeneity of tissue rejection injury[1].

As demonstrated above, we have identified a highly stringent gene-set whose expression evaluation in a transplant patient sample (e.g., peripheral blood) can be used to monitor an AR response. This gene set evaluation method proves accurate across multiple different confounders, such as differences in sample preparation, recipient and donor demographics, recipient age, post-transplant time, immunosuppression usage, or concurrent infection. We have validated a minimal set of 5 genes for non-invasive AR diagnosis in 152 independent blood samples. The expression of the 5-gene set is sufficient for prediction of biopsy-proven AR with high confidence levels even 3 months prior to clinical graft dysfunction. Additionally, the expression of the 5-gene set is differentially regulated in rejectors, compared to non-rejectors, up to 7 months prior to a biopsy proven AR episode, indicating that differential regulation of the 5 gene-set in blood can be used as a yardstick for immune activation and risk assessment for future AR. As the 5 gene signature "normalizes" to levels closer to those seen in non-rejector STA patients with intensification of immunosuppression, serial measurement of this gene-set can serve as an immune "barometer" to define an individual patient's immune activation threshold for prediction of AR many months before clinical graft dysfunction. This is an important and critical step towards individualizing immunosuppressive regimens in a transplant recipient.

REFERENCES

1. Sarwal M, Chua M S, Kambham N, et al. Molecular heterogeneity in acute renal allograft rejection identified by DNA microarray profiling. N Engl J Med 2003; 349(2):125-38.
2. Flechner S M, Kurian S M, Solez K, et al. De novo kidney transplantation without use of calcineurin inhibitors preserves renal structure and function at two years. Am J Transplant 2004; 4(11):1776-85.
3. Kurian S M, Flechner S M, Kaouk J, et al. Laparoscopic donor nephrectomy gene expression profiling reveals upregulation of stress and ischemia associated genes compared to control kidneys. Transplantation 2005; 80(8):1067-71.
4. Morgun A, Shulzhenko N, Perez-Diez A, et al. Molecular profiling improves diagnoses of rejection and infection in transplanted organs. Circ Res 2006; 98(12):e74-83.
5. Hotchkiss H, Chu T T, Hancock W W, et al. Differential expression of profibrotic and growth factors in chronic allograft nephropathy. Transplantation 2006; 81(3):342-9.
6. Park W, Griffin M, Grande J P, Cosio F, Stegall M D. Molecular evidence of injury and inflammation in normal and fibrotic renal allografts one year posttransplant. Transplantation 2007; 83(11):1466-76.
7. Li L, Ying L, Naesens M, et al. Interference of globin genes with biomarker discovery for allograft rejection in peripheral blood samples. Physiol Genomics 2008; 32(2): 190-7.
8. Deng M C, Eisen H J, Mehra M R, et al. Noninvasive discrimination of rejection in cardiac allograft recipients using gene expression profiling. Am J Transplant 2006; 6(1):150-60.
9. Gwinner W. Renal transplant rejection markers. World journal of urology 2007; 25(5):445-55.
10. Racusen L C, Solez K, Colvin R B, et al. The Banff 97 working classification of renal allograft pathology. Kidney Int 1999; 55(2):713-23.
11. Efron B, Tibshirani R. Empirical bayes methods and false discovery rates for microarrays. Genet Epidemiol 2002; 23(1):70-86.
12. Chen R, Li L, Butte A. AILUN: reannotating gene expression data automatically. Nature Methods 2007; 4(11):In Press.
13. Perez-Iratxeta C, Andrade M A. Inconsistencies over time in 5% of NetAffx probe-to-gene annotations. BMC Bioinformatics 2005; 6:183.

14. Harbig J, Sprinkle R, Enkemann S A. A sequence-based identification of the genes detected by probesets on the Affymetrix U133 plus 2.0 array. Nucleic Acids Res 2005; 33(3):e31.

15. Witten I H, Frank E. Data Mining: Practical machine learning tools and techniques. 2nd ed. San Francisco: Morgan Kaufmann; 2005.

16. Li B, Hartono C, Ding R, et al. Noninvasive diagnosis of renal-allograft rejection by measurement of messenger RNA for perforin and granzyme B in urine. N Engl J Med 2001; 344(13):947-54.

17. Dugre F J, Gaudreau S, Belles-Isles M, Houde I, Roy R. Cytokine and cytotoxic molecule gene expression determined in peripheral blood mononuclear cells in the diagnosis of acute renal rejection. Transplantation 2000; 70(7):1074-80.

18. Simon T, Opelz G, Wiesel M, Ott R C, Susal C. Serial peripheral blood perforin and granzyme B gene expression measurements for prediction of acute rejection in kidney graft recipients. Am J Transplant 2003; 3(9):1121-7.

19. Vasconcellos L M, Schachter A D, Zheng X X, et al. Cytotoxic lymphocyte gene expression in peripheral blood leukocytes correlates with rejecting renal allografts. Transplantation 1998; 66(5):562-6.

20. Schwartz G J, Haycock G B, Edelmann C M, Jr., Spitzer A. A simple estimate of glomerular filtration rate in children derived from body length and plasma creatinine. Pediatrics 1976; 58(2):259-63.

Supplemental Methods

Patients and Samples 274 unique peripheral blood samples from 274 pediatric and young adult kidney allograft recipients were collected at Stanford University (n=193) and other SNS01 centers (n=81) (from 2002 to 2007). All blood samples were obtained at the time of matched clinically indicated or protocol graft biopsies which were used to categorize the sample as acute rejection (AR; n=109)[1], or stable, if there was absence of AR or other substantive pathology (STA, n=108). The diagnosis of acute rejection was confirmed on re-evaluation of all samples by a single pathologist (NK), before their inclusion in this study. AR samples were obtained prior to treatment intensification for rejection. An additional 57 sequential samples were also collected before AR (preAR, n=27) and after AR (postAR, n=30), and serial post-transplant blood samples were also collected from a subset of STA patients (n=70). Written informed consent was obtained from all the subjects. The study was approved by the Stanford Institutional Review Board and by each SNSO1 center Institutional Review Board.

Sample Collection, RNA Extraction, Microarray Target Preparation and Hybridization Peripheral blood samples were collected in the form of either whole blood (n=106) or peripheral blood leukocytes (PBL; n=16). All SNSO1 samples were collected as whole blood; the samples from Stanford were collected as PBL between 2002-2004, and as either whole blood or PBL, between 2004-2007.

For total RNA extracted from whole blood, 2.5 ml of peripheral blood was collected in PAXgene™ Blood RNA Tubes (PreAnalytiX, Qiagen) and processed using the PAXgene Blood RNA Kit (PreAnalytiX, Qiagen). For RNA extracted from leukocytes, 5-10 ml whole blood was collected in sodium heparin tubes. Leukocytes were recovered by initial separation of the white blood cells by centrifugation and lysis of erythrocytes[2]. RNA was extracted using RNeasy Midi Kit® (Qiagen Inc, Valencia, Calif.). RNA concentration was measured using NanoDrop® ND-1000 (NanoDrop Technologies, Wilmington, Del.) and the integrity of RNA was assessed with the Agilent 2100 Bioanalyzer using RNA Nano Chips (Agilent Technologies, Santa Clara, Calif.). RNA was stored in −80° C. until further use for microarray and Q-PCR.

Sample preparations for Affymetrix and Agilent array hybridizations were done using the T7 protocol (T7), which employs one-cycle cRNA synthesis by using T7-Oligo (dT) Primer. For Affymetrix arrays, a total of 2 μg total RNA, was used for the synthesis of cRNA as the final product following manufactures instructions. cRNA were hybridized on GeneChip® Human Genome U133 Plus 2.0 Arrays (Affymetrix Inc. Santa Clara, Calif.). 100 ng of total RNA was used for Agilent array hybridization following the manufacturer's instruction. Amplified and purified cRNA were incorporated with of Cy5 dye (test sample) or Cy3-dye (common reference as same as used in cDNA array), the mixture of two labeled samples was applied onto either Agilent Whole Human Genome Oligo Microarray 44 k or 4×44 k. cDNA microarrays[3], containing 32,000 cDNA clones (12,400 known unique genes), were processed using established protocols, using 2 ug RNA in each channel against a common reference (RNA pool from multiple tumor lines). Hybridized Affymetrix and cDNA microarrays were scanned using GenePix 4000 (Axon Instruments, Union City, Calif.) and fluorescent images were analyzed with the GenePix Pro software package. Agilent slides were scanned by using an Agilent DNA microarray scanner.

Gene Expression Profile Analyses

Different criteria were used for probe detection for different array platforms. For the Affymetrix HG133plus2.0 array, original array data were Quartile-Quartile normalized using dChip software (DNA-Chip Analyzer, www(dot)dchip(dot)org) after probe level intensities and quality were calculated and measured including median intensity, percent of probe set outliers, and percent of single probe outliers. For the Agilent 44 k, a cut off for absolute value of $\log_2$red channel/green channel >0.5 for at least one array was applied; data was normalized in GeneSpring. For the Lymphochip cDNA array, a mean of channel 1 intensity/media background intensity >1.5, and/or normalized mean of channel 2 intensity/media background intensity) >1.5 were used. Data was normalized in the Stanford Microarray Database (Stanford). All Gene expression values were transformed to log 2 for further analysis. Unique genes across all platforms were mapped based on mapping of transcripts (probe sets) to Human Gene Organization (HUGO) gene names.

Quantitative Real-Time PCR (Q-PCR)

The probes used for Q-PCR were selected from the Refseq ID for each gene from Applied Biosystems (ABI). The list of probes used is shown in FIG. 6A. cDNA was first transcribed from 500 ng total RNA in 11 ul, and denatured in 1 ul 10 mM dNTPs and 1 ul 300 ng/ul random hexamers at 65° C. for 15 min. 7 ul of the Q-PCR mixture [4 ul 5×binding buffer, 1 ul 0.1 M DTT, 1 ul SuperScript III RT(Invitrogen), 1 ul RNase OUT (Invitrogen)] was added to the denatured RNA tube in a final 20 ul. RT reaction was carried out in a PCR thermal cycler at 50° C. for 60 min, 72° C. for 15 min following by addition of 1 ul RNase H for 30 min at 37° C. to digest away remaining RNA template. Q-PCR was carried out following manufacture's protocol with modification. cDNA was diluted to 1.25 ng/ul. Quantitative RT-PCR reactions were carried out in 384-well plates in a 10 μl volume containing 4 μl of cDNA (5 ng), 1 μl of TaqMAN probe and 5 μl 2× gene expression master mix buffer (ABI, Foster City, Calif.). The Q-PCR reactions were run in an ABI 7700 sequence detector (Applied Biosystems, Foster City, Calif.) under cycle conditions (10 min at 95° C., 40 cycles of 15 s 95° C., 30 s at 60° C.) recommended by manufacturer. The relative amount of RNA expression was calculated using a comparative $C_T$ method. Expression values were normalized to 18S ribosomal RNA and control samples (Stratagene Universal RNA) on the plate.

Study Design

This study was undertaken as a sum of 3 projects (FIG. 1): In the first project, we performed cross-sectional microarray analysis of 122 peripheral blood samples collected either as 2.5 ml of whole blood samples (n=106) in PAXgene™ Blood RNA Tubes (PreAnalytiX, Qiagen), or as 5 ml of blood in sodium heparin tubes (n=16) for isolation of peripheral blood leukocytes (PBL). For this analysis, blood samples were collected at a single time point, timed with a biopsy where acute rejection was either confirmed as present (60 AR samples) or absent (62 STA samples). The samples were hybridized to one of 3 microarray platforms: Affymetrix (n=75, the 54K HGU133Plus2 Array), Agilent (n=26, 44K Whole Human Genome oligo Array), or the Lymphochip cDNA array (n=21, 32K cDNA clones). Microarray data generated from 3 array platforms were cross-compared, by mapping common and overlapping transcripts to Human Gene Organization (HUGO) gene names. Significant gene lists on each platform were identified using Significant Analysis of Microarray (SAM,[4]) with a common significance threshold of a false discovery rate (FDR) of <10%. We identified 525 common genes that were significantly differentially expressed in AR on all 3 platforms.

In the second project, 32 genes were selected for Q-PCR verification (see section Candidate Gene Selection Criteria) in 34 samples previously used in microarray (Verification Set). Of the 32 genes tested by Q-PCR, 10 most significant genes were selected for further validation on 42 independent samples (Validation Set 1) and an additional 64 independent samples (32 AR, 32 STA; Validation Set 2). We applied various classification models including linear discriminant analysis, 5 different Bayesian models, multilayer perceptron and logistic regression (multinomial and linear) models to the 10 gene-set in the Validation Set 1. Each of these models was applied to an independent set of 64 samples (Validation Set 2) for evaluating their sensitivities, specificities and accuracies. A multinomial logistic regression model using 5 out of the 10 gene-set yielded the best overall performance.

In the third project, we applied the 5-gene AR diagnosis model, to predict AR in 30 patients who had serially collected peripheral blood samples, collected before (n=27 samples) and after (n=30 samples) the AR episode. Longitudinal 5-gene Q-PCR analysis was done on paired blood samples collected 1 to 6 months prior to AR episode to estimate the prediction of AR injury, even at the time of unperturbed graft function. These were the only samples in the study that were not paired with graft biopsies. A similar analysis was done on samples collected 1 to 6 months after treatment of the AR episode (paired with graft biopsies performed to follow-up for AR resolution) to interrogate the effect of intensified immunosuppression on the 5 gene-set signature (FIG. 1).

Project 1—Discovery of AR Specific Genes Across Multiple Microarray Platforms

Gene Expression Profiling of Peripheral Blood Samples Across 3 Microarray Platforms Out of the 274 unique peripheral blood samples, 103 unique samples (47 AR, 56 STA) were hybridized on 122 microarrays (60 AR, 62 STA) from 3 different platforms. Out of the 103 peripheral blood samples, 75 were hybridized on Affymetrix HG U133 plus 2.0 microarrays, 26 on Agilent microarrays and 21 on cDNA microarrays. 17 samples were hybridized on 2 or more platforms for quality control purposes. For the samples that were hybridized on more than 1 platform, representative cross-platform correlations were as follows, r=0.6 between cDNA and Agilent, r=0.8 between Affymetrix and Agilent (see cross-reference of samples and assays shown in FIG. 18).

Significance Analysis of Microarrays

We applied significance analysis of microarray (SAM[4]) to identify differentially expressed genes for AR on all 3 platforms. All gene expression values were transformed to $\log_2$ before SAM analysis. False discovery rate (FDR)<10% was used as a threshold on all platforms. Using this threshold we identified 5285 genes on the Affymetrix array, 8642 genes on the Agilent array, and 2805 genes on the cDNA microarrays as differentially expressed genes of significance in AR (FIG. 5). Because each array platform uses different sets of genes, which are represented using different probe IDs, we used AILUN (http://ailun.stanford.edu)[5] to re-annotate the probe identifiers (IDs) with the current Entrez Gene IDs. Using the Entrez Gene IDs, we identified 525 genes that were differentially expressed on all 3 platforms (FIG. 5). At the same FDR, the cDNA platform seems to have the least number of significant AR genes, when compared to the Affymetrix and Agilent platforms (data not shown).

While these studies show that cross platform array comparisons of a carefully selected phenotypes, is a powerful approach to identify gene specific signatures, a portion of the overlapping genes across all platforms show a converse fold change across the 3 platforms, suggesting that there can be potential issues with clone IDs across the array platforms[6 7]. The most reliable genes selected for validation in this study were those that had the same fold change across the 3 platforms. In addition to selecting candidate genes from the microarray analysis for validation, we included Forkhead Box P3 (FOXP3), Perforin (PFN1) and Granzym B (GRZYB)[8 9 10], as these genes were previously reported to be increased in AR in blood.

Project 2—Verification and Validation of AR Specific Genes by Q-PCR

Candidate Gene Selection Criteria for Q-PCR

The aim of the second project of the study was to verify the results obtained from the first project using Q-PCR, and identify a smaller set of genes that could be used for further validation studies for AR specific blood biomarkers. We selected 32 genes from the 525 overlapping genes based on the following criteria: i) 12 genes were chosen as genes of biological relevance and differential expression across all 3 platforms (up-regulated genes: IFNGR1, RNF130, PBEF1, ITGAX, RYBP, CFLAR, PSEN1; down-regulated genes: NKTR, GOLGA8A, IL32, MCM7 and NFATC3), ii) 17 genes were selected with biological relevance and differentially expression on at least 2 platforms with fold change>1.5 and q<3% (up-regulated genes: DUSP1, SLP1, IL8RAP, STAT3, F2RL1, FCGR1A, IL6R, PTPRC, STAT1, IL1RAP, TLR8, TNFAIP6; down-regulated genes: MAPK9, PHLDA1, PTPN11, ZP70, PLCG1), iii) 3 genes were selected based on a priori published data on their potential as blood based AR biomarkers; perforin or PFN1[11], granzyme B or GRZYB[10 11] and the forkhead box P3 gene, FOXP3[8].

Verification by Q-PCR

Expression of the 32 genes in AR was verified using TagMan Gene Expression Assay products (Applied Biosystems, Foster City, Calif.) in 34 samples (Verification Set; 17 AR, 17 STA). These samples had been previously run on one or more arrays, and samples were selected based only on the criteria that the remaining sample had adequate RNA quantity and quality. The primer list for each of the 10 genes, and their corresponding ABI probe IDs are provided in FIG. 6A. Expression of the 10 most significant genes are shown in FIG. 6B. For each gene, no fluorescent signal was generated by these assays when genomic DNA was used as a template, which confirms that the assay measured only mRNA.

Ribosomal RNA 18s was used for endogenous RNA and cDNA quality control. 18s was chosen as a control gene, on the basis of this gene having relatively constant gene expression across AR samples and between AR and STA samples on array experiments. In order to control for possible variations among PCRs performed on different days, the expression of all genes were also assessed in Universal Human Reference RNA for each Q-PCR run. The assays were highly reproducible, with coefficient of variation less than 0.18 among 6 runs for each gene assessed in the Universal Human Reference RNA. Q-PCR was carried out in a 384-well plate, with each gene expression measurement performed in duplicates. The relative amount of RNA expression was calculated using a comparative $C_T$ method.

In addition to verifying the microarray results, another aim of project 2 was to refine the selection of a smaller, stringent set of genes that could be used validated as biomarkers for AR in independent patient samples. We selected the 10 most significant genes from the 32 genes verified by Q-PCR. Student's t-test was used for establishing the significance of gene expression differences between AR and STA samples by Q-PCR. All differences were considered statistically significant for $p<0.05$. These 10 genes were next validated for their significant expression differences in AR, by Q-PCR, in 42 independent samples (Validation Set 1; 21 AR, 21 STA) (FIG. 8).

Classification Modeling for AR

To ascertain the best classification model for a minimum gene set for AR diagnosis in blood, we applied 10 different classification models to the 10-gene set[12] he classification models used included Classification ViaRegression, variants of Bayesian models (NaiveBayes, MultinomialNaiveBayes, BayesNet, etc.), multilayer perceptron, logistic regression (multinomial and linear) and sequential minimal optimization. Each of these models were trained using the Q-PCR data for Validation set 1, and re-validated using Q-PCR data from 64 independent samples (Validation Set 2; 32 AR, 32 STA) (FIG. 9). Out of the 10 classification models, multinomial logistic regression model using 5 genes (DUSP1, MAPK9, NKTR, PBEF1, PSEN1) performed the best (sensitivity=100%, specificity=93.8%, PPV=94.1% 1, NPV=100%). FIG. 10 provides comparisons of all classification models used.

A first logistic regression model using the 5-genes set is shown in the following equation:

$$\theta = \frac{e^{10.0395+(1.8364*DUSP1)+(-1.9182*MAPK9)+(-1.8939*NKTR)+(4.9901*PBEF1)+(2.124*PSEN1)}}{1+e^{10.0395+(1.8364*DUSP1)+(-1.9182*MAPK9)+(-1.8939*NKTR)+(4.9901*PBEF1)+(2.124*PSEN1)}}$$

A second logistic regression model using a minimal 5-gene set is shown in the following equation:

$$\theta = \frac{e^{-18.6137+(3.8327*DUSP1)+(-5.1524*MAPK9)+(-3.6056*NKTR)+(8.3652*PBEF1)+(3.353*PSEN1)}}{1+e^{-18.6137+(3.8327*DUSP1)+(-5.1524*MAPK9)+(-3.6056*NKTR)+(8.3652*PBEF1)+(3.353*PSEN1)}}$$

The logistic regression model using a minimal 5-gene set based on the Stanford samples is shown in the following equation:

$$\theta = \frac{e^{-17.2226+(1.0735*IFNGR1)+(-7.7795*MAPK9)+(4.2314*PBEF1)+(3.7546*PSEN1)+(2.9103*RNF130)}}{1+e^{-17.2226+(1.0735*IFNGR1)+(-7.7795*MAPK9)+(4.2314*PBEF1)+(3.7546*PSEN1)+(2.9103*RNF130)}}$$

In each equation above, θ is the predicted probability. Based on the Receiver Operating Characteristic (ROC) curve, a cutoff of θ=0.5 was selected to determine whether the predictive class was an AR or STA phenotype.

Querying the Influence of Demographic and Clinical Confounders on the 5 Gene-Set Data was collected on 18 demographic and clinical variables on all samples processed for Q-PCR validation studies. Data was provided for SNSO1 samples by PPD (Brandon Graham, Jason Berg, David Ikle). The following 18 variables were studied: post-transplant time, recipient age, recipient gender, donor gender, donor source, donor age, cytomegalovirus/CMV, Epstein-Barr virus/EBV and BK virus/BKV viremia at sampling, concomitant bacterial infection, presence of donor specific antibodies (DSA) or panel reactive antibodies (PRA), usage of induction therapy, maintenance steroid usage, use of different calcineurin inhibitor drugs (FK506 or cyclosporine A/CSA), use of different anti-metabolites (mycophenolate mofetil/MMF or azathioprine/AZA), the white blood cell count (WBC) and the hematocrit (HCT) levels at the time of blood sampling (FIG. 11). Pearson correlation coefficients were calculated to determine any influence of 18 different clinical parameters as potential confounders for expression of the 5-genes set (FIG. 12). This analysis showed that the expressions of the 5 gene-set for diagnosis of AR, was not affected by any of the 18 confounders examined (maximum $|r|=0.27$). Additionally, t-test was performed for 13 clinical confounders with categorical values (recipient gender, donor gender, donor source, steroid-free versus steroid-based, CMV viremia, EBV viremia, BK viremia, bacterial infection, DSA, PRA, use of induction therapy or not, use of FK506 versus CSA, use of MMF versus AZA).

Querying the Influence of AR Severity (BANFF Scores), AR Type (Humoral or Cellular Rejection), Peritubular C4d Positivity at AR, on the Expression of the 5 Gene-Set Next, any associations between Banff scores, peri-tubular C4d+/− at biopsy and the presence of either humoral or cellular rejection, and expression of the 5-gene set for AR diagnosis, were examined. As most samples had pared biopsies for evaluation, samples were divided into 2 groups according to Banff score grades (1=Banff scores≤1A; 2=Banff score≥1B); $C4d^+$ was determined if there was ≥10% of peritubular capillaries (PTC) had C4d deposits. No correlation was found between AR probability prediction by the 5 gene-set and Banff scores (r=−0.13), humoral versus cellular rejection (r=0.07), and presence or absence of peri-tubular C4d+ (r=0.2) (FIG. 14).

Project 3—Prediction of AR Injury by the 5 Gene-Set, Prior to Indicated Graft Biopsy and Graft Dysfunction The aim of the third project in this study was to test whether the model with 5-gene set can predict the onset of AR, prior to any graft dysfunction or indicated biopsy. We applied our regression model to samples sequentially collected 1 to 6 month prior and after a biopsy proven AR episode. The samples were grouped into the following categories: i) samples collected 3 to 6 months prior to the onset of AR, ii) samples collected 0 to 3 months prior to AR, iii) samples collected at the time of AR, iv) samples collected 0 to 3 month after the AR episode, v) samples collected 3 to 6 months after the AR episode. FIG. 15 provides mean AR probabilities along with standard errors and calculated creatinine clearances[13] for each group of samples.

Biological Relevance Analysis of the 5 Gene-Set

To examine the key biological processes that could influence the peripheral transcriptome in AR, we applied the 525 cross platform AR specific gene-set for biological relevance analysis using the PANTHER classification system (http(colon)//www(dot)pantherdb(dot)org). These molecular pathways suggest active protein trafficking/transport and lipid metabolism in key pathways involved in immunity, cell cycling, apoptosis and differentiation. Ingenuity Pathway Analysis (http(colon)//www(dot)ingenuity(dot)com) shows that these genes drive canonical pathways in involved in apoptosis, and regulated by the JAK/STAT pathway (FIG. 16).

REFERENCES FOR SUPPLEMENTAL METHODS

1. Racusen L C, Solez K, Colvin R B, et al. The Banff 97 working classification of renal allograft pathology. Kidney Int 1999; 55(2):713-23.
2. Li L, Ying L, Naesens M, et al. Interference of globin genes with biomarker discovery for allograft rejection in peripheral blood samples. Physiol Genomics 2008; 32(2): 190-7.
3. Sarwal M, Chua M S, Kambham N, et al. Molecular heterogeneity in acute renal allograft rejection identified by DNA microarray profiling. N Engl J Med 2003; 349(2):125-38.
4. Efron B, Tibshirani R. Empirical bayes methods and false discovery rates for microarrays. Genet Epidemiol 2002; 23(1):70-86.
5. Chen R, Li L, Butte A. AILUN: reannotating gene expression data automatically. Nature Methods 2007; 4(11):In Press.
6. Perez-Iratxeta C, Andrade M A. Inconsistencies over time in 5% of NetAffx probe-to-gene annotations. BMC Bioinformatics 2005; 6:183.
7. Harbig J, Sprinkle R, Enkemann S A. A sequence-based identification of the genes detected by probesets on the Affymetrix U133 plus 2.0 array. Nucleic Acids Res 2005; 33(3):e31.
8. Li B, Hartono C, Ding R, et al. Noninvasive diagnosis of renal-allograft rejection by measurement of messenger RNA for perforin and granzyme B in urine. N Engl J Med 2001; 344(13):947-54.
9. Dugre F J, Gaudreau S, Belles-Isles M, Houde I, Roy R. Cytokine and cytotoxic molecule gene expression determined in peripheral blood mononuclear cells in the diagnosis of acute renal rejection. Transplantation 2000; 70(7):1074-80.
10. Simon T, Opelz G, Wiesel M, Ott R C, Susal C. Serial peripheral blood perforin and granzyme B gene expression measurements for prediction of acute rejection in kidney graft recipients. Am J Transplant 2003; 3(9):1121-7.
11. Vasconcellos L M, Schachter A D, Zheng X X, et al. Cytotoxic lymphocyte gene expression in peripheral blood leukocytes correlates with rejecting renal allografts. Transplantation 1998; 66(5):562-6.
12. Witten I H, Frank E. Data Mining: Practical machine learning tools and techniques. 2nd ed. San Francisco: Morgan Kaufmann; 2005.
13. Schwartz G J, Haycock G B, Edelmann C M, Jr., Spitzer A. A simple estimate of glomerular filtration rate in children derived from body length and plasma creatinine. Pediatrics 1976; 58(2):259-63.

Example II

Methods

A total of 40 time and immunosuppression matched peripheral blood samples from liver and heart transplant patients were selected for 384-well format multiplex ABI-TaqMan qPCR validation across the 10 gene-set identified in Example I. 16 of the samples were from liver transplant patients with 8AR and 8 stable without rejection (STA) and 24 samples were from heart transplant patients (9AR; 10STA); for virus confounder control, 5 STA samples with Cytomegalovirus infection (CMV) were included. The significance differential gene expression was determined by T test, with p<0.05 considered as significant.

Results

For the same 10 gene-set validation in liver transplant, 2 of the 10 genes (PSEN1 and RYBP) were highly significant for confirming peripheral blood AR diagnosis (p=0.05; p=0.04) in comparison to STA; the remaining 8 genes showed the same-direction fold changes as seen in kidney transplant, with no statistically significant difference between AR and STA. A prediction model generated from the 10 gene-set derived from peripheral blood of kidney transplant (ROC=97.6%) was applied to liver sample PCR dataset for AR classification, and revealed a prediction score of 86% sensitivity, 75% specificity, 88% PPV and 78% NPV, with 2 AR and 1 STA of the 16 samples misclassified. For 10 gene-set validation in heart samples, 3 of the 10 genes (CFLAR, ITGAX and NKTR) were differentially expressed in AR compared to STA (p=0.04; p=0.05; p=0.01). Interestingly, 1 of these 3 genes (CFLAR) shows significant opposite-direction fold changes (p=0.04, fold change=−2.2) as seen in kidney AR samples previously (p=0.002, fold change=3.1). Furthermore, 2 of the 3 genes were significantly down-regulated in CMV when compared to AR. There was no overlap in the significant differentially expressed genes between liver and heart. The identity of the 10 genes tested is shown in the previous discussion with kidney transplant samples.

CONCLUSION

A highly specific and sensitive biomarker of 10 genes derived and tested by cross-platform microarray analysis in kidney transplant can be used to predict AR in liver transplant. 2 of the 10 genes were differentially expressed in AR for both liver and heart, but no overlap of significantly differentially regulated genes between liver and heart suggests that rejection injury not only shares common biological pathways among different organ transplants, but also exhibits tissue specificity.

The 10 genes tested can be used to diagnose AR in both liver and heart transplant rejection, regardless of rejection grade.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system for monitoring a subject who has received an allograft for an acute rejection (AR) response, said system comprising:

(a) a gene expression evaluation element consisting of a collection of gene specific primers designed to selectively amplify genes selected from the group consisting of:

(i) CFLAR, RNF-130, IFNGR1, ITGAX, and RYBP;

(ii) NKTR, MAPK9, DUSP1, PBEF1, and PSEN1; and (iii) NKTR, MAPK9, DUSP1, PBEF1, PSEN1, CFLAR, IFNGR1, ITGAX, RNF-130 and RYBP, wherein at least one of the gene specific primers comprises a label selected from: biotin, fluorescein, digoxigenin, an antigen, a polyvalent cation, and a chelator group.

2. The system according to claim 1, wherein said system further comprises reagents for assaying a sample from said subject for an expression product of said genes.

3. The system according to claim 1, wherein said collection of gene specific primers comprises primers designed to selectively amplify the genes NKTR, MAPK9, DUSP1, PBEF1, PSEN1, CFLAR, RNF-130, IFNGR1, ITGAX and RYBP and said phenotype determination element is a reference expression profile for NKTR, MAPK9, DUSP1, PBEF1, PSEN1, CFLAR, RNF-130, IFNGR1, ITGAX, and RYBP.

4. The system of claim 2, wherein said sample is a blood sample.

5. The system of claim 1, wherein said allograft is a heart, kidney, liver, lung, pancreas, stomach, large intestine, small intestine or bladder allograft.

6. The system according to claim 1, wherein said collection of gene specific primers is designed to selectively amplify the genes CFLAR, RNF-130, IFNGR1, ITGAX, and RYBP.

7. The system according to claim 1, wherein said collection of gene specific primers is designed to selectively amplify the genes NKTR, MAPK9, DUSP1, PBEF1, and PSEN1.

8. The system of claim 1, wherein said gene specific primers are configured for use in quantitative PCR.

9. The system according to claim 1, wherein at least one of the gene specific primers comprises a directly detectable label selected from: an isotopic moiety and a fluorescent moiety.

10. The system of claim 9, wherein said directly detectable label is a fluorescent moiety.

11. The system according to claim 2, wherein said additional reagents are selected from the group consisting of: dNTPs, rNTPs, one or more uniquely labeled dNTPs, one or more uniquely labeled rNTPs, gold particles, silver particles, a chemically active derivative of a fluorescent dye, an enzyme, reverse transcriptase, DNA polymerase, RNA polymerase, a hybridization buffer, a wash buffer, a spin column, signal generation and detection reagent, a streptavidin-alkaline phosphatase conjugate, a chemifluorescent substrate, a chemiluminescent substrate; and a combination thereof.

12. The system according to claim 1, wherein the system further comprises a phenotype determination element, wherein said phenotype determination element is a database comprising a reference expression profile for said collection of gene specific primers recorded on a non-transitory computer readable medium, wherein the reference expression profile was obtained from a sample from a patient with an AR response.

* * * * *